US012589134B2

(12) United States Patent
Oft

(10) Patent No.: US 12,589,134 B2
(45) Date of Patent: Mar. 31, 2026

(54) COMPOSITIONS AND METHODS OF USE OF INTERLEUKIN-10 IN COMBINATION WITH IMMUNE CHECK-POINT PATHWAY INHIBITORS

(71) Applicant: Eli Lilly and Company, Indianapolis, IN (US)

(72) Inventor: Martin Oft, Palo Alto, CA (US)

(73) Assignee: Eli Lilly and Company, Indianapolis, IN (US)

( * ) Notice: Subject to any disclaimer, the term of this patent is extended or adjusted under 35 U.S.C. 154(b) by 57 days.

(21) Appl. No.: 18/488,796

(22) Filed: Oct. 17, 2023

(65) Prior Publication Data

US 2024/0108690 A1 Apr. 4, 2024

Related U.S. Application Data

(63) Continuation of application No. 16/753,923, filed as application No. PCT/US2018/058837 on Nov. 2, 2018, now abandoned.

(60) Provisional application No. 62/584,610, filed on Nov. 10, 2017.

(51) Int. Cl.

| | |
|---|---|
| ***A61K 38/20*** | (2006.01) |
| ***A61K 9/00*** | (2006.01) |
| ***A61K 39/395*** | (2006.01) |
| ***C07K 14/54*** | (2006.01) |
| ***C07K 16/28*** | (2006.01) |
| *A61K 39/00* | (2006.01) |

(52) U.S. Cl.

CPC ........ *A61K 38/2066* (2013.01); *A61K 9/0019* (2013.01); *A61K 39/3955* (2013.01); *C07K 14/5428* (2013.01); *C07K 16/28* (2013.01); *A61K 2039/505* (2013.01); *A61K 2039/54* (2013.01)

(58) Field of Classification Search

CPC ............ A61K 38/2066; A61K 39/3955; A61K 39/4636

See application file for complete search history.

(56) References Cited

U.S. PATENT DOCUMENTS

2016/0243196 A1* 8/2016 Mumm .............. A61K 39/3955

FOREIGN PATENT DOCUMENTS

| | | |
|---|---|---|
| WO | 2015/117930 A1 | 8/2015 |
| WO | 2017/035232 A1 | 3/2017 |
| WO | 2017/040660 A1 | 3/2017 |
| WO | 2017/079746 A2 | 5/2017 |

OTHER PUBLICATIONS

Gorby et al., Sci. Signal., 2020, vol. 13, eabc0653, p. 1-18.*
Qin et al., Front. Immunol., 2019, vol. 10, Article 2298.*
Spigel et al., J. Clin. Oncol., 34, No. 15_Suppl (May 20, 2016), p. 9017.*
Office Action, JP Application No. 2021-529235, dated May 7, 2024, 12 pages.
Decision on Rejection, CN Application No. 201880072311.5, dated May 6, 2024, 7 pages.
Carbone, D. P. et al., First-Line Nivolumab in Stage IV or Recurrent Non-Small-Cell Lung Cancer, N. Engl. J. Med., 2017, 2415-2426, 376 (25).
Goodman, A. M. et al., Tumor Mutational Burden as an Independent Predictor of Response to Immunotherapy in Diverse Cancers., Mol. Cancer. Ther., 2017, 2598-2608, 16 (11).
Naing, A. et al., Clinical activity and safety of pegylated human IL-10 (AM0010) in combination with anti-PD1., Journal of Clinical Oncology, 2016, 3018, 34 (15).
Schrock, A. et al., Updated Dataset Assessing Tumor Mutation Burden (TMB) as a Biomarker for Response to PD-1/PD-L1 Targeted Therapies in Lung Cancer (LC), Journal of Thoracic Oncology, 2017, S422, 12(1).
Chain A, Interleukin-10, National Library of Medicine, National Center for Biotechnology Information, 2020.
Chain A, Interleukin-10, National Library of Medicine, National Center for Biotechnology Information, 2012.
Office Action, JP Application No. 2020-544561, dated May 18, 2021, 8 pages.
Response to Office Action, JP Application No. 2020-544561, dated Sep. 2, 2021, 6 pages.
Decision of Refusal, JP Application No. 2020-544561, dated Nov. 2, 2021, 6 pages.
Reconsideration Report, JP Application No. 2020-544561, dated Mar. 10, 2022, 3 pages.
Office Action, JP Application No. 2020-544561, dated Sep. 5, 2023, 9 pages.
Response to Office Action, JP Application No. 2020-544561, dated Dec. 4, 2023, 4 pages.
Office Action, JP Application No. 2022-030627, dated Mar. 7, 2023, 2 pages.
Response to Office Action, JP Application No. 2022-030627, dated Sep. 6, 2023, 3 pages.
Office Action, JP Application No. 2022-030627, dated Dec. 19, 2023, 6 pages.
Office Action, CN Application No. 201880072311.5, dated May 31, 2023, 10 pages.
Search Report, CN Application No. 201880072311.5, dated May 31, 2023, 3 pages.

(Continued)

*Primary Examiner* — Xiaozhen Xie
(74) *Attorney, Agent, or Firm* — Nielsen IP Law LLC

(57) ABSTRACT

The present disclosure provides a method for the treatment of neoplastic disease in a mammalian subject the method comprising the administration of an IL-10 agent in combination with the administration of at least one modulator of at least one immune checkpoint pathway. The present disclosure further provides a method for the treatment of neoplastic disease wherein the neoplasm has a low or intermediate tumor mutation burden, low or intermediate level of expression of the immune checkpoint molecule, or metastatic neoplastic disease.

26 Claims, 6 Drawing Sheets

Figure 1:
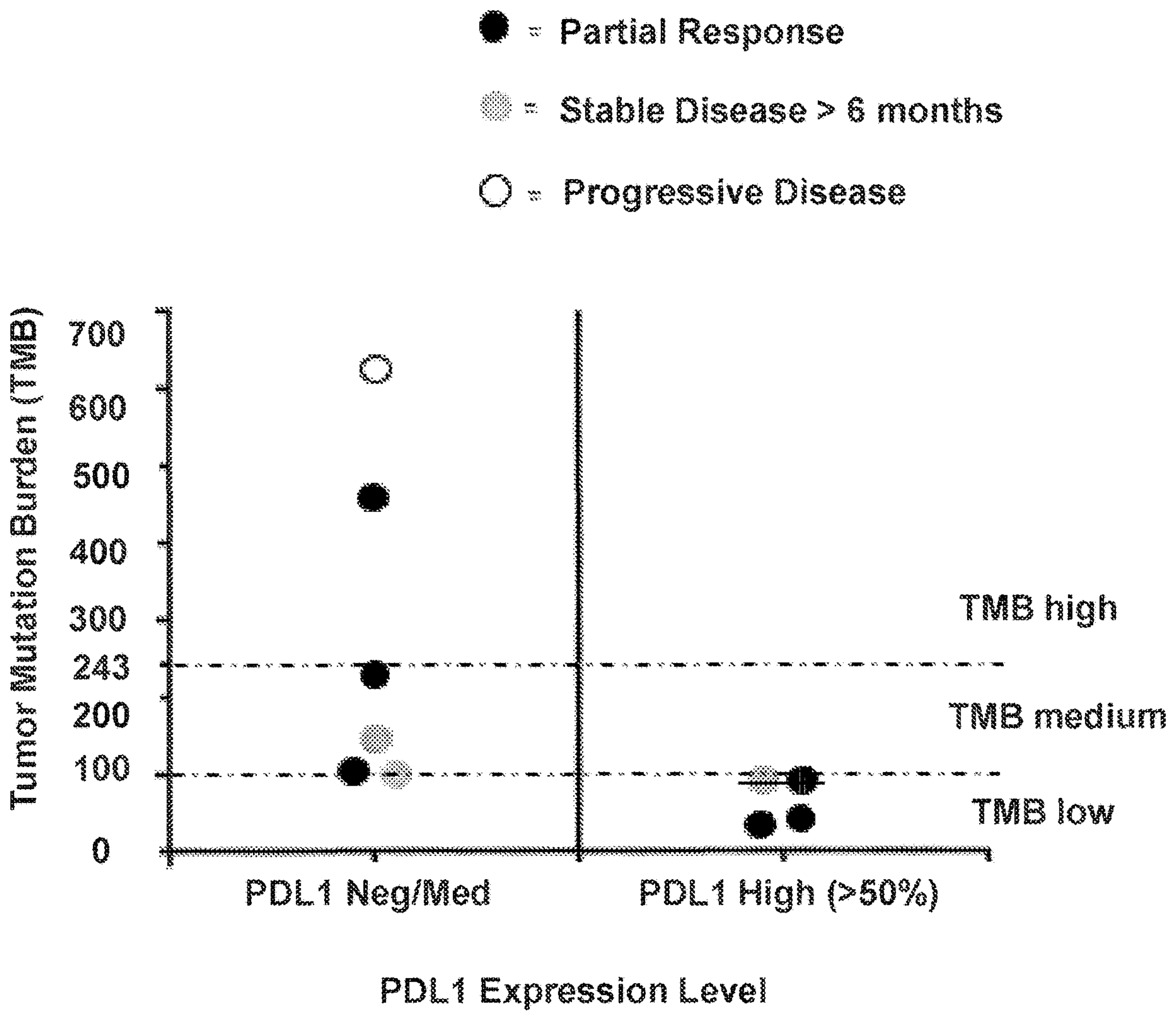

Specification includes a Sequence Listing.

(56) References Cited

OTHER PUBLICATIONS

Office Action, CN Application No. 201880072311.5, dated Dec. 27, 2023, 8 pages.
Office Action, CA Application No. 3,079,844, dated May 31, 2021, 7 pages.
Communication pursuant to Article 94(3) EPC, EP Application No. 18815831.5, dated May 4, 2021, 11 pages.
Response to Communication Pursuant to Article 94(3) EPC, EP Application No. 18815831.5, dated Nov. 10, 2021, 6 pages.
Communication pursuant to Article 94(3) EPC, EP Application No. 18815831.5, dated Feb. 16, 2022, 12 pages.
Response to Communication Pursuant to Article 94(3) EPC, EP Application No. 18815831.5, dated May 16, 2022, 2 pages.
Communication under Rule 71(3) EPC Intention to Grant, EP Application No. 18815831.5, dated Jun. 28, 2022, 5 pages.
Decision to Dismiss Amendment, JP Application No. 2022-030627, dated Jul. 30, 2024, 6 pages.
Decision of Refusal, JP Application No. 2022-030627, dated Jul. 30, 2024, 1 page.
Response to Office Action, JP Application No. 2020-54461, dated Jun. 18, 2024, 3 pages.
Trial and Appeal Decision, JP Application No. 2020-54461, dated Jul. 30 2024, 2 pages.

* cited by examiner

Pre-Treatment

A

B

COMPOSITIONS AND METHODS OF USE OF INTERLEUKIN-10 IN COMBINATION WITH IMMUNE CHECK-POINT PATHWAY INHIBITORS

CROSS REFERENCE TO RELATED APPLICATIONS

This application is a continuation of U.S. patent application Ser. No. 16/753,923 filed Apr. 6, 2020, now abandoned, which is the US National Stage of International Application No. PCT/US2018/058837 filed Nov. 2, 2018, which claims the benefit under 35 U.S.C. § 119 (e) of U.S. Provisional Application No. 62/584,610 filed Nov. 10, 2017. The foregoing applications are incorporated herein by reference.

SEQUENCE LISTING

The instant application contains a Sequence Listing which has been submitted electronically in XML file format and is hereby incorporated by reference in its entirety. Said XML copy, created on Oct. 17, 2023, is named X22058_44P53WOUS2_SL.xml and is 61,792 bytes in size.

This invention relates to methods of using IL-10 agents in combination with immune checkpoint pathway inhibitors in the treatment or prevention of diseases and disorders, including cancers and immune-related disorders.

The cytokine interleukin-10 (IL-10) is a pleiotropic cytokine that regulates multiple immune responses through actions on T cells, B cells, macrophages, and antigen presenting cells (APC). IL-10 can suppress immune responses by inhibiting expression of IL-1α, IL-1β, IL-6, IL-8, TNF-α, GM-CSF and G-CSF in activated monocytes and activated macrophages, and it also suppresses IFN-γ production by NK cells. Although IL-10 is predominantly expressed in macrophages, expression has also been detected in activated T cells, B cells, mast cells, and monocytes. In addition to suppressing immune responses, IL-10 exhibits immunostimulatory properties, including stimulating the proliferation of IL-2- and IL-4-treated thymocytes, enhancing the viability of B cells, and stimulating the expression of MHC class II.

As a result of its pleiotropic activity, IL-10 has been linked to a broad range of diseases, disorders and conditions, including inflammatory conditions, immune-related disorders, fibrotic disorders, metabolic disorders and cancer. Clinical and pre-clinical evaluations with IL-10 for a number of such diseases, disorders and conditions have solidified its therapeutic potential in the treatment in multiple applications. Moreover, variants of IL-10 such as pegylated IL-10 have demonstrated efficacy in multiple therapeutic applications including the treatment of cancer (see e.g., U.S. Pat. Nos. 8,865,652 and 9,364,517).

The broad range of genetic and epigenetic alterations characteristic of tumor cells provides a diverse set of antigens that the immune system can use to distinguish tumor cells from their normal counterparts. In the case of T-cell mediated response, the magnitude (e.g., levels of cytokine production or proliferation) and quality (e.g., the type of immune response generated, such as the pattern of cytokine production) of the immune response initiated through antigen recognition by the T-cell receptor (TCR), is regulated by a balance between co-stimulatory and inhibitory signals. While co-stimulatory and inhibitory receptors and ligands that regulate T-cell activation are frequently not over-expressed in cancers relative to normal tissues, inhibitory ligands and receptors that regulate T cell effector functions in tissues are commonly overexpressed on tumor cells or on non-transformed cells associated with the tumor microenvironment.

T cell-mediated immunity includes multiple sequential steps, each of which is regulated by counterbalancing stimulatory and inhibitory signals in order to optimize the response. Under normal conditions, the balance of stimulatory and inhibitory plays an important role in the prevention of autoimmunity (i.e., the maintenance of self-tolerance) and to ensure an appropriate response that minimizes tissue damage when the immune system is responding to pathogenic infection. While nearly all stimulatory or inhibitory signals of the immune response ultimately modulate intracellular signaling pathways, many are initiated through membrane receptors, the ligands of which are either membrane-bound or soluble.

Immune checkpoint pathways refer to a collection of pathways integrated into the immune system that are crucial for maintaining self-tolerance and modulating the duration and amplitude of physiological immune responses in peripheral tissues in order to minimize collateral tissue damage. In some instances, tumors assume control over certain immune-checkpoint pathways as a major mechanism of immune resistance, particularly against T cells that are specific for tumor antigens. See, e.g., Stagg and Allard, (2013) Ther. Adv. Med. Oncol. 5(3):169-81. Because signaling through many of the immune checkpoint pathways is initiated by ligand-receptor interactions, immune checkpoint pathways can be modulated by a variety of agents such as antibodies, recombinant forms of ligands or receptors, and small molecule compounds. In contrast to most antibodies currently approved for cancer therapy which are directed against tumor specific antigens, modulators of the immune checkpoints do not target tumor cells directly, but rather target lymphocyte receptors or their ligands in order to modulate endogenous antitumor activity. See Pardoll, (2012) Nature Rev. Cancer 12:252-64.

Perhaps the most well studied example of an immune checkpoint pathway and its relationship to cancer is the PD1 pathway. The immune checkpoint pathway activated by the interaction of PD1 (programmed cell death protein 1; also known as CD279) with its counterpart PDL1 (PD1 ligand; also known as B7-H1) negatively regulates T-cells. PD1 limits T-cell effector functions within tissues. Tumors may escape host immune surveillance by expressing PD-L1, which negatively regulates immune responses by interacting with PD1 on T cells. Iwai Y, et al. (2002) PNAS(USA) 99:12293-7. By up-regulating the expression of PDL1 tumor cells can block antitumor immune responses in the tumor microenvironment and induce T-cell exhaustion. Data from clinical samples suggest that elevated expression of PD1 ligands on tumors correlates with poor prognosis. Thompson R H, et al. (2004) PNAS(USA) 101:17174-9; and Thompson R H, et al. (2007) PNAS(USA) 19:813-24. The administration of agents that interfere with PD1/PDL1 binding results in inhibition of the PD1 immune checkpoint pathway reversing T cell exhaustion, restoring cytokine production, and augmenting the expansion of antigen-dependent T-cells. Agents that interfere with the binding of PD1 to PDL1 and/or PDL2 have demonstrated utility and/or promise in a number of diseases, disorders and conditions, including transplantation, infection, tumor, and autoimmune disease (Wu et al., (2012) Int. J. Biol. Sci. 8:1420-30).

However, the clinical effectiveness of such immune checkpoint pathway modulators shown diminished efficacy in some tumors, particularly in those tumors having a low tumor mutation burden and in those tumors where the PDL1 and/or IFNγ related gene expression is low. The present invention provides compositions and methods for the treatment of neoplastic diseases employing the combined effects of IL-10 agents and modulators of immune checkpoint pathways.

The present disclosure provides a method for the treatment of neoplastic disease in a mammalian subject the method comprising the administration of an IL-10 agent in combination with the administration of at least one modulator of at least one immune checkpoint pathway.

The present disclosure further provides a method for the treatment of neoplastic disease in a mammalian subject the method comprising the administration of an IL-10 agent in combination with the administration of at least one modulator of at least one immune checkpoint pathway wherein the neoplasm has a low or intermediate tumor mutation burden.

The present disclosure further provides a method for the treatment of neoplastic disease in a mammalian subject the method comprising the administration of an IL-10 agent in combination with the administration of at least one modulator of at least one immune checkpoint pathway wherein the neoplasm has a low or intermediate level of expression of the immune checkpoint molecule.

The present disclosure further provides a method for the treatment of metastatic neoplastic disease in a mammalian subject the method comprising the administration of an IL-10 agent in combination with the administration of at least one modulator of at least one immune checkpoint pathway.

The present disclosure further provides a method for the treatment of neoplastic disease in a mammalian subject the method comprising the administration of an IL-10 agent in combination with a PD1 immune checkpoint pathway inhibitor.

The present disclosure further provides a method for the treatment of neoplastic disease in a mammalian subject the method comprising the administration of an IL-10 agent in combination with pembrolizumab for the treatment of neoplastic disease.

In another embodiment, the present invention pharmaceutical formulations of IL-10 agents in combination with nivolumab for the treatment of cancer.

FIG. 1 provides a graphical illustration of results obtained a human clinical trial designed to evaluate the response of subjects suffering from non-small cell lung cancer (NSCLC) to the administration of combination of an IL-10 agent (AM0010) with anti-PD1 antibodies nivolumab and pembrolizumab with respect to tumor PDL1 expression and tumor mutational burden. This figure illustrates that the administration of a AM0010 in combination anti-PD1 antibody therapy is effective in producing a favorable clinical outcome in patients with low or intermediate tumor mutation burden and low or intermediate PDL1 expression levels.

Figure 2:
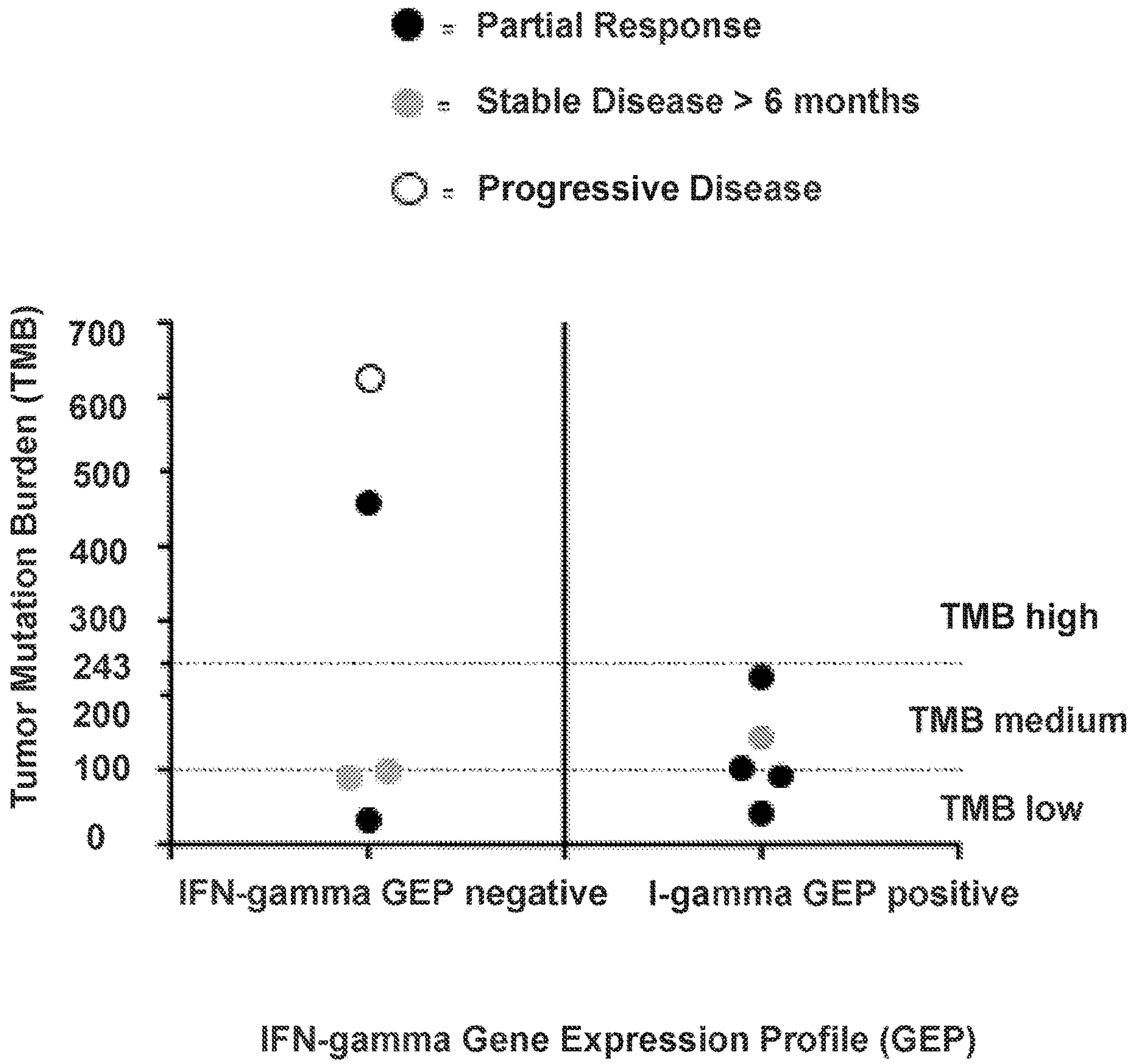

FIG. 2 provides a graphical illustration of results obtained in human clinical trials evaluating the response in subjects suffering from non-small cell lung cancer (NSCLC) to the combination of an IL-10 agent (AM0010) with the anti-PD1 antibodies nivolumab and pembrolizumab with respect to the expression interferon gamma gene expression profile comprising the genes STAT1, HLA-DRA, CXCL9, IDO, IFN-γ, and CXCL10 and tumor mutational burden. This figure illustrates that the administration of a AM0010 in combination anti-PD1 antibody therapy is effective in producing a favorable clinical outcome in patients with low IFNγ expression profile and low PDL1 expression levels.

Figure 3:
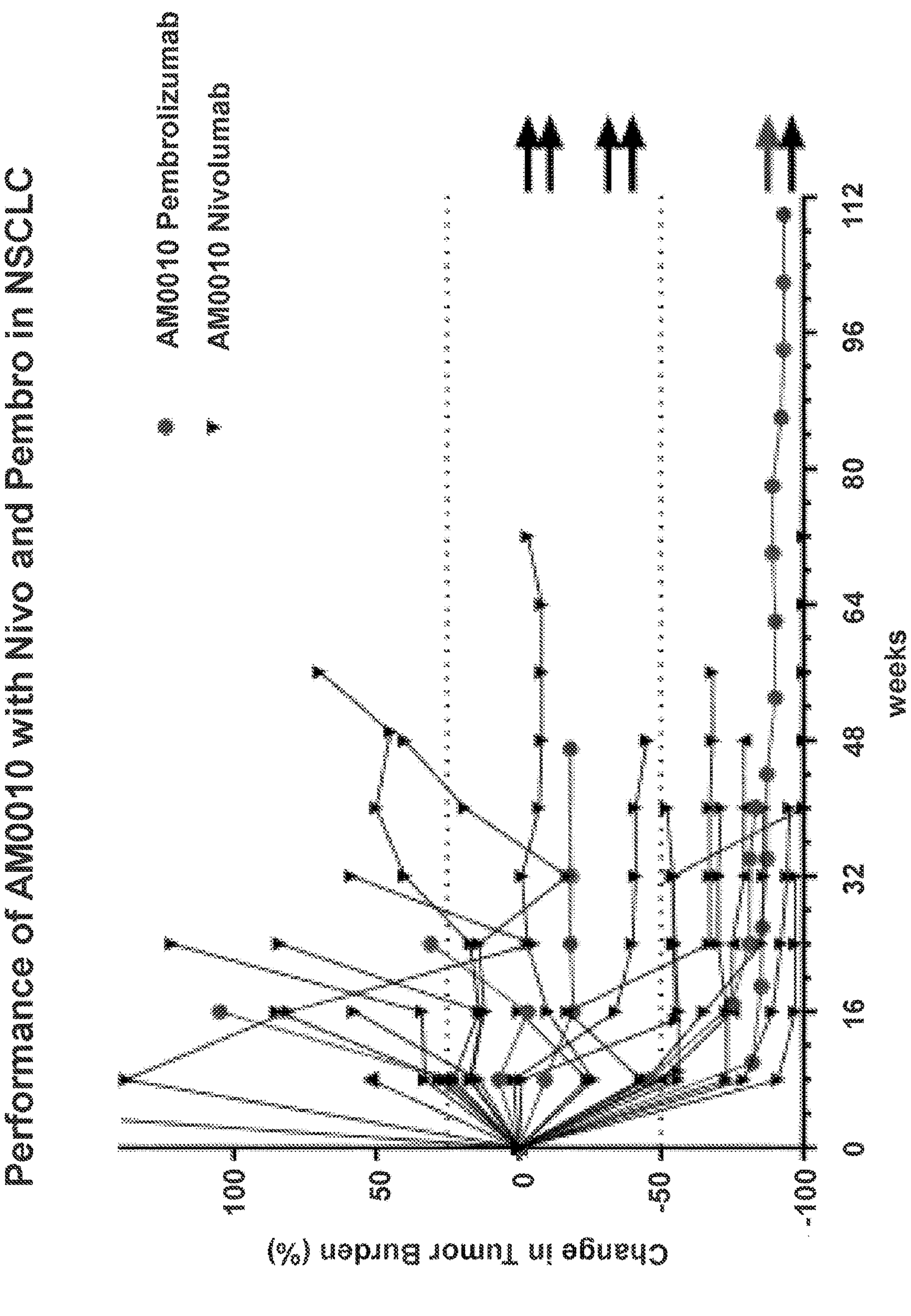

FIG. 3 provides a graphical illustration of results obtained in a human clinical trial designed to evaluate the change in tumor burden (percent) in subjects suffering from non-small cell lung cancer (NSCLC) to the combination of an IL-10 agent (AM0010) and the anti-PD1 antibodies nivolumab and pembrolizumab as a function of the duration of treatment with the combination therapy as more fully described below.

Figure 4:
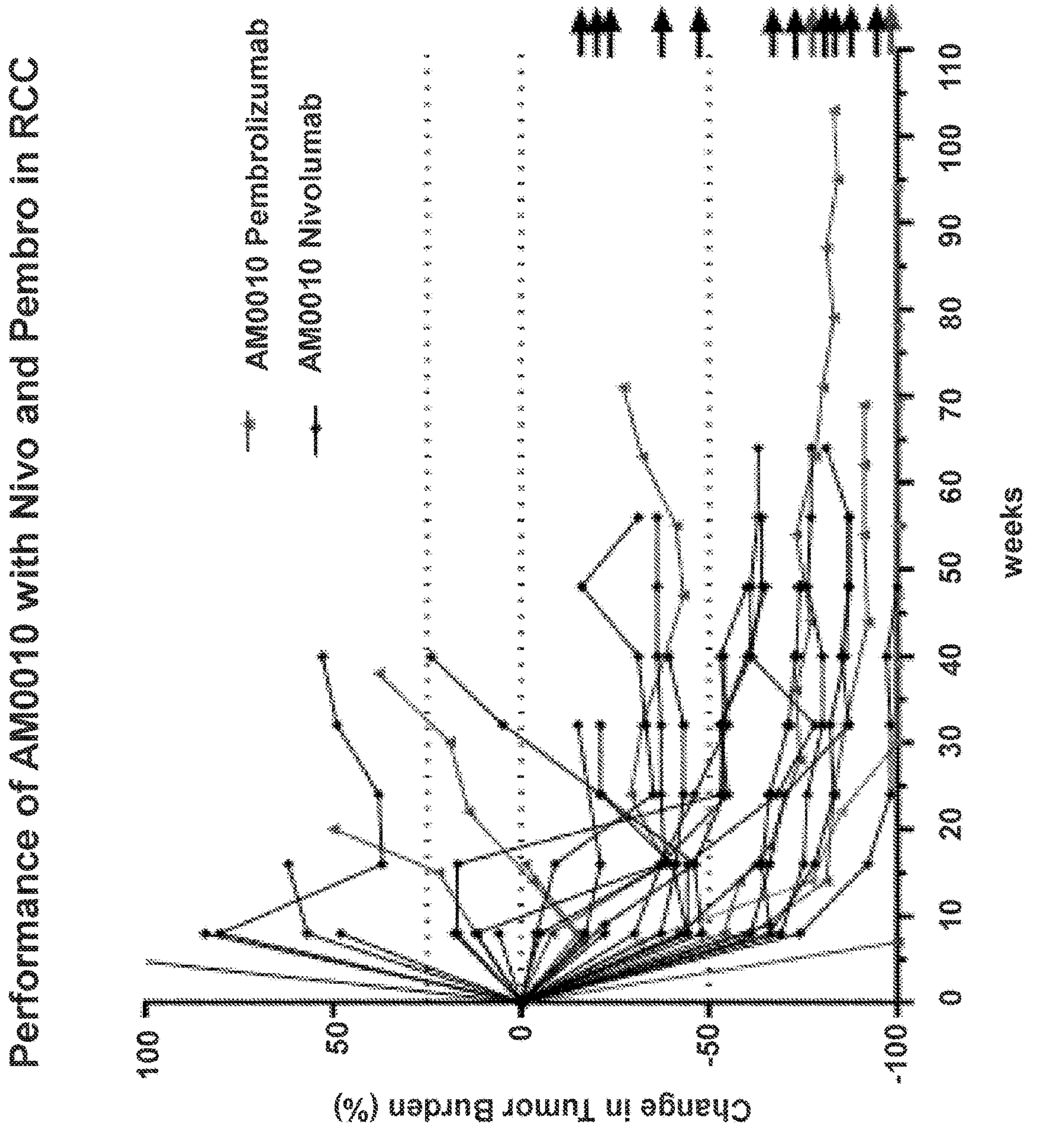

FIG. 4 provides a graphical illustration of results obtained in obtained in a human clinical trial designed to evaluate the change in tumor burden (percent) in subjects suffering from renal cell carcinoma (RCC) to the administration of combination of an IL-10 agent (AM0010) and the anti-PD1 antibodies nivolumab and pembrolizumab as a function of the duration of treatment with the combination therapy as more fully described below.

Figure 5:
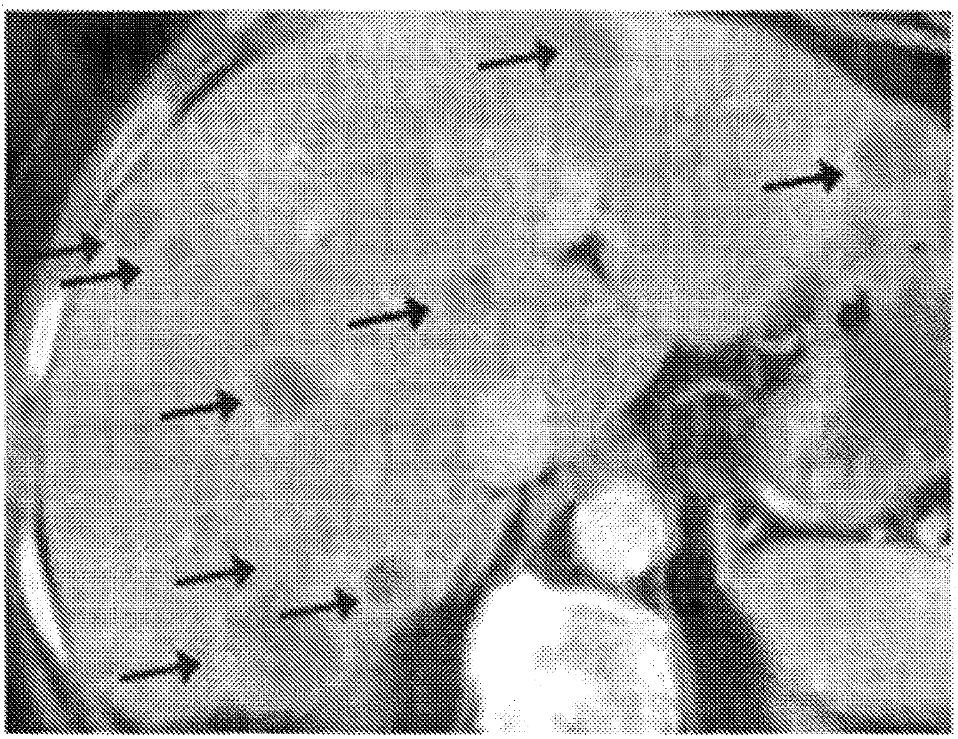
Figure 5:
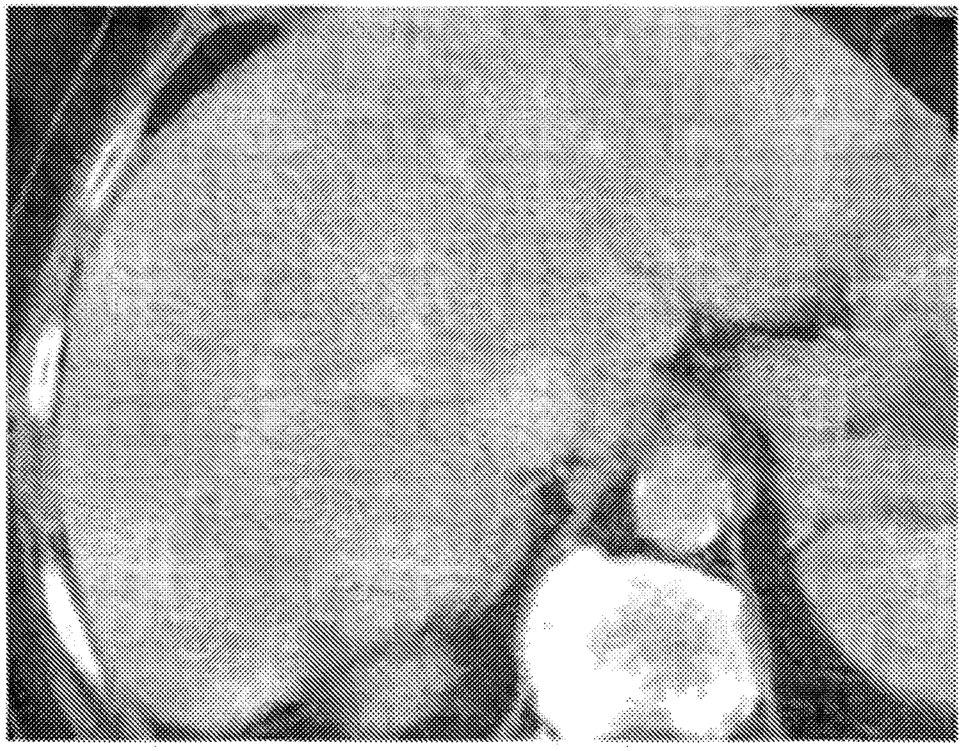

FIG. 5, Panels A and B provide histological examinations of liver tissues obtained from a human clinical trial subject suffering from non-small cell lung cancer (NSCLC) before treatment (Panel A) and after 7 months of treatment with a combination of an IL-10 agent (AM0010) and pembrolizumab anti-PD1 therapy according to the treatment protocol more fully described in hereinbelow (Panel B). The arrows in FIG. 5, Panel A, illustrate the presence of metastatic lesions in the liver. Panel B illustrates that such lesions have been significantly reduced or eliminated in response to the administration of the combination of an IL-10 agent and a modulator of an immune checkpoint pathway.

Figure 6:
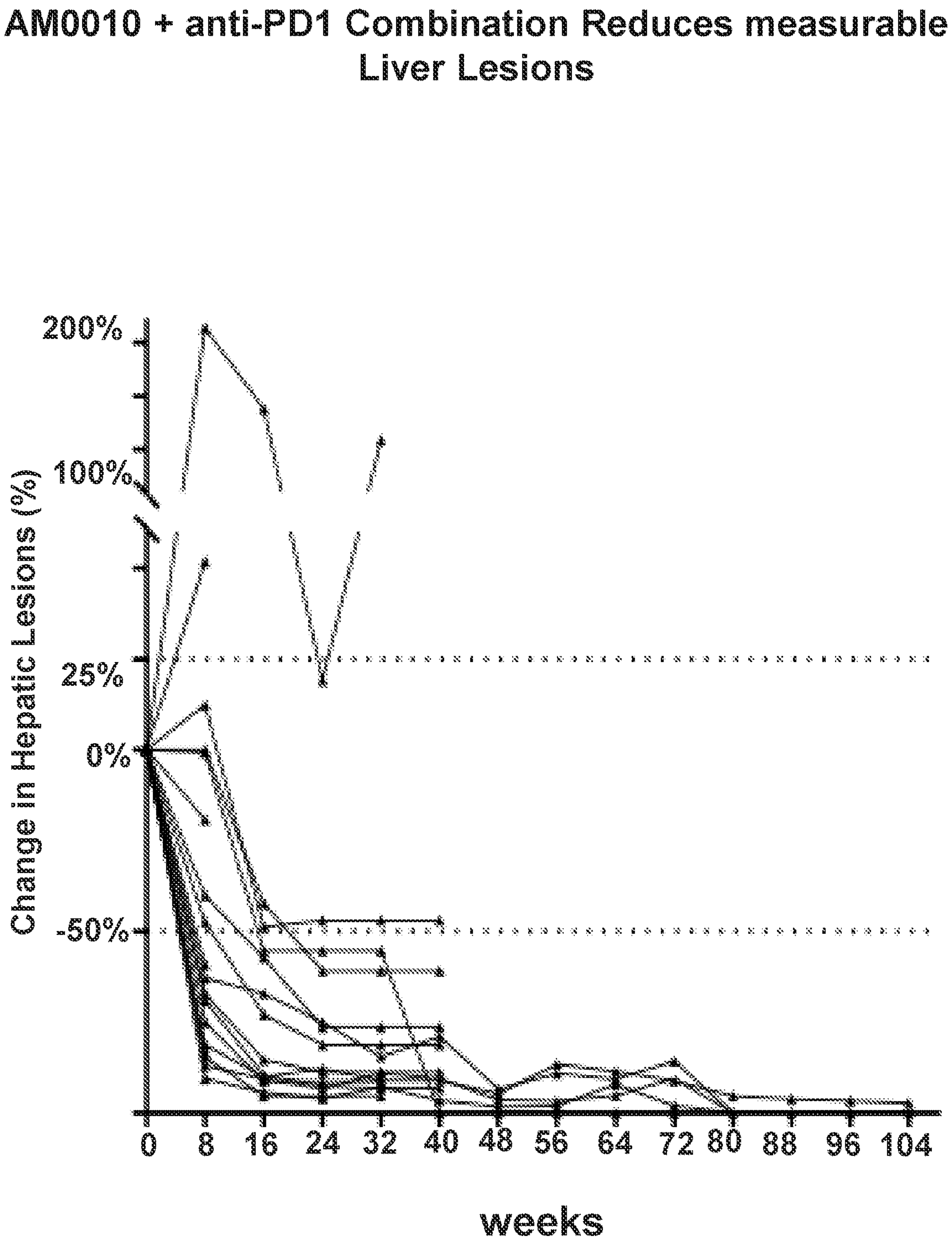

FIG. 6 provides graphical representation of the change the number of measurable hepatic lesions determined by histological examinations of liver tissues obtained from human clinical trial subjects suffering from non-small cell lung cancer (NSCLC) as a function of weeks of treatment with a combination of AM0010 and pembrolizumab according to the treatment protocol more fully described hereinbelow. This graph illustrates that the combination of AM0010 and pembrolizumab result in a significant reduction in measurable liver lesions in NSCLC patients demonstrating the effectiveness of the administration of the combination of an IL-10 agent and a modulator of an immune checkpoint pathway in the treatment in metastatic neoplastic disease.

Before the present disclosure is further described, it is to be understood that the disclosure is not limited to the particular embodiments set forth herein, and it is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges can independently be included in the smaller ranges, and are also encompassed within the invention, subject to any specifically excluded limit in the stated range. Where the stated range includes one or both of the limits, ranges excluding either or both of those included limits are also included in the invention. Unless defined otherwise, all technical and scientific terms used herein have the same meaning as commonly understood by one of ordinary skill in the art to which this invention belongs.

It must be noted that as used herein and in the appended claims, the singular forms "a," "an," and "the" include plural referents unless the context clearly dictates otherwise. It is further noted that the claims may be drafted to exclude any optional element. As such, this statement is intended to serve as antecedent basis for use of such exclusive terminology such as "solely," "only" and the like in connection with the recitation of claim elements, or use of a "negative" limitation.

Unless indicated otherwise, parts are parts by weight, molecular weight is weight average molecular weight, temperature is in degrees Celsius (° C.), and pressure is at or near atmospheric. Standard abbreviations are used, including the following: bp=base pair(s); kb=kilobase(s); pl=picoliter(s); s or sec=second(s); min=minute(s); h or hr=hour(s); aa=amino acid(s); kb=kilobase(s); nt=nucleotide(s); pg=picogram; ng=nanogram; g=microgram; mg=milligram; g=gram; kg=kilogram; dl or dL=deciliter; μl or μL=microliter; ml or mL=milliliter; 1 or L=liter; M=micromolar; mM=millimolar; M=molar; kDa=kilodalton; i.m.=intramuscular(ly); i.p.=intraperitoneal (ly); SC or SQ=subcutaneous(ly); QD=daily; BID=twice daily; QW=weekly; QM=monthly; HPLC=high performance liquid chromatography; BW=body weight; U=unit; ns=not statistically significant; PBS=phosphate-buffered saline; PCR=polymerase chain reaction; NHS=N-Hydroxysuccinimide; HSA=human serum albumin; MSA=mouse serum albumin; DMEM=Dulbeco's Modification of Eagle's Medium; GC=genome copy; EDTA=ethylenediaminetetraacetic acid.

Standard methods in molecular biology are described in the scientific literature (see, e.g., Sambrook and Russell (2001) Molecular Cloning, 3rd ed., Cold Spring Harbor Laboratory Press, Cold Spring Harbor, N.Y.; and Ausubel, et al. (2001) Current Protocols in Molecular Biology, Vols. 1-4, John Wiley and Sons, Inc. New York, N.Y., which describes cloning in bacterial cells and DNA mutagenesis (Vol. 1), cloning in mammalian cells and yeast (Vol. 2), glycoconjugates and protein expression (Vol. 3), and bioinformatics (Vol. 4)).

The scientific literature describes methods for protein purification, including immunoprecipitation, chromatography, electrophoresis, centrifugation, and crystallization, as well as chemical analysis, chemical modification, posttranslational modification, production of fusion proteins, and glycosylation of proteins (see, e.g., Coligan, et al. (2000) Current Protocols in Protein Science, Vols. 1-2, John Wiley and Sons, Inc., NY).

Unless otherwise indicated, the following terms are intended to have the meaning set forth below. Other terms are defined elsewhere throughout the specification.

As used herein, the term "activity" refers to a property of a molecule that when it contacts another molecule resulting in a measurable response. Examples of "activities" of a molecule include but are not limited to: (a) the ability of a molecule to bind to a ligand or receptor; (b) the ability of a molecule to induce or inhibit catalytic activity of an enzyme; (c) the ability of a molecule to stimulate gene expression or cell signaling, differentiation, or maturation; to antigenic activity; (d) the ability of a molecule to modulate the activities of other molecules. The "activity" may be quantified and is typically expressed as the degree of the effect with respect to the quantity of the molecule, e.g., [catalytic activity]/[mg protein], or [immunological activity]/[mg protein]. The term "bioactivity" is used to describe the activity of an agent in a biological system.

As used herein, the terms "administration" and "administer" are used interchangeably to refer the act of contacting a subject, including contacting a cell, tissue, organ, or biological fluid in vitro, in vivo or ex vivo of the subject, with an agent. When the agent is an IL-10 agent, term "administration", "administer", and "treat" it refers to the contacting of a subject or a cell, tissue, organ, or biological fluid of the subject in vitro, in vivo or ex vivo with a composition comprising an IL-10 agent. Administration of an agent may be achieved through any of a variety of art recognized methods including but not limited to the topical, intravenous including intravenous infusion, intradermal, subcutaneous, intramuscular, intraperitoneal, intracranial, intratumoral, subcutaneous, transdermal, transmucosal, intralymphatic, intragastric, intraprostatic, intravascular including intravenous, intraaterial, intravesical (to the bladder), iontophoresis, respiratory, intraocular, intraabdominal, intralesional intraovarian, intracerebral, iracerebroventricular injection (ICVI), and the like. The term "administration" includes contact of an agent to the cell, as well as contact of an agent to a fluid, where the fluid is in contact with the cell.

As used herein, the term "adverse event" refers to any undesirable experience associated with the use of a compound in a patient. Adverse events do not have to be caused by the compound. Adverser events may be mild, moderate, or severe. The classification of adverse events as used herein is in accordance with the Common Terminology Criteria for Adverse Events v4.03 (CTCAE) dated Jun. 14, 2010 published by the United States Department of Health and Human services, National Institutes of Health National Cancer Institute.

As used herein, the term "agonist" refers a molecule that interacts with a target to cause or promote an increase in the activation of the target. Activators or agonists are molecules that increase, activate, facilitate, enhance activation, sensitize, or up-regulate, e. g., a gene, protein, ligand, receptor, biological pathway (including an immune checkpoint pathway), or cell.

As used herein, the term "antagonist" or "inhibitor" refers a molecule that opposes the action(s) of an agonist. An antagonist prevents, reduces, inhibits, or neutralizes the activity of an agonist, and an antagonist can also prevent, inhibit, or reduce constitutive activity of a target, e.g., a target receptor, even where there is no identified agonist. Inhibitors are molecules that decrease, block, prevent, delay activation, inactivate, desensitize, or down-regulate, e.g., a gene, protein, ligand, receptor, biological pathway including an immune checkpoint pathway, or cell.

As used herein, the term "antibody" refers collectively to: (a) glycosylated and non-glycosylated immunoglobulins (including but not limited to mammalian immunoglobulin classes IgG1, IgG2, IgG3 and IgG4) that specifically binds to target molecule and (b) immunoglobulin derivatives including but not limited to IgG(1-4)deltaC$_H$2, F(ab')$_2$, Fab, ScFv, VH, VL, tetrabodies, triabodies, diabodies, dsFv, F(ab')$_3$, scFv-Fc and (scFv)$_2$ that competes with the immunoglobulin from which it was derived for binding to the target molecule. The term antibody is not restricted to immunoglobulins derived from any particular mammalian species and includes murine, human, equine, camel, and human antibodies. The term "antibody" encompasses naturally occurring antibodies isolatable from natural sources and as well as engineered antibodies including monoclonal antibodies, bispecific antibodies, chimeric antibodies, humanized antibodies, human antibodies, CDR-grafted, veneered, or deimmunized (e.g., to remove T cell epitopes) antibodies. The term "antibody" should not be construed as limited to any particular means of synthesis and includes naturally occurring antibodies isolatable from natural sources and as well as engineered antibodies molecules that are obtained by "recombinant" means including antibodies isolated from transgenic animals that are transgenic for human immunoglobulin genes or a hybridoma prepared therefrom, antibodies isolated from a host cell transformed with a nucleic acid construct that results in expression of an antibody, antibodies isolated from a combinatorial antibody library including phage display libraries. In one embodiment, an "antibody" is a mammalian immunoglobulin that is a "full length antibody" comprising variable and constant domains providing binding and effector functions. In most instances, a full-length antibody comprises two light chains and two heavy chains, each light chain comprising a variable region and a constant region. In one embodiment, the antibody is a is a "full length antibody" comprising two light chains and two heavy chains, each light chain comprising a variable region and a constant region providing binding and effector functions. In a preferred embodiment, the constant and variable regions are "human" (i.e. possessing amino acid sequences characteristic of human immunoglobulins).

As used herein the term "circulating tumor cell (CTC)" refers to tumor cells shed from the tumor mass into peripheral circulation.

As used herein, the term "comparable" is used to describe the degree of difference in two measurements of an evaluable parameter. For example, where a first measurement of an evaluable parameter (e.g. IL-10 activity as determined by an IL-10 assay) and a second measurement of the evaluable parameter do not deviate beyond an acceptable range (i.e., a range that the skilled artisan would recognize as not producing a statistically significant difference in effect between the two results in the circumstances) the two measurements would be considered "comparable." In some instances, measurements may be considered "comparable" if one measurement deviates from another by less than 35%, by less than 30%, by less than 25%, by less than 20%, by less than 15%, by less than 10%, by less than 7%, by less than 5%, by less than 4%, by less than 3%, by less than 2%, or by less than 1%. In particular embodiments, one measurement is comparable to a reference standard if it deviates by less than 15%, by less than 10%, or by less than 5% from the reference standard.

As used herein the terms "Complete Response (CR)," "Partial Response (PR)" "Stable Disease (SD)" and "Progressive Disease (PD)" with respect to target lesions and the terms "Complete Response (CR)," "Incomplete Response/Stable Disease (SD)" and Progressive Disease (PD) with respect to non-target lesions are understood to be as defined in the RECIST criteria.

The term "derived from" as used herein in the context of an amino acid sequence or polynucleotide sequence (e.g., an amino acid sequence "derived from" an IL-10 polypeptide), is meant to indicate that the polypeptide or nucleic acid has a sequence that is based on that of a reference polypeptide or nucleic acid (e.g., a naturally occurring IL-10 polypeptide or an IL-10-encoding nucleic acid), and is not meant to be limiting as to the source or method in which the protein or nucleic acid is made. By way of example, the term "derived from" includes homologs and muteins of reference amino acid or DNA sequences.

As used herein the term "driver mutation" refers to a mutation in a neoplastic cell that contributes to the growth and survival of the neoplasm and thereby conferring a selective advantage.

As used herein the terms "immune-related Complete Response (irCR)," "immune-related Partial Response (irPR)," "immune-related Progressive Disease (irPD)" and "immune-related Stable Disease (irSD)" as defined in accordance with the Immune-Related Response Criteria (irRC).

As used herein, the term "DNA", "nucleic acid", "nucleic acid molecule", "polynucleotide" and the like are used interchangeably herein to refer to a polymeric form of nucleotides of any length, either deoxyribonucleotides or ribonucleotides, or analogs thereof. Non-limiting examples of polynucleotides include linear and circular nucleic acids, messenger RNA (mRNA), complementary DNA (cDNA), recombinant polynucleotides, vectors, probes, primers and the like.

As used herein, the term "Immune-Related Response Criteria (irRC)" refers to a system for evaluation of reponse to immunotherapies as described in Wolchok, et al. (2009) *Guidelines for the Evaluation of Immune Therapy Activity in Solid Tumors: Immune-Related Response Criteria*, Clinical Cancer Research 15(23): 7412-7420.

As used herein, the term "in combination with" refers to the administration of a first agent and second agent to a subject. For purposes of the present invention, one agent (e.g. and IL-10 agent) is considered to be administered in combination with a second agent (e.g. a modulator of an immune checkpoint pathway) if the biological effect resulting from the administration of the first agent persists in the subject at the time of administration of the second agent such that the therapeutic effects of the first agent and second agent overlap. For example, the PD1 immune checkpoint inhibitors (e.g. nivolumab or pembrolizumab) are typically administered by IV infusion every two weeks or every three weeks while agents to be combined with such molecule as contemplated by the present disclosure such as hIL-10 or PEGylated hIL-10 are commonly administered daily subcutaneously. However, the administration of the first agent provides a therapeutic effect over an extended time and the administration of the second agent provides its therapeutic effect while the therapeutic effect of the first agent remains ongoing such that the second agent is considered to be administered in combination with the first agent, even though the first agent may have been administered at a point in time significantly distant (e.g. days or weeks) from the time of administration of the second agent. In one embodiment, one agent (e.g. and IL-10 agent) is considered to be administered in combination with a second agent (e.g. a modulator of an immune checkpoint pathway) if the first and second agents are administered simultaneously (within 30 minutes of each other), contemporaneously or sequentially. In the context of the present invention where the durations of action of the molecules is significantly, a first agent is deemed administered "contemporaneously" with a second agent if first and second agents are administered within about 24 hours of each another, preferably within about 12 hours of each other, preferably within about 6 hours of each other, preferably within about 2 hours of each other, or preferably within about 30 minutes of each other. The term "in combination with" shall also understood to apply to the situation where a first agent (e.g. PEG-IL-10 agent) and a second agent (e.g. a PD1 immune checkpoint inhibitor antagonist antibody) are coformulated in single pharmaceutically acceptable formulation (e.g. a buffered isotonic solution for IV administration) and the coformulation is administered to a subject.

As used herein, the term "in a sufficient amount to effect a change" is used with respect to the quantity of a therapeutic agent(s) to be administered to a subject in need of treatment such that there is a detectable difference between a level of an indicator measured before (e.g., a baseline level) and after administration of a particular therapeutic agent(s). Indicators include any objective parameter (including but not limited to irCR, irRC response criteria, CR, PR, or SD RECIST response criteria) or subjective parameters (e.g., a subject's feeling of well-being).

As used herein, the term "in need of prevention" refers to a determination of a course of treatment with respect to a subject that, in the judgment of a physician, based on the available information accepted in the field for the determination of the likelihood of developing a pathological condition, that a subject requires or will benefit from preventative care.

As used herein, the term "in need of treatment" refers to a determination made by a physician with respect to a subject based on the available information accepted in the field for the identification of a disease, disorder or condition including but not limited to X-ray, CT-scans, conventional laboratory diagnostic tests (e.g. blood count, etc.), genomic data, protein expression data, immunohistochemistry, that the subject requires or will benefit from treatment.

As used herein the term "intratumoral heterogeneity (ITH)" refers to the genetic and phenotypic variation within a tumor, or between individual tumor lesions in the same patient.

As used herein the term "enriched" means that a sample is non-naturally manipulated (e.g., by a scientist) so that a molecule of interest (e.g. a polypeptide) is present in: (a) a greater concentration (e.g., at least 3-fold greater, at least 4-fold greater, at least 8-fold greater, at least 64-fold greater, or more) than the concentration of the molecule of interest in the starting sample, such as a biological sample (e.g., a sample in which the polypeptide naturally occurs or in which it is present after administration), or (b) a concentration greater than the environment in which the molecule of interest was made (e.g., a recombinant bacterial cell).

As used herein, the term "prevent", "preventing", "prevention" and the like refer to a course of action (such as administering IL-10 or a pharmaceutical composition comprising IL-10) initiated in a manner (e.g., prior to the onset of a disease, disorder, condition or symptom thereof) so as to prevent, suppress, inhibit or reduce, either temporarily or permanently, a subject's risk of developing a disease, disorder, condition or the like (as determined by, for example, the absence of clinical symptoms) or delaying the onset thereof, generally in the context of a subject predisposed to having a particular disease, disorder or condition.

As used herein the term "metastasis" describes the spread of cancer cells from the primary tumor to surrounding tissues and to distant organs.

As used herein, the terms "modulate", "modulation" and the like refer to the ability of an agent to effect a response, either positive or negative or directly or indirectly, in a system, including a biological system or biochemical pathway. The term modulator includes both agonists and antagonists.

As used herein the term "Next-Generation Sequencing (NGS)" refers to any of several high-throughput methods of DNA sequencing using the process of massively parallel processing rather than sequencing individual DNA strands.

As used herein, the term "neoplastic disease" refers to disorders or conditions in a subject arising from cellular hyper-proliferation or unregulated (or dysregulated) cell replication. The term neoplastic disease refers to disorders arising from the presence of neoplasms in the subject. Neoplasms may be classified as: (1) benign (2) pre-malignant (or "pre-cancerous"); and (3) malignant (or "cancerous"). Examples benign neoplasms amenable to treatment using the compositions and methods of the present invention include but are not limited to adenomas, fibromas, hemangiomas, and lipomas. Examples of pre-malignant neoplasms amenable to treatment using the compositions and methods of the present invention include but are not limited to hyperplasia, atypia, metaplasia, and dysplasia. Examples of malignant neoplasms amenable to treatment using the compositions and methods of the present invention include but are not limited to carcinomas (cancers arising from epithelial tissues such as the skin or tissues that line internal organs), leukemias, lymphomas, and sarcomas typically derived from bone fat, muscle, blood vessels or connective tissues). The term "neoplastic disease" includes cancers such as breast cancers; sarcomas (including but not limited to osteosarcomas and angiosarcomas), and fibrosarcomas), leukemias, lymphomas, genitourinary cancers (including but not limited to ovarian, urethral, bladder, and prostate cancers); gastrointestinal cancers (including but not limited to colon esophageal and stomach cancers); lung cancers; myelomas; pancreatic cancers; liver cancers; kidney cancers; endocrine cancers; skin cancers; and brain or central and peripheral nervous (CNS) system tumors, malignant or benign, including gliomas and neuroblastomas, astrocytomas, myelodysplastic disorders; cervical carcinoma-in-situ; intestinal polyposes; oral leukoplakias; histiocytoses, hyperprofroliferative scars including keloid scars, hemangiomas; hyperproliferative arterial stenosis, psoriasis, inflammatory arthritis; hyperkeratoses and papulosquamous eruptions including arthritis. Also included are viral induced neoplasms such as warts and EBV induced disease (i.e., infectious mononucleosis), scar formation, hyperproliferative vascular disease including intimal smooth muscle cell hyperplasia, restenosis, and vascular occlusion and the like. The term "neoplastic diseases" include myeloid neoplasms and lymphoid neoplasms. Each category contains different types of hematopoietic cancer with defining morphology, pathobiology, treatment, and/or prognostic features. Correct classification, along with identification of additional factors that may influence prognosis or response to chemotherapy, is essential to allow optimal treatment. Myeloid neoplasms include, but are not limited to, myeloproliferative neoplasms, myeloid and lymphoid disorders with eosinophilia, myeloproliferative/myelodysplastic neoplasms, myelodysplastic syndromes, acute myeloid leukemia and related precursor neoplasms, and acute leukemia of ambiguous lineage. Lymphoid neoplasms include, but are not limited to, precursor lymphoid neoplasms, mature B-cell neoplasms, mature T-cell neoplasms, Hodgkin's Lymphoma, and immunodeficiency-associated lymphoproliferative disorders. Other cancers of the hematopoietic system include, but are not limited to, histiocytic and dendritic cell neoplasms. The term "neoplastic disease" includes neoplastic-related diseases, disorders and conditions referring to conditions that are associated, directly or indirectly, with neoplastic disease, and includes, e.g., angiogenesis and precancerous conditions such as dysplasia.

As used herein the term "oncogene addiction" refers to the phenomenon whereby the survival of cancer cells depends on the continued activity of a mutated oncogene.

As used herein the term "passenger mutation(s)" refers to a mutation(s) that arise during the development of a neoplasm as a result of increased mutation rates, but do not contribute to growth of the neoplasm.

The terms "polypeptide," "peptide," and "protein" are used interchangeably herein, refer to a molecule which is polymeric form of amino acids of any length including those molecules that have been chemically or biochemically modified. A polypeptide may incorporate naturally occurring amino acids, non-naturally occurring amino acids, or derivatized amino acids, and polypeptides having modified polypeptide backbones such as by the incorporation of non-amide linkages. The term polypeptide includes fusion proteins, including, but not limited to, fusion proteins comprised of domains derived from divergent sources, precursor forms of mature proteins having signal peptide leader sequences; polypeptides having N-terminal methionine or N-formyl methionine residues resulting from the direct recombinant expression; fusion proteins of immunologically active proteins (e.g. antigenic diphtheria or tetanus toxin fragments); and the like.

As used herein, the term "proliferative activity" refers a cellular activity that promotes, that is necessary for, or that is specifically associated with, for example, normal cell division, as well as cancer, tumors, dysplasia, cell transformation, metastasis, and angiogenesis.

As used herein the term "reduce or inhibit" is used in reference to the ability of an agent, alone or in combination, to provide a decrease of 20%, 30%, 40%, 50%, 60%, 70%, 75%, 80%, 85%, 90%, 95%, or greater in an observable parameter relative to the pre-existing state prior to the exposure to the agent.

As used herein, the term "response," refers to the change in evaluable parameter including an objective (e.g. biochemical or physiological parameter) or subjective (e.g. feeling of well being) of a cell, tissue, organ, organism, or subject in response to the administration of an agent.

As used herein, the term "Response Evaluation Criteria In Solid Tumors (RECIST)" refers to a set of rules as described in Therasse, et al., (2000) *New guidelines to evaluate the response to treatment in solid tumors* (*RECIST Guidelines*) *J. Natl. Cancer Inst.* 92:205-216 as updated in Eisenhauer, et al., (2009) *New response evaluation criteria in solid tumours: Revised RECIST guideline* (version 1.1) European Journal of Cancer 45(2):228-247.

As used herein the term "RNA sequencing (RNA-Seq)" refers to the use of NGS to determine the sequence of the transcriptome, or complete set of RNA transcripts in a sample.

The term "specifically binds" is used herein to refer to the degree of selectivity or affinity for which one molecule binds to another. In the context of binding pairs (e.g. a ligand/receptor, antibody/antigen, antibody/ligand, antibody/receptor binding pairs) a first molecule of a binding pair is said to specifically bind to a second molecule of a binding pair when the first molecule of the binding pair does not bind in a significant amount to other components present in the sample. A first molecule of a binding pair is said to specifically bind to a second molecule of a binding pair when the affinity of the first molecule for the second molecule is at least two-fold greater, at least ten times greater, at least 20-times greater, or at least 100-times greater than the affinity of the first molecule for other components present in the sample. In a particular embodiment, where the first molecule of the binding pair is an antibody, the antibody specifically binds to the second molecule of the binding pair (e.g. a protein, antigen, ligand, or receptor) if the affinity of the antibody for the second molecule of the binding pair is greater than about $10^9$ liters/mole, alternatively greater than about $10^{10}$ liters/mole, greater than about $10^{11}$ liters/mole, greater than about $10^{12}$ liters/mole as determined by, e.g., Scatchard analysis (Munsen, et al. 1980 Analyt. Biochem. 107:220-239). Specific binding may be assessed using techniques known in the art including but not limited to competition ELISA, BIACORE® assays and/or KINEXA® assays As used herein, the term "small molecules" refers to chemical compounds having a molecular weight that is less than about 10 kDa, less than about 2 kDa, or less than about 1 kDa. Small molecules include, but are not limited to, inorganic molecules, organic molecules, organic molecules containing an inorganic component, molecules comprising a radioactive atom, and synthetic molecules.

As used herein, the term "somatic mutation" refers to a genetic alteration acquired by a cell that can be passed to the progeny of the mutated cell but which was not present in germline DNA (sperm or egg).

As used herein, the term "substantially pure" indicates that a component (e.g., a polypeptide) makes up greater than about 50% of the total content of the composition, and typically greater than about 60% of the total content. More typically, "substantially pure" refers to compositions in which at least 75%, at least 85%, at least 90% or more of the total composition is the component of interest. In some cases, the component of interest will comprise greater than about 90%, or greater than about 95%, or greater than about 99% of the total content of the composition.

As used herein, the term "subject" refers to a human or a non-human mammal. Examples of non-human mammalian species include canine (dog), equine (horse), feline (cat), porcine (pig), bovine (cow). The term "patient" is used interchangeably with the term "subject" herein when the subject is a human being.

As used herein, the term "therapeutically effective amount" refers to the quantity of an agent that, when administered to a subject suffering from a disease, disorder of condition, provides a objective positive effect or subjective positive effect (e.g., a subject's feeling of well-being) on any symptom, aspect, or characteristic of the disease, disorder or condition. Factors which contribute to the determination of a therapeutically effective amount of an agent include but are not limited to readily identifiable indicia such as age, weight, sex, general health, ECOG score, observable physiological parameters (e.g., body temperature, blood pressure, etc.), additional conditions (e.g. diabetes, metabolic syndrome), analysis of the subject (e.g. x-ray, ultrasound, CT-scan, analysis of bodily fluids), biomarkers (such as inflammatory cytokines, IFN-γ, granzyme, and the like). Additional factors which contribute to the determination of a therapeutically effective amount of an agent include but are not limited to the characteristics of the specific disease to be treated including disease type, state of disease progression, tumor burden as well as the therapeutic modality and whether the compositions are being administered in combination with other the co-administration of other agent which may lead to incompatibilities or cross-reactions. A therapeutically effective amount may be adjusted over a course of treatment of a subject in connection with the dosing regimen and/or evaluation of the subject's condition and variations in the foregoing factors. In one embodiment, a therapeutically effective amount is an amount of an agent when used alone or in combination with another agent does not result in non-reversible serious adverse events in the course of administration to a mammalian subject.

As used herein, the term "treat", "treating", treatment" and the like refer to the act of the administering of a composition comprising a agent to a subject wherein said subject is afflicted with a disease, disorder or condition, or a symptom thereof, so as to temporarily, transiently or permanently eliminate, reduce, suppress, mitigate, or ameliorate a cause or at least one symptom of such disease, disorder, or condition but does not necessarily indicate a total elimination of all disorder symptoms afflicting a subject. The term "treat" includes the suspension or slowing the progression of the disease, disorder or condition or inhibiting progression thereof to a harmful or otherwise undesired state.

As used herein the term "tumor mutation burden (TMB)" as used herein refers to the number of somatic mutations present in a tumor sample expressed as the number of mutations per megabase as determined by nucleic acid sequencing wherein at least 0.2 megabase of the nucleic acid in the tumor sample is sequenced, alternatively wherein at least 0.5 megabases of the nucleic acid in the tumor sample is sequenced, alternatively wherein at least 1 megabase of the nucleic acid in the tumor sample is sequenced, or alternatively wherein at least 5 megabases or alternatively wherein at least ten megabases of the nucleic acid in the tumor sample is sequenced. As described in Chalmers, et al. (2017) Genome Medicine 9:34, the accuracy in assessing low tumor mutation burden (low TMB) is improved using the FoundationOne assay (Foundation Medicine, Cambridge MA as described in Frampton, et al. (2013) *Development and validation of a clinical cancer genomic profiling test based on massively parallel DNA sequencing*. Nature Biotechnology 31:1023-31; He, et al. (2016) *Integrated genomic DNA RNA profiling of hematologic malignancies in the clinical setting*. Blood 127:3004-14) with a greater quantity of nucleic acid sequenced, but that the percentage deviation is lower in samples having TMB such that high TMB (defined in this study as >20 mutations per megabase) can be effectively identified by targeted sequencing of only several hundred genes whereas intermediate TMB is improved by the sequence of at least 0.5 Mb sequenced, whereas reliable assessment of low TMB is improved by the sequencing of 5 megabases, alternatively, 10 megabases or more of nucleic acid in the tumor sample. Sequencing to assess TMB may be achieved by any of a variety of art accepted methods including partial genome sequencing, WES or WGS using NGS. Tumor mutation burden may be expressed as the total number of mutations in the genome if essentially entire genome was sequenced in the tumor sample. Tumor mutation burden may also be expressed as the number of mutations per megabase of nucleic acid sequenced in the tumor sample. It is understood that the rate of tumor mutation burden varies among neoplastic diseases so tumor mutation burden should be assessed in the context of a given disease type. For example, certain types of cancers exhibit a wide range of mutation rates from less than 1 mutation per megabase to hundreds per megabase. In general, the term "low tumor mutation burden" means a tumor mutation burden of less than or equal to 15 mutations per megabase sequenced, less than or equal to 10 mutations per megabase sequenced, alternatively less than or equal to 7 mutations per megabase sequenced, alternatively less than or equal to 5 mutations per megabase sequenced, alternatively less than or equal to 2 mutations per megabase sequenced, or alternatively less than or equal to 1 mutation per megabase sequenced. The term "intermediate tumor mutation burden" means a tumor mutation burden of greater than the upper threshold of the level of tumor mutation burden applied to the term low mutation burden in the particular context. In some embodiments, the term intermediate tumor mutation burden is greater than about 15 mutations per megabase sequenced but less than about 100 mutations per megabase sequenced, alternatively greater than about 10 mutations per megabase sequenced but less than 75 mutations per megabase sequenced, alternatively greater than about 5 mutations per megabase sequenced but less than 50 mutations per megabase sequenced, alternatively greater than about 1 mutations per megabase sequenced but less than 30 mutations per megabase sequenced, alternatively greater than about 1 mutation per megabase sequenced but less than 20 mutations per megabase sequenced. The term high tumor mutation is a tumor mutation burden in excess of an intermediate tumor mutation burden greater than or equal to 100 mutations per megabase sequenced, alternatively greater than or equal to 75 mutations per megabase sequenced, alternatively greater than or equal to 50 mutations per megabase sequenced, alternatively greater than or equal to 30 mutations per megabase sequenced, alternatively greater than or equal to 20 mutations per megabase sequenced, or alternatively greater than or equal to 10 mutations per megabase sequenced.

As used herein, "low PD-L1 expression" refers to a level of cell-surface PD-L1 expression of less than 1%; "intermediate PD-L1 expression" refers to a level of cell surface PD-L1 expression of 1% to 49%; and "high PD-L1 expression" refers to a level of cell surface PD-L1 expression of equal to or greater than 50%, where PD-L1 expression is assessed in accordance with the methodologies available in the art, such as in Rizzi et al. (2015) *Science* 348:124-128.

As used herein, the term "variant" refers to naturally-occurring derivatives and non-naturally-occurring derivatives of polypeptides comprising a different amino acid sequences from the parent polypeptide from which the variant is derived. Naturally-occurring variants include homologs (polypeptides and nucleic acids that differ in amino acid or nucleotide sequence, respectively, from one species to another), and allelic variants (polypeptides and nucleic acids that differ in amino acid or nucleotide sequence, respectively, from one individual to another within a species). Non-naturally-occurring variants of a polypeptide that comprise one or more modifications to the amino acid sequence where the change in amino acid sequence is artificially introduced are referred to herein as "muteins." Exemplary IL-10 muteins are described in Eaton, et al. United States Patent Application Publication No. S2015/0038678A1 published Feb. 2, 2015; Hansen, et al. United States Patent Application Publication No. US203/0186386A1 published Oct. 2, 2003 and Van Vlasselaer, et al., United States Patent Application Publication No. US20160068583 A1 published Mar. 10, 2016.

As used herein the term "Whole Exome Sequencing (WES)" refers to a method to determine the DNA sequence of all of the exons within protein-coding genes in a genome.

As used herein the term "Whole Genome Sequencing (WGS)" refers to sequencing to determine the complete DNA sequence of an organism's genome at a single time, typically the somatic cancer genome in oncology studies.

It will be appreciated that throughout this disclosure reference is made to naturally occurring amino acids according to the single letter or three letter codes. For the reader's convenience, the single and three letter amino acid codes are provided in Table 1 below:

TABLE 1

| Amino Acid Abbreviations | | |
|---|---|---|
| G | Glycine | Gly |
| P | Proline | Pro |
| A | Alanine | Ala |
| V | Valine | Val |
| L | Leucine | Leu |
| I | Isoleucine | Ile |
| M | Methionine | Met |
| C | Cysteine | Cys |
| F | Phenylalanine | Phe |
| Y | Tyrosine | Tyr |
| W | Tryptophan | Trp |
| H | Histidine | His |

TABLE 1-continued

| Amino Acid Abbreviations | | |
|---|---|---|
| K | Lysine | Lys |
| R | Arginine | Arg |
| Q | Glutamine | Gln |
| N | Asparagine | Asn |
| E | Glutamic Acid | Glu |
| D | Aspartic Acid | Asp |
| S | Serine | Ser |
| T | Threonine | Thr |

As used herein in the context of the structure of a polypeptide, the terms "N-terminus" (or "amino terminus") and "C-terminus" (or "carboxyl terminus") refer to the extreme amino and carboxyl ends of the polypeptide, respectively, while the terms "N-terminal" and "C-terminal" refer to relative positions in the amino acid sequence of the polypeptide toward the N-terminus and the C-terminus, respectively, and can include the residues at the N-terminus and C-terminus, respectively. "Immediately N-terminal" or "immediately C-terminal" refers to a position of a first amino acid residue relative to a second amino acid residue where the first and second amino acid residues are covalently bound to provide a contiguous amino acid sequence.

In one embodiment, the present invention provides for a method of treatment of neoplastic disease (e.g. cancer) in a mammalian subject by the administration of an IL-10 agent (e.g., PEG-IL-10) in combination with at least one immune checkpoint pathway modulator. As used herein, the term "immune checkpoint pathway modulator" refers to a molecule that inhibits or stimulates the activity of an immune checkpoint pathway in a biological system including an immunocompetent mammal. An immune checkpoint pathway modulator may exert its effect by binding to an immune checkpoint protein (such as those immune checkpoint proteins expressed on the surface of an antigen presenting cell (APC) such as a cancer cell and/or immune T effector cell) or may exert its effect on upstream and/or downstream reactions in the immune checkpoint pathway. For example, an immune checkpoint pathway modulator may modulate the activity of SHP2, a tyrosine phosphatase that is involved in PD-1 and CTLA-4 signaling. The term "immune checkpoint pathway modulators" encompasses both immune checkpoint pathway modulator(s) capable of down-regulating at least partially the function of an inhibitory immune checkpoint (referred to herein as an "immune checkpoint pathway inhibitor" or "immune checkpoint pathway antagonist") and immune checkpoint pathway modulator(s) capable of up-regulating at least partially the function of a stimulatory immune checkpoint (referred to herein as an "immune checkpoint pathway effector" or "immune checkpoint pathway agonist.").

In one embodiment, the immune checkpoint pathway modulator employed in combination with the IL-10 agent is a negative immune checkpoint pathway inhibitor/antagonist. In another embodiment, immune checkpoint pathway modulator employed in combination with the IL-10 agent is a positive immune checkpoint pathway agonist. In another embodiment, immune checkpoint pathway modulator employed in combination with the IL-10 agent is an immune checkpoint pathway antagonist.

Particular embodiments of the present disclosure contemplate the administration of IL-10 agent (e.g., PEG-IL-10) in combination with at least one immune checkpoint pathway modulator plus one or more additional anti-neoplastic agents (e.g., chemotherapeutic agents) or anti-neoplastic treatment modalities (e.g. radiation). The identity of the additional agent(s) will be largely dependent on the nature of the underlying condition being treated (e.g., the addition of an alkylating agent such as cisplatin may be appropriate in the treatment of bladder cancer). Embodiments wherein one or more additional therapeutic or prophylactic agents (e.g., chemotherapeutic agents) are administered in conjunction with the combinations of an IL-10 agent and one or more immune checkpoint pathway inhibitors are described further hereafter.

The term "immune checkpoint pathway" refers to biological response that is triggered by the binding of a first molecule (e.g. a protein such as PD1) that is expressed on an antigen presenting cell (APC) to a second molecule (e.g. a protein such as PDL1) that is expressed on an immune cell (e.g. a T-cell) which modulates the immune response, either through stimulation (e.g. upregulation of T-cell activity) or inhibition (e.g. downregulation of T-cell activity) of the immune response. The molecules that are involved in the formation of the binding pair that modulate the immune response are commonly referred to as "immune checkpoints." The biological responses modulated by such immune checkpoint pathways are mediated by intracellular signaling pathways that lead to downstream immune effector pathways, such as cell activation, cytokine production, cell migration, cytotoxic factor secretion, and antibody production. Immune checkpoint pathways are commonly triggered by the binding of a first cell surface expressed molecule to a second cell surface molecule associated with the immune checkpoint pathway (e.g. binding of PD1 to PDL1, CTLA4 to CD28, etc.). The activation of immune checkpoint pathways can lead to stimulation or inhibition of the immune response.

An immune checkpoint pathway the activation of which results in stimulation of the immune response is referred to herein as a "positive immune checkpoint pathway." The term positive immune checkpoint pathway includes, but is not limited to, biological pathways modulated by the binding of ICOSL to ICOS(CD278), B7-H6 to NKp30, CD155 to CD96, OX40L to OX40, CD70 to CD27, CD40 to CD40L, and GITRL to GITR. Molecules which agonize positive immune checkpoints (such natural or synthetic ligands for a component of the binding pair that stimulates the immune response) are useful to upregulate the immune response. Examples of such positive immune checkpoint agonists include but are not limited to agonist antibodies that bind T-cell activating receptors such as ICOS (such as JTX-2011, Jounce Therapeutics), OX40 (such as MEDI6383, Medimmune or), CD27 (such as varlilumab, Celldex Therapeutics), CD40 (such as dacetuzmumab CP-870,893, Roche, Chi Lob 7/4), HVEM, CD28, CD137 4-1BB, CD226, and GITR (such as MEDI1873, Medimmune; INCAGN1876, Agenus).

An immune checkpoint whose activation results in inhibition or downregulation of the immune response is referred to herein as a "negative immune checkpoint pathway." The inhibition of the immune response resulting from the activation of a negative immune checkpoint diminishes the ability of the host immune system to recognize foreign antigen such as a tumor-associated antigen. The term negative immune checkpoint pathway includes, but is not limited to, biological pathways modulated by the binding of PD1 to PDL1, PD1 to PDL2, and CTLA4 to CDCD80/86. Examples of such negative immune checkpoint antagonists include but are not limited to antagonists (e.g. antagonist antibodies) that bind T-cell inhibitory receptors including but not limited to PD1 (also referred to as CD279), TIM3

(T-cell membrane protein 3; also known as HAVcr2), BTLA (B and T lymphocyte attenuator; also known as CD272), the VISTA (B7-H5) receptor, LAG3 (lymphocyte activation gene 3; also known as CD233) and CTLA4 (cytotoxic T-lymphocyte associated antigen 4; also known as CD152).

The immune response mediated by immune checkpoint pathways is not limited to T cell mediated immune response. For example, the KIR receptors of NK cells modulate the immune response to tumor cells mediated by NK cells. Tumor cells express a molecule called HLA-C, which inhibits the KIR receptors of NK cells leading to a dimunition or the anti-tumor immune response. The administration of an agent that antagonizes the binding of HLA-C to the KIR receptor such an anti-KIR3 mab (e.g. lirilumab, BMS) inhibits the ability of HLA-C to bind the NK cell inhibitory receptor (KIR) thereby restoring the ability of NK cells to detect and attack cancer cells. Thus, the immune response mediated by the binding of HLA-C to the KIR receptor is an example a negative immune checkpoint pathway the inhibition of which results in the activation of a of non-T-cell mediated immune response.

As previously discussed, "negative immune checkpoint pathway inhibitor" refers to an immune checkpoint pathway modulator that interferes with the activation of a negative immune checkpoint pathway resulting in the upregulation or enhancement of the immune response. Exemplary negative immune checkpoint pathway inhibitors include but are not limited to programmed death-1 (PD1) pathway inhibitors, programed death ligand-1 (PDL1) pathway inhibitors, TIM3 pathway inhibitors and anti-cytotoxic T-lymphocyte antigen 4 (CTLA4) pathway inhibitors.

In one embodiment, the immune checkpoint pathway modulator is an antagonist of a negative immune checkpoint pathway that inhibits the binding of PD1 to PDL1 and/or PDL2 ("PD1 pathway inhibitor"). PD1 pathway inhibitors result in the stimulation of a range of favorable immune response such as reversal of T cell exhaustion, restoration cytokine production, and expansion of antigen-dependent T cells. PD1 pathway inhibitors have been recognized as effective variety of cancers receiving approval from the USFDA for the treatment of variety of cancers including melanoma, lung cancer, kidney cancer, Hodgkins lymphoma, head and neck cancer, bladder cancer and urothelial cancer.

The term PD1 pathway inhibitors includes monoclonal antibodies that interfere with the binding of PD1 to PDL1 and/or PDL2. Antibody PD1 pathway inhibitors are well known in the art. Examples of commercially available PD1 pathway inhibitors that monoclonal antibodies that interfere with the binding of PD1 to PDL1 and/or PDL2 include nivolumab (Opdivo®, BMS-936558, MDX1106, commercially available from BristolMyers Squibb, Princeton NJ), pembrolizumab (Keytruda® MK-3475, lambrolizumab, commercially available from Merck and Company, Kenilworth NJ), and atezolizumab (Tecentriq®, Genentech/Roche, South San Francisco CA). Additional PD1 pathway inhibitors antibodies are in clinical development including but not limited to durvalumab (MEDI4736, Medimmune/AstraZeneca), pidilizumab (CT-011, CureTech), PDR001 (Novartis), BMS-936559 (MDX1105, BristolMyers Squibb), and avelumab (MSB0010718C, Merck Serono/Pfizer) and SHR-1210 (Incyte). Additional antibody PD1 pathway inhibitors are described in U.S. Pat. No. 8,217,149 (Genentech, Inc) issued Jul. 10, 2012; U.S. Pat. No. 8,168,757 (Merck Sharp and Dohme Corp.) issued May 1, 2012, U.S. Pat. No. 8,008,449 (Medarex) issued Aug. 30, 2011, U.S. Pat. No. 7,943,743 (Medarex, Inc) issued May 17, 2011.

In one embodiment of the invention, the PD1 immune checkpoint pathway modulator is an antibody comprising the CDR sequences provided in Table 2 below:

TABLE 2

| CDR Sequences | | |
|---|---|---|
| Name | Amino Acid Sequence | SEQ ID NO |
| CDR-L1 | GGNSIGSYSVH | SEQ ID NO 1 |
| CDR-L2 | DDSDRPS | SEQ ID NO 2 |
| CDR-L3 | QVWDTSSYWV | SEQ ID NO 3 |
| CDR-H1 | GFTFSSYAMS | SEQ ID NO 4 |
| CDR-H2 | DISGGGGTTYYADSVKG | SEQ ID NO 5 |
| CDR-H3 | SGTVVTDFDY | SEQ ID NO 6 |

The terms "complementary determining region" and its abbreviation "CDR" are those sequences typically provided in immunoglobulin molecules that determine the binding properties used herein to refer to the hypervariable domains of variable domains of immunoglobulins. Systematic identification of residues included in the CDRs have been developed by Kabat (Kabat et al., 1991, Sequences of Proteins of Immunological Interest, 5th Ed., United States Public Health Service, National Institutes of Health, Bethesda). The numbering of the CDR positions herein is provided according to Kabat numbering conventions.

In one embodiment of the invention, the PD1 immune checkpoint pathway inhibitor is an antibody comprising the variable domain sequences (SEQ ID NO: 7 and SEQ ID NO: 8) provided in Table 3 below:

TABLE 3

| Variable Domain Sequences | | |
|---|---|---|
| Name | Amino Acid Sequence | SEQ ID NO |
| VL-09 | SYVLTQPPSVSVAPGQTARVTCGGNSIGSYSVHWYQQ KPGQAPVLVVYDDSDRPSGIPERFSGSNSGNTAALTIS RVEAGDEADYYCQVWDTSSWVFGGGTKLTVL | SEQ ID NO 7 |
| VH-09 | EVQLLESGGGLVQPGGSLRLSCPASGFTFSSYAMSWV RQAPGKGLGWVSDISGGGGTTYYADSVKGRFTISRDN SKNTLYLQMNSLRGEDTAVYYCAKSGTVVTDFDW GQGTLVTVSS | SEQ ID NO 8 |

In one embodiment of the invention, the PD1-antagonist antibody is AM0001: a monoclonal antibody with a lambda 2 light chain and an IgG4 with a serine to proline substitution at position 228 (S228P) to provide a "hinge-stabilized" heavy chain, characterized by VL and VH CDRs having amino acid sequences corresponding to SEQ ID NOS: 1-6 as set out in Table 2 hereinabove, a light chain variable region characterized by the sequence of SEQ ID NO: 7 and a heavy chain variable region characterized by the amino acid sequence of SEQ ID NO:8. The AM0001 antibody is characterized as having a binding affinity ($K_d$) for human and cynomologous monkey PD-1 of about 10 pM or less at 25° C. The binding affinity of AM0001, measured by bio-layer interferometry (BLI), are shown in Table 4 below.

TABLE 4

PD-1 Binding Affinitie AM0001

| Antibody | $K_D$(M) | $K_{on}$ | $K_{dis}$ | $R^2$ |
|---|---|---|---|---|
| AM0001 | <1.0E−12 | 6.655E+5 | <1.0E−7 | 0.9989 |

The full length amino acid sequences of the heavy chain and light chain of AM0001 are provided below.

```
AM0001 Mature Heavy Chain Protein Sequence
(Human IgG4 S228P Framework):
                                   (SEQ ID NO: 11)
EVQLLESGGGLVQPGGSLRLSCPASGFTFSSYAMSWVRQAPGKGLGW

VSDISGGGGTTYYADSVKGRFTISRDNSKNTLYLQMNSLRGEDTAVYY

CAKSGTVVTDFDWGQGTLVTVSSASTKGPSVFPLAPCSRSTSESTAA

LGCLVKDYFPEPVTVSWNSGALTSGVHTFPAVLQSSGLYSLSSVVTVP

SSSLGTKTYTCNVDHKPSNTKVDKRVESKYGPPCPPCPAPEFLGGPSVF

LFPPKPKDTLMISRTPEVTCVVVDVSQEDPEVQFNWYVDGVEVHNAK

TKPREEQFNSTYRVVSVLTVLHQDWLNGKEYKCKVSNKGLPSSIEKTI

SKAKGQPREPQVYTLPPSQEEMTKNQVSLTCLVKGFYPSDIAVEWESN

GQPENNYKTTPPVLDSDGSFFLYSRLTVDKSRWQEGNVFSCSVMHEAL

HNHYTQKSLSLSLGK
```

```
AM0001 Mature Light Chain Protein Sequence
(Human Lambda-2 Framework):
                                   (SEQ ID NO: 12)
SYVLTQPPSVSVAPGQTARVTCGGNSIGSYSVHWYQQKPGQAPVLVV

YDDSDRPSGIPERFSGSNSGNTAALTISRVEAGDEADYYCQVWDTSSY

WVFGGGTKLTVLGQPKAAPSVTLFPPSSEELQANKATLVCLISDFYPG

AVTVAWKADSSPVKAGVETTTPSKQSNNKYAASSYLSLTPEQWKSHR

SYSCQVTHEGSTVEKTVAPTECS
```

The PD-1 pathway inhibitor antibody may be produced by recombinant means. The present invention includes nucleic acid sequences encoding the amino acid sequences of SEQ ID NO. 1, SEQ ID NO. 2, SEQ ID NO. 3, SEQ ID NO. 4, SEQ ID NO. 5, SEQ ID NO. 6, SEQ ID NO. 7, SEQ ID NO. 8, SEQ ID NO. 11, and SEQ ID NO. 12. In one embodiment, the present disclosure provides nucleic acid sequences when the PD1-antagonist antibody is AM0001, the nucleic acid sequences encoding the heavy and light chains of AM0001 (SEQ ID NO. 11 and SEQ ID NO. 12) are as set out below as SEQ ID NO. 13, and SEQ ID NO. 14, respectively.

```
AM0001 Mature Heavy Chain DNA Sequence
(Human IgG4 S228P Framework):
                                   (SEQ ID NO: 13)
GAGGTCCAGCTCCTGGAATCCGGGGGCGGTCTGGTCCAGCCGGGC

GGCTCGCTCCGCCTGTCCTGCCCGGCGAGCGGCTTCACCTTCTCCT

CCTACGCCATGTCCTGGGTGAGGCAGGCCCCCGGCAAGGGCCTCG

GCTGGGTCAGCGACATCTCCGGCGGCGGCGGCACCACGTACTACG

CGGACTCGGTGAAGGGCCGGTTCACGATCTCCCGGGACAACTCCA

AGAACACCCTGTACCTGCAGATGAACTCACTGCGGGGCGAGGACA

CGGCGGTGTATTACTGCGCCAAGTCCGGAACGGTTGTGACTGATTT

CGACTACTGGGGCCAGGGCACCCTGGTGACCGTGTCCAGCGCCTCC

ACCAAGGGCCCCAGCGTGTTCCCCCTGGCGCCGTGCTCGCGGAGC

ACCAGCGAGTCCACCGCCGCGCTCGGTTGCCTCGTCAAGGACTACT

TCCCCGAGCCGGTCACAGTGTCATGGAACTCCGGCGCGCTGACGA

GCGGCGTGCACACCTTCCCGGCCGTGCTCCAGTCCAGCGGCCTGTA

CAGCCTCAGTAGCGTCGTGACGGTGCCCTCGTCGTCGCTGGGCACG

AAGACCTACACCTGCAACGTGGACCACAAGCCGTCCAACACCAAG

GTCGATAAGCGAGTGGAGAGCAAGTACGGCCCCCCGTGCCCCCCC

TGCCCGGCCCCGGAGTTCCTGGGTGGCCCCTCCGTGTTCCTCTTCCC

CCCGAAGCCCAAAGACACCCTCATGATCAGCCGGACGCCGGAGGT

CACGTGCGTCGTCGTGGACGTGAGCCAGGAAGACCCGGAGGTCCA

GTTCAACTGGTACGTGGACGGCGTCGAGGTGCATAACGCCAAGAC

CAAGCCTCGCGAGGAACAGTTCAACTCCACTTACCGCGTCGTGTCC

GTCCTCACCGTCCTGCACCAGGACTGGCTCAACGGGAAGGAATAC

AAGTGCAAGGTCTCGAACAAGGGCCTGCCGTCGTCCATCGAGAAG

ACCATCAGCAAGGCCAAGGGCCAGCCGCGGGAGCCCCAGGTCTAC

ACCCTCCCCCCCTCCCAGGAAGAGATGACGAAGAACCAGGTGAGC

CTGACGTGCCTCGTGAAGGGGTTCTACCCCTCCGACATCGCAGTCG

AGTGGGAGAGCAACGGCCAGCCGGAGAACAACTACAAGACGACC

CCCCCGGTGCTGGACAGCGACGGGTCCTTCTTCCTCTACTCGCGTC

TCACAGTCGACAAGTCGCGCTGGCAGGAGGGCAACGTCTTCTCGT

GCTCCGTGATGCACGAGGCCCTGCACAACCACTACACCCAGAAGT

CGCTGTCCCTGTCCCTGGGCAAG
```

```
AM0001 Mature Light Chain Protein Sequence
(Human Lambda-2 Framework):
                                   (SEQ ID NO: 14)
AGCTACGTGCTGACCCAGCCGCCCTCGGTGTCGGTCGCCCCGGGCC

AGACGGCACGTGTGACCTGCGGCGGTAACAGCATCGGCTCCTACT

CGGTCCACTGGTATCAGCAGAAGCCGGGGCAGGCCCCGGTCCTGG

TGGTCTACGACGACAGCGACCGCCCGTCCGGCATCCCCGAACGCTT

CAGCGGCTCAAACAGCGGGAACACCGCGGCCCTGACGATCTCGCG

CGTCGAGGCGGGGGACGAAGCCGATTACTACTGCCAGGTCTGGGA

CACCTCGAGTTACTGGGTGTTCGGCGGGGGCACGAAGCTGACCGT

CCTCGGCCAGCCGAAGGCCGCCCCCTCAGTAACCCTGTTCCCCCCG
```

-continued

TCCTCGGAGGAGTTGCAGGCGAACAAGGCGACGCTGGTGTGCTTG

ATCTCGGACTTCTACCCCGGAGCGGTGACGGTCGCCTGGAAGGCC

GACTCCTCCCCGGTCAAGGCGGGCGTGGAGACGACCACCCCCTCC

AAGCAGAGCAACAACAAGTACGCCGCCTCGAGCTACCTCTCGCTG

ACACCCGAGCAGTGGAAGTCCCACCGGTCCTACTCGTGCCAGGTA

ACCCACGAGGGCTCCACCGTCGAGAAGACCGTGGCCCCCACCGAG

TGCAGC

The term PD1 pathway inhibitors are not limited to antagonist antibodies. Non-antibody biologic PD1 pathway inhibitors are also under clinical development including AMP-224, a PD-L2 IgG2a fusion protein, and AMP-514, a PDL2 fusion protein, are under clinical development by Amplimmune and Glaxo SmithKline. Aptamer compounds are also described in the literature useful as PD1 pathway inhibitors (Wang, et al. Selection of PD1/PD-L1 X-Aptamers, Biochimie, in press; available online 11 Sep. 2017, at the internet address: https://doi.org/10.1016/j.biochi.2017.09.006.

The term PD1 pathway inhibitors includes peptidyl PD1 pathway inhibitors such as those described in Sasikumar, et al., U.S. Pat. No. 9,422,339 issued Aug. 23, 2016, and Sasilkumar, et al., U.S. Pat. No. 8,907,053 issued Dec. 9, 2014. CA-170 (AUPM-170, Aurigene/Curis) is reportedly an orally bioavailable small molecule targeting the immune checkpoints PDL1 and VISTA. Pottayil Sasikumar, et al. *Oral immune checkpoint antagonists targeting PD-L1/VISTA or PD-L1/Tim3for cancer therapy*. [abstract]. In: Proceedings of the 107th Annual Meeting of the American Association for Cancer Research; 2016 Apr. 16-20; New Orleans, LA. Philadelphia (PA): AACR; Cancer Res 2016; 76(14 Suppl): Abstract No. 4861. CA-327 (AUPM-327, Aurigene/Curis) is reportedly an orally available, small molecule that inhibit the immune checkpoints, Programmed Death Ligand-1 (PDL1) and T-cell immunoglobulin and mucin domain containing protein-3 (TIM3).

The term PD1 pathway inhibitors includes small molecule PD1 pathway inhibitors. Examples of small molecule PD1 pathway inhibitors useful in the practice of the present invention are described in the art including Sasikumar, et al 1,2,4-*oxadiazole and thiadiazole compounds as immunomodulators* (PCT/IB2016/051266 filed Mar. 7, 2016, published as WO2016142833A1 Sep. 15, 2016) and Sasikumar, et al. 3-*substituted*-1,2,4-*oxadiazole and thiadiazole compounds as immunomodulators* (PCT application serial number PCT/IB2016/051343 filed Mar. 9, 2016 and published as WO2016142886A2), BMS-1166 and BMS-1001 (Skalniak, et al (2017) Oncotarget 8(42): 72167-72181) having the structures:

BMS-1001

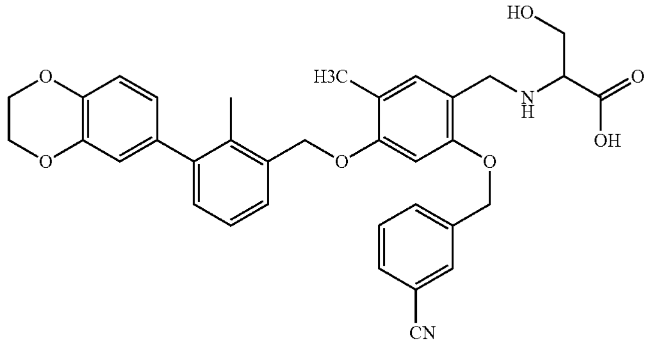

and

BMS-1166

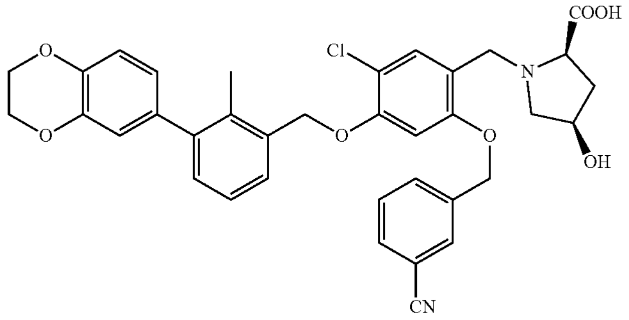

Chupak L S amd Zheng X. *Compounds useful as immunomodulators*. Bristol-Myers Squibb Co. 2015 WO 2015/034820 A1, EP3041822 B1 granted Aug. 9, 2017; WO2015034820 A1; and Chupak, eta. *Compounds useful as immunomodulators*. Bristol-Myers Squibb Co. 2015 WO 2015/160641 A2. WO 2015/160641 A2, Chupak, et al. *Compounds useful as immunomodulators*. Bristol-Myers Squibb Co. Sharpe, et al. Modulators of immunoinhibitory receptor PD-1, and methods of use thereof, WO 2011082400 A2 published Jul. 7, 2011; U.S. Pat. No. 7,488,802 (Wyeth) issued Feb. 10, 2009.

In one embodiment, the immune checkpoint pathway modulator is an antagonist of a negative immune checkpoint pathway that inhibits the binding of CTLA4 to CD28 ("CTLA4 pathway inhibitor"). The immune checkpoint receptor CTLA4 belongs to the immunoglobulin superfamily of receptors, which also includes PD1; BTLA; lymphocyte attenuator; TIM3, and V-domain immunoglobulin suppressor of T cell activation. CD80 (also known as B7.1) and CD86 (also known as B7.2) have been identified as the CTLA4 receptor ligands. CTLA4, the first immune checkpoint receptor to be clinically targeted, is expressed exclusively on T cells, where it primarily regulates the amplitude of the early stages of T cell activation. It has been shown to counteract the activity of the T cell co-stimulatory receptor CD28.

Upon antigen recognition, CD28 signaling strongly amplifies T-cell receptor signaling to activate T cells. See, e.g., Riley et al., (2002) Proc. Natl Acad. Sci. USA 99:11790-95. CTLA4 is transcriptionally induced following T cell activation. Although CTLA4 is expressed by activated CD8+ effector T cells, its primary physiological role is believed to be manifested through distinct effects on the two major subsets of CD4+ T cells: i) down-modulation of helper T cell activity, and ii) enhancement of regulatory T cell immunosuppressive activity. Specifically, CTLA4 blockade results in immune response enhancement dependent on helper T cells, while CTLA4 engagement of regulatory T cells increases their suppressive function. See, e.g., Fontenot et al., (2003) Nat. Immunol. Proc. 4:330-36. Examples of CTLA4 pathway inhibitor are well known in the art (See, e.g., U.S. Pat. No. 6,682,736 (Abgenix) issued Jan. 27, 2004; U.S. Pat. No. 6,984,720 (Medarex, Inc.) issued May 29, 2007; U.S. Pat. No. 7,605,238 (Medarex, Inc.) issued Oct. 20, 2009).

Currently CTLA4 pathway inhibitor antibody treatment approaches are not without shortcomings. By way of example, treatment of metastatic melanomas with a humanized anti-CTLA4 antagonistic antibody has been reported to cause certain autoimmune toxicities (e.g., bowel inflammation and dermatitis), prompting the determination of a tolerated therapeutic window (Wu et al., (2012) Int. J. Biol. Sci. 8:1420-30). The enhanced therapeutic efficacy of the combination of an CTLA4 pathway inhibitor (e.g., an antibody such as ipilimumab) with IL-10 agent (e.g., PEG-IL-10) offers the potential of reducing dosages while maintaining therapeutic efficacy.

In one embodiment, the immune checkpoint pathway modulator is an antagonist of a negative immune checkpoint pathway that inhibits the binding of BTLA to HVEM ("BTLA pathway inhibitor") BTLA is a co-inhibitory molecule structurally and functionally related to CTLA-4 and PD-1. Although BTLA is expressed on virus-specific human CD8+ T cells, it is progressively downregulated after their differentiation from a naive to effector phenotype (Paulos et al., (January 2010) J. Clin. Invest. 120(1):76-80). The herpes virus entry mediator (HVEM; also known as TNFRSF14), which is expressed on certain tumor cell types (e.g., melanoma) and tumor-associated endothelial cells, has been identified as the BTLA ligand. Because the interactions between BTLA and HVEM are complex, therapeutic inhibition strategies are less straightforward for BTLA than they are for other immune checkpoint pathway inhibitory receptors and ligands. Pardoll, (2012) Nature Rev. Cancer 12:252-64. A number of approaches targeting the BTLA/HVEM pathway using anti-BTLA antibodies and antagonistic HVEM-Ig have been evaluated, and such approaches have suggested promising utility in a number of diseases, disorders and conditions, including transplantation, infection, tumor, and autoimmune disease (Wu et al., (2012) Int. J. Biol. Sci. 8:1420-30).

In one embodiment, the immune checkpoint pathway modulator is an antagonist of a negative immune checkpoint pathway that inhibits the ability of TIM3 to bind to TIM3-activating ligands ("TIM3 pathway inhibitor"). TIM3 inhibits T helper 1 (TH1) cell responses, and anti-TIM3 antibodies have been shown to enhance antitumor immunity. Galectin 9, a molecule involved in the modulation of the TIM3 pathway, is upregulated in various types of cancer, including breast cancer. TIM3 has been reported to be co-expressed with PD1 on tumor-specific CD8+ T cells. When stimulated by the cancer-testes antigen NY-ESO-1, dual inhibition of both molecules significantly enhances the in vitro proliferation and cytokine production of human T cells. Moreover, in animal models, coordinated blockage of PD1 and TIM3 was reported to enhance antitumor immune responses in circumstances in which only modest effects from blockade of each individual molecule were observed. See, e.g., Pardoll, (2012) Nature Rev. Cancer 12:252-64; Zhu et al., (2005) Nature Immunol. 6:1245-52; Ngiow et al., (2011) Cancer Res. 71:3540-51). Examples of TIM3 pathway inhibitors are known in the art and with representative non-limiting examples described in United States Patent Publication No. PCT/US2016/021005 published Sep. 15, 2016; Lifke, et al. United States Patent Publication No. US 20160257749 A1 published Sep. 8, 2016 (F. Hoffman-LaRoche), Karunsky, U.S. Pat. No. 9,631,026 issued Apr. 27, 2017; Karunsky, Sabatos-Peyton, et al. U.S. Pat. No. 8,841,418 issued Sep. 23, 2014; U.S. Pat. No. 9,605,070; and Takayanagi, et al. U.S. Pat. No. 8,552,156 issued Oct. 8, 2013.

LAG3 has been shown to play a role in enhancing the function of Regulatory T ($T_{Reg}$) cells, and independently in inhibiting CD8+ effector T cell functions. MHC class II molecules, the ligand for LAG3, are upregulated on some epithelial cancers (often in response to IFNγ), and are also expressed on tumor-infiltrating macrophages and dendritic cells. Though the role of the LAG3-MHC class II interaction has not been definitively elucidated, the interaction can be a key component in the role of LAG3 in enhancing $T_{Reg}$ cell function.

LAG3 is one of several immune checkpoint receptors that are coordinately upregulated on both $T_{Reg}$ cells and anergic T cells. Simultaneous blockade of LAG3 and PD1 can cause enhanced reversal of the anergic state when compared to blockade of one receptor alone. Indeed, blockade of LAG3 and PD1 has been shown to synergistically reverse anergy among tumor-specific CD8+ T cells and virus-specific CD8+ T cells in the setting of chronic infection. IMN/P321 (ImmuFact) is being evaluated in melanoma, breast cancer, and renal cell carcinoma. See generally Woo et al., (2012) Cancer Res 72:917-27; Goldberg et al., (2011) Curr. Top. Microbiol. Immunol. 344:269-78; Pardoll, (2012) Nature Rev. Cancer 12:252-64; Grosso et al., (2007) J. Clin. Invest. 117:3383-392.

A2aR inhibits T cell responses by stimulating CD4+ T cells towards developing into $T_{Reg}$ cells. A2aR is particularly important in tumor immunity because the rate of cell death in tumors from cell turnover is high, and dying cells release adenosine, which is the ligand for A2aR. In addition, deletion of A2aR has been associated with enhanced and sometimes pathological inflammatory responses to infection. Inhibition of A2aR can be effected by antibodies that block adenosine binding or by adenosine analogs. Such agents can be useful in disorders such as cancer and Parkinson's disease. See generally, Zarek et al., (2008) Blood 111:251-59; Waickman et al., (25 Nov. 2011) Cancer Immunol. Immunother. (doi: 10. 1007/s00262-011-1155-7)].

IDO (Indoleamine 2,3-dioxygenase) is an immune regulatory enzyme that is normally expressed in tumor cells and in activated immune cells. IDO down-regulates the immune response mediated through oxidation of tryptophan. This results in inhibition of T-cell activation and induction of T-cell apoptosis, creating an environment in which tumor-specific cytotoxic T lymphocytes are rendered functionally inactive or are no longer able to attack a subject's cancer cells. Indoximod (NewLink Genetics) is an IDO inhibitor being evaluated in metastatic breast cancer.

Production, purification, and fragmentation of polyclonal and monoclonal antibodies are described (e.g., Harlow and Lane (1999) Using Antibodies, Cold Spring Harbor Laboratory Press, Cold Spring Harbor, NY); standard techniques for characterizing ligand/receptor interactions are available (see, e.g., Coligan et al. (2001) Current Protocols in Immunology, Vol. 4, John Wiley, Inc., NY); methods for flow cytometry, including fluorescence-activated cell sorting (FACS), are available (see, e.g., Shapiro (2003) Practical Flow Cytometry, John Wiley and Sons, Hoboken, NJ); and fluorescent reagents suitable for modifying nucleic acids, including nucleic acid primers and probes, polypeptides, and antibodies, for use, for example, as diagnostic reagents, are available (Molecular Probes (2003) Catalogue, Molecular Probes, Inc., Eugene, OR.; Sigma-Aldrich (2003) Catalog, St. Louis, MO.).

As previously described, the present invention provides for a method of treatment of neoplastic disease (e.g. cancer) in a mammalian subject by the administration of an IL-10 agent (e.g., PEG-IL-10) in combination with an agent(s) that modulate at least one immune checkpoint pathway including immune checkpoint pathway modulators that modulate two, three or more immune checkpoint pathways.

In one embodiment, multiple immune checkpoint pathways may be modulated by the administration of multi-functional molecules which are capable of acting as modulators of multiple immune checkpoint pathways. Examples of such multi-immune checkpoint pathway modulators include but are not limited to bi-specific or poly-specific antibodies. Examples of poly-specific antibodies capable of acting as modulators or multiple immune checkpoint pathways are known in the art. For example, United States Patent Publication No. 2013/0156774 describes bispecific and multispecific agents (e.g., antibodies), and methods of their use, for targeting cells that co-express PD1 and TIM3. Moreover, dual blockade of BTLA and PD1 has been shown to enhance antitumor immunity (Pardoll, (2012) Nature Rev. Cancer 12:252-64). The present disclosure contemplates the use of IL-10 agents in combination with immune checkpoint pathway modulators that target multiple immune checkpoint pathways, including but limited to bi-specific antibodies which bind to both PD1 and LAG3. Thus, antitumor immunity can be enhanced at multiple levels, and combinatorial strategies can be generated in view of various mechanistic considerations.

Other embodiments contemplate the administration of an IL-10 agent in combination with multiple checkpoint pathway modulators, and still further embodiments contemplate the administration of an IL-10 agent in combination with three or more immune checkpoint pathway modulators. Such combinations of IL-10 agents with multiple immune checkpoint pathway modulators can be advantageous in that immune checkpoint pathways may have distinct mechanisms of action, which provides the opportunity to attack the underlying disease, disorder or conditions from multiple distinct therapeutic angles. Representative combinations (some of which are in clinical trials as identified below) of immune checkpoint pathway modulators that may be combined with the administration of an IL-10 agent include but are not limited to:

(a) PD1/PDL1 pathway inhibitors (including but not limited to nivolumab, pembrolizumab, PDR001; MEDI4736, atezolizumab, and durvalumab) with LAG3 antagonist antibodies (e.g. BMS-986016, clinical trial identifier NCT01968109), CTLA4 antagonist antibodies (e.g. ipilumumab), B7-H3 antagonist antibodies (e.g. enoblituzumab, e.g. clinical trial identifier NCT01968109), KIR antagonist antibodies (e.g. lirilumab, e.g. clinical trial identifier NCT01714739);

(b) PD1/PDL1 pathway inhibitors (including but not limited to nivolumab, pembrolizumab, PDR001; MEDI4736, atezolizumab, and durvalumab) with positive immune checkpoint agonist antibodies such as agonist antibodies to 4-1BB (relumab, clinical trial identifier NCT02253992), agonist antibodies to ICOS (e.g. JTX-2011, e.g. clinical trial identifier NCT02904226), agonist antibodies to CD27 (e.g., varlilumab, e.g., clinical trial identifier NCT02335918), agonist antibodies to GITR (e.g., GWN323, e.g., clinical trial identier NCT02740270), and agonist antibodies to OX40 (e.g., MEDI6383, (e.g., clinical trial identier NCT02221960).

(c) CTLA4 pathway inhibitors (including but not limited to ipilumuab) with LAG3 antagonist antibodies (e.g. BMS-986016); TIM3 antagonist antibodies.

Other representative combination therapies with PD1/PDL1 pathway inhibitors that may be supplemented by the additional of an IL-10 agent include the combination PD1/PDL1 pathway inhibitors with BRAF/MEK inhibitors, kinase inhibitors such as sunitinib (NCT02484404), PARP inhibitors such as olaparib (NCT02484404) EGFR inhibitors such as osimertinib (Ahn, et al. (2016) J Thorac Oncol. 11:S115), IDO inhibitors such as epacadostat, and oncolytic viruses such as talimogene laherparepvec (T-VEC). Other representative combination therapies with CTL4 pathway inhibitors that may be supplemented by the additional of an IL-10 agent include the combination CTL4 pathway inhibitors with IL2, GMCSF and IFN-α.

IL-10 Agents:

As used herein, the term "IL-10 agent" refers to a dimeric molecule having IL-10 activity comprising two IL-10 polypeptides that bind to the IL-10 receptor and modulate the same signaling pathway as IL-10 and are capable of eliciting a biological response characteristic of IL-10. The term IL-10 agent includes IL-10 analogs and IL-10 variants and modified IL-10 agents.

The term IL-10 polypeptide is to be broadly construed and include, for example, human and non-human IL-10 related polypeptides, including homologs, variants (including muteins), and fragments thereof, as well as IL-10 polypeptides having, for example, a leader sequence (e.g., the signal peptide), and modified versions of the foregoing. In further particular embodiments, IL-10, IL-10 polypeptide(s), and IL-10 agent(s) are agonists. The term "IL-10 analog" as used herein refers to IL-10 agents that operate through the IL-10 agents include IL-10 analogs and IL-10 variants that operate through the same mechanism of action as IL-10 (i.e., that specifically bind to and modulate the activity of the IL-10 receptor and agents that modulate the same signaling pathway as IL-10 in a manner analogous thereto) and are capable of eliciting a biological response comparable to (or greater than) that of IL-10.

The term "IL10 polypeptide" includes IL-10 polypeptides comprising conservative amino acid substitutions. The term "conservative amino acid substitution" refers to substitutions that preserve the activity of the protein by replacing an amino acid(s) in the protein with an amino acid with a side chain of similar acidity, basicity, charge, polarity, or size of the side chain. Conservative amino acid substitutions generally entail substitution of amino acid residues within the following groups: 1) L, I, M, V, F; 2)R, K; 3) F, Y, H, W, R; 4) G, A, T, S; 5) Q, N; and 6) D, E. Guidance for substitutions, insertions, or deletions can be based on alignments of amino acid sequences of different variant proteins or proteins from different species. Thus, in addition to any naturally-occurring IL-10 polypeptide, the present disclosure contemplates having 1, 2, 3, 4, 5, 6, 7, 8, 9, or 10 usually no more than 20, 10, or 5 amino acid substitutions, where the substitution is usually a conservative amino acid substitution.

In some cases, the IL-10 polypeptide includes one or more linkages other than peptide bonds, e.g., at least two adjacent amino acids are joined via a linkage other than an amide bond to reduce or eliminate undesired proteolysis or other means of degradation, and/or to increase serum stability, and/or to restrict or increase conformational flexibility, one or more amide bonds within the backbone of IL-10 can be substituted. One or more amide linkages (—CO—NH—) in an IL-10 polypeptide can be replaced with a linkage which is an isostere of an amide linkage, such as —CH2NH—, —CH2S—, —CH2CH2-, —CH═CH-(cis and trans), —COCH2-, —CH(OH)$CH_2$— or —$CH_2$SO—. One or more amide linkages in IL-10 can also be replaced by, for example, a reduced isostere pseudopeptide bond. See Couder et al. (1993) Int. J. Peptide Protein Res. 41:181-184. Such replacements and how to effect them are known to those of ordinary skill in the art.

The term "IL10 polypeptide" includes IL-10 polypeptides comprising one or more amino acid substitutions including but not limited to: a) substitution of alkyl-substituted hydrophobic amino acids, including alanine, leucine, isoleucine, valine, norleucine, (S)-2-aminobutyric acid, (S)-cyclohexylalanine or other simple α-amino acids substituted by an aliphatic side chain from $C_1$-$C_{10}$ carbons including branched, cyclic and straight chain alkyl, alkenyl or alkynyl substitutions;

b) substitution of aromatic-substituted hydrophobic amino acids, including phenylalanine, tryptophan, tyrosine, sulfotyrosine, biphenylalanine, 1-naphthylalanine, 2-naphthylalanine, 2-benzothienylalanine, 3-benzothienylalanine, histidine, including amino, alkylamino, dialkylamino, aza, halogenated (fluoro, chloro, bromo, or iodo) or alkoxy (from $C_1$-$C_4$)-substituted forms of the above-listed aromatic amino acids, illustrative examples of which are: 2-, 3- or 4-aminophenylalanine, 2-, 3- or 4-chlorophenylalanine, 2-, 3- or 4-methylphenylalanine, 2-, 3- or 4-methoxyphenylalanine, 5-amino-, 5-chloro-, 5-methyl- or 5-methoxytryptophan, 2'-, 3'-, or 4'-amino-, 2'-, 3'-, or 4'-chloro-, 2, 3, or 4-biphenylalanine, 2'-, 3'-, or 4'-methyl-, 2-, 3- or 4-biphenylalanine, and 2- or 3-pyridylalanine; c) substitution of amino acids containing basic side chains, including arginine, lysine, histidine, ornithine, 2,3-diaminopropionic acid, homoarginine, including alkyl, alkenyl, or aryl-substituted (from $C_1$-$C_{10}$ branched, linear, or cyclic) derivatives of the previous amino acids, whether the substituent is on the heteroatoms (such as the α-nitrogen, or the distal nitrogen or nitrogens, or on the α-carbon, in the pro-R position for example. Compounds that serve as illustrative examples include: N-epsilon-isopropyl-lysine, 3-(4-tetrahydropyridyl)-glycine, 3-(4-tetrahydropyridyl)-alanine, N,N-gamma, gamma'-diethyl-homoarginine. Included also are compounds such as α-methyl-arginine, α-methyl-2,3-diaminopropionic acid, α-methyl-histidine, α-methyl-ornithine where the alkyl group occupies the pro-R position of the α-carbon. Also included are the amides formed from alkyl, aromatic, heteroaromatic (where the heteroaromatic group has one or more nitrogens, oxygens or sulfur atoms singly or in combination), carboxylic acids or any of the many well-known activated derivatives such as acid chlorides, active esters, active azolides and related derivatives, and lysine, ornithine, or 2,3-diaminopropionic acid; d) substitution of acidic amino acids, including aspartic acid, glutamic acid, homoglutamic acid, tyrosine, alkyl, aryl, arylalkyl, and heteroaryl sulfonamides of 2,4-diaminopriopionic acid, ornithine or lysine and tetrazole-substituted alkyl amino acids; e) substitution of side chain amide residues, including asparagine, glutamine, and alkyl or aromatic substituted derivatives of asparagine or glutamine; and f) substitution of hydroxyl-containing amino acids, including serine, threonine, homoserine, 2,3-diaminopropionic acid, and alkyl or aromatic substituted derivatives of serine or threonine.

The term "IL10 polypeptide" includes IL-10 polypeptides comprising one or more naturally occurring non-genetically encoded L-amino acids, synthetic L-amino acids, or D-enantiomers of an amino acid. For example, IL-10 can comprise only D-amino acids. For example, an IL-10 polypeptide can comprise one or more of the following residues: hydroxyproline, β-alanine, o-aminobenzoic acid, m-aminobenzoic acid, p-aminobenzoic acid, m-aminomethylbenzoic acid, 2,3-diaminopropionic acid, α-aminoisobutyric acid, N-methylglycine (sarcosine), ornithine, citrulline, t-butylalanine, t-butylglycine, N-methylisoleucine, phenylglycine, cyclohexylalanine, norleucine, naphthylalanine, pyridylalanine 3-benzothienyl alanine, 4-chlorophenylalanine, 2-fluorophenylalanine, 3-fluorophenylalanine, 4-fluorophenylalanine, penicillamine, 1,2,3,4-tetrahydroisoquinoline-3-carboxylic acid, β-2-thienylalanine, methionine sulfoxide, homoarginine, N-acetyl lysine, 2,4-diamino butyric acid, rho-aminophenylalanine, N-methylvaline, homocysteine, homoserine, ε-amino hexanoic acid, ω-aminohexanoic acid, ω-aminoheptanoic acid, ω-aminooctanoic acid, ω-aminodecanoic acid, ω-aminotetradecanoic acid, cyclohexylalanine, α,γ-diaminobutyric acid, α,β-diaminopropionic acid, δ-amino valeric acid, and 2,3-diaminobutyric acid.

The term "IL10 polypeptide" includes IL-10 polypeptides comprising one or more additional cysteine residues or cysteine analogs to facilitate linkage of the IL-10 polypeptide to another polypeptide via a disulfide linkage or to provide for cyclization of the IL-10 polypeptide. Methods of introducing a cysteine or cysteine analog are known in the art; see, e.g., U.S. Pat. No. 8,067,532.

The term "IL10 polypeptide" includes cyclized polypeptides. A cyclizing bond can be generated with any combination of amino acids (or with an amino acid and —$(CH_2)_n$—CO— or —$(CH2)_n$-$C_6H_4$—CO—) with functional groups which allow for the introduction of a bridge. Some examples are disulfides, disulfide mimetics such as the —$(CH2)_n$-carba bridge, thioacetal, thioether bridges (cystathionine or lanthionine) and bridges containing esters and ethers. In these examples, n can be any integer, but is frequently less than ten.

The term "IL10 polypeptide" includes additional modifications including, for example, an N-alkyl (or aryl) substitution (ψ[CONR]), or backbone crosslinking to construct lactams and other cyclic structures. Other derivatives include C-terminal hydroxymethyl derivatives, o-modified derivatives (e.g., C-terminal hydroxymethyl benzyl ether), N-terminally modified derivatives including substituted amides such as alkylamides and hydrazides.

The term "IL10 polypeptide" includes a retroinverso analog (see, e.g., Sela and Zisman (1997) FASEB J. 11:449). Retro-inverso peptide analogs are isomers of linear polypeptides in which the direction of the amino acid sequence is reversed (retro) and the chirality, D- or L-, of one or more amino acids therein is inverted (inverso), e.g., using D-amino acids rather than L-amino acids. [See, e.g., Jameson et al. (1994) Nature 368:744; and Brady et al. (1994) Nature 368:692].

The term "IL10 polypeptide" includes modifications to include a "Protein Transduction Domain" (PTD). The term "protein transcution domain" refers to a polypeptide, polynucleotide, carbohydrate, or organic or inorganic molecule that facilitates traversing a lipid bilayer, micelle, cell membrane, organelle membrane, or vesicle membrane. A PTD attached to another molecule facilitates the molecule traversing a membrane, for example going from extracellular space to intracellular space, or cytosol to within an organelle. In some embodiments, a PTD is covalently linked to the amino terminus of an IL-10 polypeptide, while in other embodiments, a PTD is covalently linked to the carboxyl terminus of an IL-10 polypeptide. Exemplary protein transduction domains include, but are not limited to, a minimal undecapeptide protein transduction domain (corresponding to residues 47-57 of HIV-1 TAT comprising YGRKKRRQRRR; SEQ ID NO:15); a polyarginine sequence comprising a number of arginine residues sufficient to direct entry into a cell (e.g., 3, 4, 5, 6, 7, 8, 9, 10, or 10-50 arginines); a VP22 domain (Zender et al. (2002) Cancer Gene Ther. 9(6):489-96); a *Drosophila* Antennapedia protein transduction domain (Noguchi et al. (2003) Diabetes 52(7):1732-1737); a truncated human calcitonin peptide (Trehin et al. (2004) Pharm. Research 21:1248-1256); polylysine (Wender et al. (2000) Proc. Natl. Acad. Sci. USA 97:13003-13008); RRQRRTSKLMKR (SEQ ID NO: 16); Transportan GWTLNSAGYLLGKINLKALAALAKKIL (SEQ ID NO: 17); KALAWEAKLAKALAKALAKHLAKALAKALKCEA (SEQ ID NO:18); and RQIKIWFQNRRMKWKK (SEQ ID NO:19). Exemplary PTDs include, but are not limited to, YGRKKRRQRRR (SEQ ID NO: 15), RKKRRQRRR (SEQ ID NO:20); an arginine homopolymer of from 3 arginine residues to 50 arginine residues; exemplary PTD domain amino acid sequences include, but are not limited to, any of the following:

```
                        (SEQ ID NO: 15)
YGRKKRRQRRR;

                        (SEQ ID NO: 21)
RKKRRQRR;

                        (SEQ ID NO: 22)
YARAAARQARA;

                        (SEQ ID NO: 23)
THRLPRRRRRR;
and

                        (SEQ ID NO: 24)
GGRRARRRRRR.
```

The carboxyl group $COR_3$ of the amino acid at the C-terminal end of an IL-10 polypeptide can be present in a free form (R3=OH) or in the form of a physiologically-tolerated alkaline or alkaline earth salt such as, e.g., a sodium, potassium or calcium salt. The carboxyl group can also be esterified with primary, secondary or tertiary alcohols such as, e.g., methanol, branched or unbranched C1-C6-alkyl alcohols, e.g., ethyl alcohol or tert-butanol. The carboxyl group can also be amidated with primary or secondary amines such as ammonia, branched or unbranched C1-C6-alkylamines or C1-C6 di-alkylamines, e.g., methylamine or dimethylamine.

The amino group of the amino acid NR1R2 at the N-terminus of an IL-10 polypeptide can be present in a free form (R1=H and R2=H) or in the form of a physiologically-tolerated salt such as, e.g., a chloride or acetate. The amino group can also be acetylated with acids such that R1=H and R2=acetyl, trifluoroacetyl, or adamantyl. The amino group can be present in a form protected by amino-protecting groups conventionally used in peptide chemistry, such as those provided above (e.g., Fmoc, Benzyloxy-carbonyl (Z), Boc, and Alloc). The amino group can be N-alkylated in which $R_1$ and/or $R_2$=$C_1$-$C_6$ alkyl or $C_2$-$C_8$ alkenyl or $C_7$-$C_9$ aralkyl. Alkyl residues can be straight-chained, branched or cyclic (e.g., ethyl, isopropyl and cyclohexyl, respectively).

The term "IL10 polypeptide" includes active fragments of IL-10 polypeptides. The term "active IL-10 polypeptide fragment" refers to IL-10 polypeptides that are fragments (e.g., subsequences) of naturally occurring IL-10 species containing contiguous amino acid residues derived from the naturally occurring IL-10 species are capable of dimerizing with another IL-10 polypeptide such dimer possessing IL-10 activity. The length of contiguous amino acid residues of a peptide or a polypeptide subsequence varies depending on the specific naturally-occurring amino acid sequence from which the subsequence is derived. In general, peptides and polypeptides can be from about 20 amino acids to about 40 amino acids, from about 40 amino acids to about 60 amino acids, from about 60 amino acids to about 80 amino acids, from about 80 amino acids to about 100 amino acids, from about 100 amino acids to about 120 amino acids, from about 120 amino acids to about 140 amino acids, from about 140 amino acids to about 150 amino acids, from about 150 amino acids to about 155 amino acids, from about 155 amino acids up to the full-length peptide or polypeptide.

Additionally, IL-10 polypeptides can have a defined sequence identity compared to a reference sequence over a defined length of contiguous amino acids (e.g., a "comparison window"). Methods of alignment of sequences for comparison are well-known in the art. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Madison, Wis.), or by manual alignment and visual inspection (see, e.g., Current Protocols in Molecular Biology (Ausubel et al., eds. 1995 supplement)). Software packages and databases for determining, e.g., antigenic fragments, leader sequences, protein folding, functional domains, glycosylation sites, and sequence alignments, are available (see, e.g., GCG Wisconsin Package (Accelrys, Inc., San Diego, CA); and DeCypher™ (TimeLogic Corp., Crystal Bay, NV).

As an example, a suitable IL-10 polypeptide can comprise an amino acid sequence having at least about 75%, at least about 80%, at least about 85%, at least about 90%, at least about 95%, at least about 98%, or at least about 99%, amino acid sequence identity to a contiguous stretch of from about 20 amino acids to about 40 amino acids, from about 40 amino acids to about 60 amino acids, from about 60 amino acids to about 80 amino acids, from about 80 amino acids to about 100 amino acids, from about 100 amino acids to about 120 amino acids, from about 120 amino acids to about 140 amino acids, from about 140 amino acids to about 150 amino acids, from about 150 amino acids to about 155 amino acids, from about 155 amino acids up to the full-length peptide or polypeptide.

As discussed further below, the IL-10 polypeptides can be isolated from a natural source (e.g., an environment other than its naturally-occurring environment) and can also be recombinantly made (e.g., in a genetically modified host cell such as bacteria, yeast, *Pichia*, insect cells, and the like), where the genetically modified host cell is modified with a nucleic acid comprising a nucleotide sequence encoding the polypeptide. The IL-10 polypeptides can also be synthetically produced (e.g., by cell-free chemical synthesis).

The present disclosure contemplates IL-10 agents comprised of IL-10 polypeptides obtained from a variety of mammalian and non-mammalian sources including orthologs, and modified forms thereof. In addition to the human polypeptides and the nucleic acid molecules which encode them, the present disclosure contemplates IL-10 polypeptides and corresponding nucleic acid molecules from other species including murine, rat (accession NP_036986.2; GI 148747382); cow (accession NP_776513.1; GI 41386772); sheep (accession NP_001009327.1; GI 57164347); dog (accession ABY86619.1; GI 166244598); and rabbit (accession AAC23839.1; GI 3242896).

Examples of IL-10 agents derived from non-mammalian sources include viral IL-10 derived from the family herpesviridae subfamily betaherpesvirinae, genus cytomegalovirus including human cytomegalovirus, Genbank Accession Nos. AAR31656 and ACR49217), green monkey cytomegalovirus, (Genbank Accession No AEV80459), rhesus cytomegalovirus, (Genbank Accession No. AAF59907), baboon cytomegalovirus, (Genbank Accession No. AAF63436), owl monkey cytomegalovirus, (Genbank Accession No. AEV80800), and squirrel monkey cytomegalovirus, (Genbank Accession No. AEV80955; family Gammaherpesvirinae genus lymphocryptovirus Epstein-Barr virus, (Genbank Accession No. CAD53385), bonobo herpesvirus, (Genbank Accession No. XP_003804206.1), Rhesus lymphocryptovirus, (Genbank Accession No. AAK95412), baboon lymphocryptovirus, (Genbank Accession No. AAF23949); genus macavirus including ovine herpesvirus 2 (Genbank Accession No. AAX58040); genus percavirus including equid herpesvirus 2 (Genbank Accession No. AAC13857); family alloherpesviridea genus cyprinivirus including cyprinid herpesvirus 3 (Genbank Accession No. ABG429610), anguillid herpesvirus 1 (Genbank Accession No. AFK25321); family poxviridae, subfamily chodopoxvirinae genus parapoxvirus including orf virus (Genbank Accession No. AAR98352), bovine papular stomatitis virus (Genbank Accession No AAR98483), pseudocowpox virus (Genbank Accession No. ADC53770); genus capripoxvirus including lumpy skin disease virus (Genbank Accession No AAK84966), sheeppox virus (Genbank Accession No. NP_659579), goatpox virus (Genbank Accession No. YP_00129319 and avipoxvirus including canarypox virus (Genbank Accession No NP_955041).

The term "IL-10 activity" is refers to IL-10 agents typically exert their effects by binding to the IL-10 receptor. The IL-10 receptor, a type II cytokine receptor, consists of alpha and beta subunits, which are also referred to as R1 and R2, respectively. Receptor activation requires binding to both alpha and beta. One IL-10 monomer of the dimeric IL-10 binds to alpha and the other IL-10 monomer of the IL-10 binds to beta. IL-10 activity may be assessed by assays well known in the art. For example, the IL-10 activity of an IL-10 agent may be determined in using the TNF-α inhibition assay, MC9 proliferation assay, CD8 T-cell IFNγ Secretion Assay or in tumor models and tumor analysis as provided below. However, it is understood by the skilled artisan that the following assays are representative, and not exclusionary of, assays to determine IL-10 activity. The skilled artisan will understand that any art recognized assay or methodology to measure IL-10 activity may be used alone or in combination to evaluate the activity of the IL-10 agents described herein.

The IL-10 activity of an IL-10 agent may be assessed in substantial accordance with the following TNFα inhibition assay. Briefly, PMA-stimulation of U937 cells (lymphoblast human cell line from lung available from Sigma-Aldrich (#85011440); St. Louis, MO) causes the cells to secrete TNFα, and subsequent treatment of these TNFα-secreting cells with a test agent having IL-10 activity will result in a decrease in TNFα secretion in a dose-dependent manner. An exemplary TNFα inhibition assay can be performed using the following protocol. After culturing U937 cells in RMPI containing 10% FBS/FCS and antibiotics, plate 1×105, 90% viable U937 cells in 96-well flat bottom plates (any plasma-treated tissue culture plates (e.g., Nunc; Thermo Scientific, USA) can be used) in triplicate per condition. Plate cells to provide for the following conditions (all in at least triplicate; for 'media alone' the number of wells is doubled because one-half will be used for viability after incubation with 10 nM PMA): 5 ng/ml LPS alone; 5 ng/mL LPS+0.1 ng/mL rhIL-10; 5 ng/mL LPS+1 ng/mL rhIL-10; 5 ng/mL LPS+10 ng/mL rhIL-10; 5 ng/mL LPS+100 ng/mL rhIL-10; 5 ng/mL LPS+1000 ng/mL rhIL-10; 5 ng/mL LPS+0.1 ng/mL PEG-rhIL-10; 5 ng/mL LPS+1 ng/mL PEG-rhIL-10; 5 ng/mL LPS+10 ng/mL PEG-rhIL-10; 5 ng/mL LPS+100 ng/mL PEG-rhIL-10; and 5 ng/mL LPS+1000 ng/mL PEG-rhIL-10. Expose each well to 10 nM PMA in 200 μL for 24 hours, culturing at 37° C. in 5% $CO_2$ incubator, after which time ~90% of cells should be adherent. The three extra wells are re-suspended, and the cells are counted to assess viability (>90% should be viable). Wash gently but thoroughly 3× with fresh, non-PMA-containing media, ensuring that cells are still in the wells. Add 100 μL per well of media containing the appropriate concentrations (2× as the volume will be diluted by 100%) of the IL-10 agent, incubate at 37° C. in a 5% $CO_2$ incubator for 30 minutes. Add 100 μL per well of 10 ng/mL stock LPS to achieve a final concentration of 5 ng/mL LPS in each well, and incubate at 37° C. in a 5% $CO_2$ incubator for 18-24 hours. Remove supernatant and perform TNFα ELISA according to the manufacturer's instructions. Run each conditioned supernatant in duplicate in ELISA.

The IL-10 activity of an IL-10 agent may be assessed in substantial accordance with the following MC/9 cell proliferation assay. Briefly, the administration of compounds having IL-10 activity to MC/9 cells causes increased cell proliferation in a dose-dependent manner. MC/9 is a murine cell line with characteristics of mast cells available from Cell Signaling Technology; Danvers, MA. Thompson-Snipes, L. et al. ((1991) J. Exp. Med. 173:507-10) describe a standard assay protocol in which MC/9 cells are supplemented with IL3+IL10 and IL3+IL4+IL10. Those of ordinary skill in the art will be able to modify the standard assay protocol described in Thompson-Snipes, L. et al, such that cells are only supplemented with IL-10.

The IL-10 activity of an IL-10 agent may be assessed in substantial accordance with the following CD8 T-cell IFNγ Secretion Assay. Briefly, activated primary human CD8 T-cells secrete IFNγ when treated with compounds having IL-10 activity and then with an anti-CD3 antibody. The following protocol provides an exemplary CD8 T-cell IFNγ secretion assay. Human primary peripheral blood mononuclear cells (PBMCs) can be isolated according to any standard protocol (see, e.g., Fuss et al. (2009) Current Protocols in Immunology, Unit 7.1, John Wiley, Inc., NY). 2.5 mL of PBMCs (at a cell density of 10 million cells/mL) can be cultured per well with complete RPMI, containing RPMI (Life Technologies; Carlsbad, CA), 10 mM HEPES (Life Technologies; Carlsbad, CA), 10% Fetal Calf Serum (Hyclone Thermo Fisher Scientific; Waltham, MA) and Penicillin/Streptomycin cocktail (Life Technologies; Carlsbad, CA), in any standard tissue culture treated 6-well plate (BD; Franklin Lakes, NJ). The IL-10 agent is then added to the wells at a final concentration of 100 ng/mL; a final concentration of 10 μg/mL of antibodies blocking the function of inhibitory/checkpoint receptors can also be added in combination with the IL-10 agent. Cells can be incubated in a humidified 37° C. incubator with 5% $CO_2$ for 6-7 days. After incubation, CD8 T-cells are isolated using Miltenyi Biotec's MACS cell separation technology in substantial accordance with the manufacturer's instructions (Miltenyi Biotec; Auburn, CA). The isolated CD8 T-cells can then be cultured with complete RPMI containing 1 μg/mL anti-CD3 antibody (Affymetrix eBioscience; San Diego, CA) in any standard tissue culture plate for 4 hours. After the 4 hour incubation, the media is collected and assayed for IFNγ using a commercial ELISA kit (e.g. Affymetrix eBioscience; San Diego, CA) in substantial accordance with the manufacturer's instructions.

Tumor models can be used to evaluate the activity of an IL-10 agent on various tumors. The tumor models and tumor analyses described hereafter are representative of those that can be utilized. Syngeneic mouse tumor cells are injected subcutaneously or intradermally at $10^4$, $10^5$ or $10^6$ cells per tumor inoculation. Ep2 mammary carcinoma, CT26 colon carcinoma, PDV6 squamous carcinoma of the skin and 4T1 breast carcinoma models can be used (see, e.g., Langowski et al. (2006) Nature 442:461-465). Immunocompetent Balb/C or B-cell deficient Balb/C mice can be used. IL-10 agents based on murine IL-10 species may be administered to immunocompetent mice, IL-10 agents based on human IL-10 or other non-murine species treatment is typically provided in the B-cell deficient mice. Tumor growth is typically monitored twice weekly using electronic calipers. Tumor volume can be calculated using the formula ($\text{width}^2 \times \text{length}/2$) where length is the longer dimension. Tumors are allowed to reach a size of 90-250 $mm^3$ before administration of the IL-10 test agent. The IL-10 agent or buffer control is administered at a site distant from the tumor implantation. Tumor growth following administration of the IL-10 test agent is typically monitored twice weekly using electronic calipers as above and the effects on tumor volume in response to the administration of the IL-10 test agent evalated over time. Tumor tissues and lymphatic organs are harvested at various endpoints to measure mRNA expression for a number of inflammatory markers and to perform immunohistochemistry for several inflammatory cell markers. The tissues are snap-frozen in liquid nitrogen and stored at −80° C.

In one embodiment, the IL-10 polypeptide is a human IL-10 polypeptide. As used herein, the term "human IL-10" or "hIL10" refers to an IL10 agent comprised of two human iIL-10 polypeptides. In one embodiment, a human IL-10 polypeptide is a 160 amino acid polypeptide having the amino acid sequence (amino- to carboxy-terminus):

```
                                        (SEQ ID NO 25)
SPGQGTQSEN SCTHFPGNLP NMLRDLRDAF SRVKTFFQMK

DQLDNLLLKE SLLEDFKGYL GCQALSEMIQ FYLEEVMPQA

ENQDPDIKAH VNSLGENLKT LRLRLRRCHR FLPCENKSKA

VEQVKNAFNK LQEKGIYKAM SEFDIFINYI EAYMTMKIRN
```

In one embodiment, a human IL-10 polypeptide is a 161 amino acid polypeptide having the amino acid sequence (amino- to carboxy-terminus):

```
                                        (SEQ ID NO 26)
MSPGQGTQSE NSCTHFPGNL PNMLRDLRDA FSRVKTFFQM

KDQLDNLLLK ESLLEDFKGY LGCQALSEMI QFYLEEVMPQ

AENQDPDIKA HVNSLGENLK TLRLRLRRCH RFLPCENKSK

AVEQVKNAFN KLQEKGIYKA MSEFDIFINY IEAYMTMKIR N
```

In one embodiment, a human IL-10 polypeptide is a 161 amino acid polypeptide having the amino acid sequence (amino- to carboxy-terminus):

```
                                        (SEQ ID NO 27)
N-formyl-MSPGQGTQSE NSCTHFPGNL PNMLRDLRDA

FSRVKTFFQM KDQLDNLLLK ESLLEDFKGY LGCQALSEMI

QFYLEEVMPQ AENQDPDIKA HVNSLGENLK TLRLRLRRCH

RFLPCENKSK AVEQVKNAFN KLQEKGIYKA MSEFDIFINY

IEAYMTMKIR N
```

It should be noted that any reference to "human" in connection with the polypeptides and nucleic acid molecules of the present disclosure is not meant to be limiting with respect to the manner in which the polypeptide or nucleic acid is obtained or the source, but rather is only with reference to the sequence as it can correspond to a sequence of a naturally occurring human polypeptide or nucleic acid molecule.

IL-10 polypeptides can be isolated from a natural source (e.g., an environment other than its naturally-occurring environment) and can also be recombinantly made (e.g., in a genetically modified host cell such as bacteria, yeast, *Pichia*, insect cells, and the like), where the genetically modified host cell is modified with a nucleic acid comprising a nucleotide sequence encoding the polypeptide. The IL-10 polypeptides can also be synthetically produced (e.g., by cell-free chemical synthesis).

Where a IL-10 polypeptide is chemically synthesized, the synthesis can proceed via liquid-phase or solid-phase. Solid-phase peptide synthesis (SPPS) allows the incorporation of unnatural amino acids and/or peptide/protein backbone modification. Various forms of SPPS, such as 9-fluorenylmethoxycarbonyl (Fmoc) and t-butyloxycarbonyl (Boc), are available for synthesizing polypeptides of the present disclosure. Details of the chemical syntheses are known in the art (e.g., Ganesan A. (2006) Mini Rev. Med. Chem. 6:3-10; and Camarero J. A. et al., (2005) Protein Pept Lett. 12:723-8).

Solid phase peptide synthesis can be performed as described hereafter. The alpha functions (Na) and any reactive side chains are protected with acid-labile or base-labile groups. The protective groups are stable under the conditions for linking amide bonds but can readily be cleaved without impairing the peptide chain that has formed. Suitable protective groups for the α-amino function include, but are not limited to, the following: Boc, benzyloxycarbonyl (Z), O-chlorbenzyloxycarbonyl, bi-phenylisopropyloxycarbonyl, tert-amyloxycarbonyl (Amoc), α,α-dimethyl-3,5-dimethoxy-benzyloxycarbonyl, o-nitrosulfenyl, 2-cyano-t-butoxy-carbonyl, Fmoc, 1-(4,4-dimethyl-2,6-dioxocylohex-1-ylidene)ethyl (Dde) and the like.

Suitable side chain protective groups include, but are not limited to: acetyl, allyl (All), allyloxycarbonyl (Alloc), benzyl (Bzl), benzyloxycarbonyl (Z), t-butyloxycarbonyl (Boc), benzyloxymethyl (Bom), o-bromobenzyloxycarbonyl, t-butyl (tBu), t-butyldimethylsilyl, 2-chlorobenzyl, 2-chlorobenzyloxycarbonyl, 2,6-dichlorobenzyl, cyclohexyl, cyclopentyl, 1-(4,4-dimethyl-2,6-dioxocyclohex-1-ylidene)ethyl (Dde), isopropyl, 4-methoxy-2,3-6-trimethylbenzylsulfonyl (Mtr), 2,3,5,7,8-pentamethylchroman-6-sulfonyl (Pmc), pivalyl, tetrahydropyran-2-yl, tosyl (Tos), 2,4,6-trimethoxybenzyl, trimethylsilyl and trityl (Trt).

In the solid phase synthesis, the C-terminal amino acid is coupled to a suitable support material. Suitable support materials are those which are inert towards the reagents and reaction conditions for the step-wise condensation and cleavage reactions of the synthesis process and which do not dissolve in the reaction media being used. Examples of commercially-available support materials include styrene/divinylbenzene copolymers which have been modified with reactive groups and/or polyethylene glycol; chloromethylated styrene/divinylbenzene copolymers; hydroxymethylated or aminomethylated styrene/divinylbenzene copolymers; and the like. When preparation of the peptidic acid is desired, polystyrene (1%)-divinylbenzene or TentaGel® derivatized with 4-benzyloxybenzyl-alcohol (Wang-anchor) or 2-chlorotrityl chloride can be used. In the case of the peptide amide, polystyrene (1%) divinylbenzene or TentaGel® derivatized with 5-(4'-aminomethyl)-3',5'-dimethoxyphenoxy)valeric acid (PAL-anchor) or p-(2,4-dimethoxyphenyl-amino methyl)-phenoxy group (Rink amide anchor) can be used.

The linkage to the polymeric support can be achieved by reacting the C-terminal Fmoc-protected amino acid with the support material by the addition of an activation reagent in ethanol, acetonitrile, N,N-dimethylformamide (DMF), dichloromethane, tetrahydrofuran, N-methylpyrrolidone or similar solvents at room temperature or elevated temperatures (e.g., between 40° C. and 60° C.) and with reaction times of, e.g., 2 to 72 hours.

The coupling of the Nα-protected amino acid (e.g., the Fmoc amino acid) to the PAL, Wang or Rink anchor can, for example, be carried out with the aid of coupling reagents such as N,N'-dicyclohexylcarbodiimide (DCC), N,N'-diisopropylcarbodiimide (DIC) or other carbodiimides, 2-(1H-benzotriazol-1-yl)-1,1,3,3-tetramethyluronium tetrafluoroborate (TBTU) or other uronium salts, O-acyl-ureas, benzotriazol-1-yl-tris-pyrrolidino-phosphonium hexafluorophosphate (PyBOP) or other phosphonium salts, N-hydroxysuccinimides, other N-hydroxyimides or oximes in the presence or absence of 1-hydroxybenzotriazole or 1-hydroxy-7-azabenzotriazole, e.g., with the aid of TBTU with addition of HOBt, with or without the addition of a base such as, for example, diisopropylethylamine (DIEA), triethylamine or N-methylmorpholine, e.g., diisopropylethylamine with reaction times of 2 to 72 hours (e.g., 3 hours in a 1.5 to 3-fold excess of the amino acid and the coupling reagents, for example, in a 2-fold excess and at temperatures between about 10° C. and 50° C., for example, 25° C. in a solvent such as dimethylformamide, N-methylpyrrolidone or dichloromethane, e.g., dimethylformamide).

Instead of the coupling reagents, it is also possible to use the active esters (e.g., pentafluorophenyl, p-nitrophenyl or the like), the symmetric anhydride of the Na-Fmoc-amino acid, its acid chloride or acid fluoride, under the conditions described above.

The Nα-protected amino acid (e.g., the Fmoc amino acid) can be coupled to the 2-chlorotrityl resin in dichloromethane with the addition of DIEA and having reaction times of 10 to 120 minutes, e.g., 20 minutes, but is not limited to the use of this solvent and this base.

The successive coupling of the protected amino acids can be carried out according to conventional methods in peptide synthesis, typically in an automated peptide synthesizer. After cleavage of the Na-Fmoc protective group of the coupled amino acid on the solid phase by treatment with, e.g., piperidine (10% to 50%) in dimethylformamide for 5 to 20 minutes, e.g., 2×2 minutes with 50% piperidine in DMF and 1×15 minutes with 20% piperidine in DMF, the next protected amino acid in a 3 to 10-fold excess, e.g., in a 10-fold excess, is coupled to the previous amino acid in an inert, non-aqueous, polar solvent such as dichloromethane, DMF or mixtures of the two and at temperatures between about 10° C. and 50° C., e.g., at 25° C. The previously mentioned reagents for coupling the first Na-Fmoc amino acid to the PAL, Wang or Rink anchor are suitable as coupling reagents. Active esters of the protected amino acid, or chlorides or fluorides or symmetric anhydrides thereof can also be used as an alternative.

At the end of the solid phase synthesis, the peptide is cleaved from the support material while simultaneously cleaving the side chain protecting groups. Cleavage can be carried out with trifluoroacetic acid or other strongly acidic media with addition of 5%-20% V/V of scavengers such as dimethylsulfide, ethylmethylsulfide, thioanisole, thiocresol, m-cresol, anisole ethanedithiol, phenol or water, e.g., 15% v/v dimethylsulfide/ethanedithiol/m-cresol 1:1:1, within 0.5 to 3 hours, e.g., 2 hours. Peptides with fully protected side chains are obtained by cleaving the 2-chlorotrityl anchor with glacial acetic acid/trifluoroethanol/dichloromethane 2:2:6. The protected peptide can be purified by chromatography on silica gel. If the peptide is linked to the solid phase via the Wang anchor and if it is intended to obtain a peptide with a C-terminal alkylamidation, the cleavage can be carried out by aminolysis with an alkylamine or fluoroalkylamine. The aminolysis is carried out at temperatures between about −10° C. and 50° C. (e.g., about 25° C.), and reaction times between about 12 and 24 hours (e.g., about 18 hours). In addition, the peptide can be cleaved from the support by re-esterification, e.g., with methanol.

The acidic solution that is obtained can be admixed with a 3 to 20-fold amount of cold ether or n-hexane, e.g., a 10-fold excess of diethyl ether, in order to precipitate the peptide and hence to separate the scavengers and cleaved protective groups that remain in the ether. A further purification can be carried out by re-precipitating the peptide several times from glacial acetic acid. The precipitate that is obtained can be taken up in water or tert-butanol or mixtures of the two solvents, e.g., a 1:1 mixture of tert-butanol/water, and freeze-dried.

The peptide obtained can be purified by various chromatographic methods, including ion exchange over a weakly basic resin in the acetate form; hydrophobic adsorption chromatography on non-derivatized polystyrene/divinylbenzene copolymers (e.g., Amberlite® XAD); adsorption chromatography on silica gel; ion exchange chromatography, e.g., on carboxymethyl cellulose; distribution chromatography, e.g., on Sephadex® G-25; countercurrent distribution chromatography; or high pressure liquid chromatography (HPLC) e.g., reversed-phase HPLC on octyl or octadecylsilylsilica (ODS) phases.

Methods describing the preparation of human and mouse IL-10 can be found in, for example, U.S. Pat. No. 5,231,012, which teaches methods for the production of proteins having IL-10 activity, including recombinant and other synthetic techniques. IL-10 can be of viral origin, and the cloning and expression of a viral IL-10 from Epstein Barr virus (BCRF1 protein) is disclosed in Moore et al., (1990) Science 248: 1230. IL-10 can be obtained in a number of ways using standard techniques known in the art, such as those described herein. Recombinant human IL-10 is also commercially available, e.g., from PeproTech, Inc., Rocky Hill, N.J.

Nucleic acid molecules encoding the IL-10 agents are contemplated by the present disclosure, including their naturally-occurring and non-naturally occurring isoforms, allelic variants and splice variants. The present disclosure also encompasses nucleic acid sequences that vary in one or more bases from a naturally-occurring DNA sequence but still translate into an amino acid sequence that corresponds to an IL-10 polypeptide due to degeneracy of the genetic code.

Where a polypeptide is produced using recombinant techniques, the polypeptide can be produced as an intracellular protein or as a secreted protein, using any suitable construct and any suitable host cell, which can be a prokaryotic or eukaryotic cell, such as a bacterial (e.g., *E. coli*) or a yeast host cell, respectively. Other examples of eukaryotic cells that can be used as host cells include insect cells, mammalian cells, and/or plant cells. Where mammalian host cells are used, they can include human cells (e.g., HeLa, 293, H9 and Jurkat cells); mouse cells (e.g., NIH3T3, L cells, and C127 cells); primate cells (e.g., Cos 1, Cos 7 and CV1); and hamster cells (e.g., Chinese hamster ovary (CHO) cells).

A variety of host-vector systems suitable for the expression of a polypeptide can be employed according to standard procedures known in the art. See, e.g., Sambrook et al., 1989 Current Protocols in Molecular Biology Cold Spring Harbor Press, New York; and Ausubel et al. 1995 Current Protocols in Molecular Biology, Eds. Wiley and Sons. Methods for introduction of genetic material into host cells include, for example, transformation, electroporation, conjugation, calcium phosphate methods and the like. The method for transfer can be selected so as to provide for stable expression of the introduced polypeptide-encoding nucleic acid. The polypeptide-encoding nucleic acid can be provided as an inheritable episomal element (e.g., a plasmid) or can be genomically integrated. A variety of appropriate vectors for use in production of a polypeptide of interest are commercially available.

Vectors can provide for extrachromosomal maintenance in a host cell or can provide for integration into the host cell genome. The expression vector provides transcriptional and translational regulatory sequences, and can provide for inducible or constitutive expression where the coding region is operably-linked under the transcriptional control of the transcriptional initiation region, and a transcriptional and translational termination region. In general, the transcriptional and translational regulatory sequences can include, but are not limited to, promoter sequences, ribosomal binding sites, transcriptional start and stop sequences, translational start and stop sequences, and enhancer or activator sequences. Promoters can be either constitutive or inducible, and can be a strong constitutive promoter (e.g., T7).

Expression constructs generally have convenient restriction sites located near the promoter sequence to provide for the insertion of nucleic acid sequences encoding proteins of interest. A selectable marker operative in the expression host can be present to facilitate selection of cells containing the vector. Moreover, the expression construct can include additional elements. For example, the expression vector can have one or two replication systems, thus allowing it to be maintained in organisms, for example, in mammalian or insect cells for expression and in a prokaryotic host for cloning and amplification. In addition, the expression construct can contain a selectable marker gene to allow the selection of transformed host cells. Selectable genes are well known in the art and will vary with the host cell used.

Isolation and purification of a protein can be accomplished according to methods known in the art. For example, a protein can be isolated from a lysate of cells genetically modified to express the protein constitutively and/or upon induction, or from a synthetic reaction mixture by immunoaffinity purification, which generally involves contacting the sample with an anti-protein antibody, washing to remove non-specifically bound material, and eluting the specifically bound protein. The isolated protein can be further purified by dialysis and other methods normally employed in protein purification. In one embodiment, the protein can be isolated using metal chelate chromatography methods. Proteins can contain modifications to facilitate isolation.

The polypeptides can be prepared in substantially pure or isolated form (e.g., free from other polypeptides). The polypeptides can be present in a composition that is enriched for the polypeptide relative to other components that can be present (e.g., other polypeptides or other host cell components). For example, purified polypeptide can be provided such that the polypeptide is present in a composition that is substantially free of other expressed proteins, e.g., less than about 90%, less than about 60%, less than about 50%, less than about 40%, less than about 30%, less than about 20%, less than about 10%, less than about 5%, or less than about 1%.

An IL-10 polypeptide can be generated using recombinant techniques to manipulate different IL-10-related nucleic acids known in the art to provide constructs capable of encoding the IL-10 polypeptide. It will be appreciated that, when provided a particular amino acid sequence, the ordinary skilled artisan will recognize a variety of different nucleic acid molecules encoding such amino acid sequence in view of her background and experience in, for example, molecular biology.

The term "modified IL-10 agents" are IL-10 agents that have been modified by one or more modifications such as pegylation glycosylation (N- and O-linked); polysialylation; albumin fusion molecules comprising serum albumin (e.g., human serum albumin (HSA), cyno serum albumin, or bovine serum albumin (BSA)); albumin binding through, for example a conjugated fatty acid chain (acylation); and Fc-fusion proteins. Modified IL-10 agents may be prepared to order to enhance one or more properties for example, modulating immunogenicity; methods of increasing water solubility, bioavailability, serum half-life, and/or therapeutic half-life; and/or modulating biological activity. Certain modifications can also be useful to, for example, raise of antibodies for use in detection assays (e.g., epitope tags) and to provide for ease of protein purification.

In one embodiment, the modified IL-10 agent is a PEG-IL10 agent. The term "PEG-IL-10 agent" refers to a modified IL-10 agent comprising at least one polyethylene glycol (PEG) molecule covalently attached (conjugated) to at least one amino acid residue of an IL-10 polypeptide. The terms "monopegylated IL-10 agent" and "mono-PEG-IL-10 agent" refer to an IL-10 agent with a polyethylene glycol molecule covalently attached to a single amino acid residue on one IL-10 polypeptide of the IL-10 dimer, generally via a linker. As used herein, the terms "dipegylated IL-10" and "di-PEG-IL-10" indicate that at least one polyethylene glycol molecule is attached to a single residue on IL-10 polypeptide of the IL-10 dimer, generally via a linker.

Pegylation of IL-10 agents results in improvement of certain properties including pharmacokinetic parameters (e.g., serum half-life), enhancement of activity, improved physical and thermal stability, protection against susceptibility to enzymatic degradation, increased solubility, longer in vivo circulating half-life and decreased clearance, reduced immunogenicity and antigenicity, and reduced toxicity. In addition to the beneficial effects of pegylation on pharmacokinetic parameters, pegylation itself can enhance activity. For example, PEG-IL-10 has been shown to be more efficacious against certain cancers than unpegylated IL-10 (see, e.g., EP 206636A2).

In certain embodiments, the PEG-IL-10 agent used in the present disclosure is a mono-PEG-IL-10 agent in which one to nine PEG molecules are covalently attached via a linker to the α-amino group of the amino acid residue at the N-terminus of one IL-10 polypeptide of the IL-10 dimer. Monopegylation of one IL-10 polypeptide generally results in a non-homogeneous mixture of non-pegylated, monopegylated and dipegylated IL-10 polypeptides due to subunit shuffling. Particular embodiments of the present disclosure comprise the administration of a mixture of mono- and di-pegylated IL-10 agents produced by the methods described herein. In certain embodiments, the IL-10 agent is provided as a mixture of mono- and di-pegylated IL-10 species, the mixture having about 50% of a mono-PEG-IL-10 and about 50% of a di-PEG-IL-10 alternatively having about 40% of a mono-PEG-IL-10 and about 60% of a di-PEG-IL-10, alternatively having about 60% of a mono-PEG-IL-10 and about 40% of a di-PEG-IL-10, alternatively having about 55% of a mono-PEG-IL-10 and about 45% of a di-PEG-IL-10, or alternatively having about 45% of a mono-PEG-IL10 and about 55% of a di-PEG-IL-10.

The biological activity PEG-IL-10 agents may by assessing the levels of inflammatory cytokines (e.g., TNF-α or IFN-γ) in the serum of subjects challenged with a bacterial antigen (lipopolysaccharide (LPS)) and treated with PEG-IL-10, as described in U.S. Pat. No. 7,052,686.

Although the method or site of PEG attachment to IL-10 is not critical, in certain embodiments the pegylation does not alter, or only minimally alters, the activity of the IL-10 agent. In certain embodiments, the increase in half-life is greater than any decrease in biological activity.

PEGs suitable for conjugation to a IL-10 polypeptide sequence are generally soluble in water at room temperature, and have the general formula $R(O—CH_2—CH_2)_nO—R$, where R is hydrogen or a protective group such as an alkyl or an alkanol group, and where n is an integer from 1 to 1000. When R is a protective group, it generally has from 1 to 8 carbons. The PEG conjugated to the polypeptide sequence can be linear or branched.

Branched PEG derivatives, "star-PEGs" and multi-armed PEGs are contemplated by the present disclosure.

A molecular weight of the PEG used in the present disclosure is not restricted to any particular range. The PEG component of the PEG-IL-10 agent can have a molecular mass greater than about 5 kDa, greater than about 10 kDa, greater than about 15 kDa, greater than about 20 kDa, greater than about 30 kDa, greater than about 40 kDa, or greater than about 50 kDa. In some embodiments, the molecular mass is from about 5 kDa to about 10 kDa, from about 5 kDa to about 15 kDa, from about 5 kDa to about 20 kDa, from about 10 kDa to about 15 kDa, from about 10 kDa to about 20 kDa, from about 10 kDa to about 25 kDa or from about 10 kDa to about 30 kDa.

The present disclosure also contemplates compositions of conjugates wherein the PEGs have different n values, and thus the various different PEGs are present in specific ratios. For example, some compositions comprise a mixture of conjugates where n=1, 2, 3 and 4. In some compositions, the percentage of conjugates where n=1 is 18-25%, the percentage of conjugates where n=2 is 50-66%, the percentage of conjugates where n=3 is 12-16%, and the percentage of conjugates where n=4 is up to 5%. Such compositions can be produced by reaction conditions and purification methods known in the art. Chromatography may be used to resolve conjugate fractions, and a fraction is then identified which contains the conjugate having, for example, the desired number of PEGs attached, purified free from unmodified protein sequences and from conjugates having other numbers of PEGs attached.

PEGs suitable for conjugation to a polypeptide sequence are generally soluble in water at room temperature, and have the general formula $R(O—CH_2—CH_2)_nO—R$, where R is hydrogen or a protective group such as an alkyl or an alkanol group, and where n is an integer from 1 to 1000. When R is a protective group, it generally has from 1 to 8 carbons.

Two widely used first generation activated monomethoxy PEGs (mPEGs) are succinimdyl carbonate PEG (SC-PEG; see, e.g., Zalipsky, et al. (1992) Biotehnol. Appl. Biochem 15:100-114; and Miron and Wilcheck (1993) Bio-conjug. Chem. 4:568-569) and benzotriazole carbonate PEG (BTC-PEG; see, e.g., Dolence, et al. U.S. Pat. No. 5,650,234), which react preferentially with lysine residues to form a carbamate linkage, but are also known to react with histidine and tyrosine residues. The linkage to histidine residues on certain molecules (e.g., IFNα) has been shown to be a hydrolytically unstable imidazolecarbamate linkage (see, e.g., Lee and McNemar, U.S. Pat. No. 5,985,263). Second generation pegylation technology has been designed to avoid these unstable linkages as well as the lack of selectivity in residue reactivity. Use of a PEG-aldehyde linker targets a single site on the N-terminus of a polypeptide through reductive amination.

The PEG conjugated to the polypeptide sequence can be linear or branched. Branched PEG derivatives, "star-PEGs" and multi-armed PEGs are contemplated by the present disclosure. Specific embodiments PEGs useful in the practice of the present invention include a 10 kDa linear PEG-aldehyde (e.g., Sunbright® ME-100AL, NOF America Corporation, One North Broadway, White Plains, NY 10601 USA), 10 kDa linear PEG-NHS ester (e.g., Sunbright® ME-100CS, Sunbright® ME-100AS, Sunbright® ME-100GS, Sunbright® ME-100HS, NOF), a 20 kDa linear PEG-aldehyde (e.g. Sunbright® ME-200AL, NOF, a 20 kDa linear PEG-NHS ester (e.g., Sunbright® ME-200CS, Sunbright® ME-200AS, Sunbright® ME-200GS, Sunbright® ME-200HS, NOF), a 20 kDa 2-arm branched PEG-aldehyde the 20 kDA PEG-aldehyde comprising two 10 kDA linear PEG molecules (e.g., Sunbright® GL2-200AL3, NOF), a 20 kDa 2-arm branched PEG-NHS ester the 20 kDA PEG-NHS ester comprising two 10 kDA linear PEG molecules (e.g., Sunbright® GL2-200TS, Sunbright® GL200GS2, NOF), a 40 kDa 2-arm branched PEG-aldehyde the 40 kDA PEG-aldehyde comprising two 20 kDA linear PEG molecules (e.g., Sunbright® GL2-400AL3), a 40 kDa 2-arm branched PEG-NHS ester the 40 kDA PEG-NHS ester comprising two 20 kDA linear PEG molecules (e.g., Sunbright® GL2-400AL3, Sunbright® GL2-400GS2, NOF), a linear 30 kDa PEG-aldehyde (e.g., Sunbright® ME-300AL) and a linear 30 kDa PEG-NHS ester.

Pegylation most frequently occurs at the α-amino group at the N-terminus of the polypeptide, the epsilon amino group on the side chain of lysine residues, and the imidazole group on the side chain of histidine residues. Since most recombinant polypeptides possess a single alpha and a number of epsilon amino and imidazole groups, numerous positional isomers can be generated depending on the linker chemistry. General pegylation strategies known in the art can be applied herein.

The PEG can be bound to an IL-10 polypeptide of the present disclosure via a terminal reactive group (a "spacer") which mediates a bond between the free amino or carboxyl groups of one or more of the polypeptide sequences and polyethylene glycol. The PEG having the spacer which can be bound to the free amino group includes N-hydroxysuccinylimide polyethylene glycol, which can be prepared by activating succinic acid ester of polyethylene glycol with N-hydroxysuccinylimide. Another activated polyethylene glycol which can be bound to a free amino group is 2,4-bis(O-methoxypolyethyleneglycol)-6-chloro-s-triazine, which can be prepared by reacting polyethylene glycol monomethyl ether with cyanuric chloride. The activated polyethylene glycol which is bound to the free carboxyl group includes polyoxyethylenediamine.

Conjugation of one or more of the IL-10 polypeptide sequences of the present disclosure to PEG having a spacer can be carried out by various conventional methods. For example, the conjugation reaction can be carried out in solution at a pH of from 5 to 10, at temperature from 4° C. to room temperature, for 30 minutes to 20 hours, utilizing a molar ratio of reagent to protein of from 4:1 to 30:1. Reaction conditions can be selected to direct the reaction towards producing predominantly a desired degree of substitution. In general, low temperature, low pH (e.g., pH=5), and short reaction time tend to decrease the number of PEGs attached, whereas high temperature, neutral to high pH (e.g., pH≥7), and longer reaction time tend to increase the number of PEGs attached. Various means known in the art can be used to terminate the reaction. In some embodiments, the reaction is terminated by acidifying the reaction mixture and freezing at, e.g., −20° C. Pegylation of various molecules is discussed in, for example, U.S. Pat. Nos. 5,252,714; 5,643,575; 5,919,455; 5,932,462; and 5,985,263. PEG-IL-10 is described in, e.g., U.S. Pat. No. 7,052,686. Specific reaction conditions contemplated for use herein are set forth in the Experimental section.

Pegylation most frequently occurs at the alpha amino group at the N-terminus of the polypeptide, the epsilon amino group on the side chain of lysine residues, and the imidazole group on the side chain of histidine residues. Since most recombinant polypeptides possess a single alpha and a number of epsilon amino and imidazole groups, numerous positional isomers can be generated depending on the linker chemistry. General pegylation strategies known in the art can be applied herein.

Conjugation of one or more of the polypeptide sequences of the present disclosure to PEG having a spacer can be carried out by various conventional methods. For example, the conjugation reaction can be carried out in solution at a pH of from 5 to 10, at temperature from 4° C. to room temperature, for 30 minutes to 20 hours, utilizing a molar ratio of reagent to protein of from 4:1 to 30:1. Reaction conditions can be selected to direct the reaction towards producing predominantly a desired degree of substitution. In general, low temperature, low pH (e.g., pH=5), and short reaction time tend to decrease the number of PEGs attached, whereas high temperature, neutral to high pH (e.g., pH≥7), and longer reaction time tend to increase the number of PEGs attached. Various means known in the art can be used to terminate the reaction. In some embodiments, the reaction is terminated by acidifying the reaction mixture and freezing at, e.g., −20° C. Pegylation of various molecules is discussed in, for example, U.S. Pat. Nos. 5,252,714; 5,643,575; 5,919,455; 5,932,462; and 5,985,263. PEG-IL-10 is described in, e.g., U.S. Pat. No. 7,052,686.

Although the present disclosure contemplates the synthesis of pegylated IL-10 by any means known to the skilled artisan, the following provides several alternative synthetic schemes for producing mono-PEG-IL-10 and a mix of mono-/di-PEG-IL-10 is meant to be illustrative only. While both mono-PEG-IL-10 and a mix of mono-/di-PEG-IL-10 have many comparable properties, a mix of selectively pegylated mono- and di-PEG-IL-10 improves the yield of the final pegylated product (see, e.g., U.S. Pat. No. 7,052,686 and US Pat. Publn. No. 2011/0250163). In addition to leveraging her own skills in the production and use of PEGs (and other drug delivery technologies) suitable in the practice of the present disclosure, the skilled artisan is also familiar with many commercial suppliers of PEG-related technologies (and other drug delivery technologies). By way of example, NOF America Corp (Irvine, CA) supplies mono-functional Linear PEGs, bi-functional PEGs, multi-arm PESs, branched PEGs, heterofunctional PEGs, forked PEGs, and releasable PEGs; and Parchem (New Rochelle, NY) is a global distributor of PEG products and other specialty raw materials.

Exemplary PEG-IL-10 Synthetic Scheme No. 1. IL-10 is dialyzed against 10 mM sodium phosphate pH 7.0, 100 mM NaCl. The dialyzed IL-10 is diluted 3.2 times to a concentration of about 0.5 to 12 mg/mL using the dialysis buffer. Prior to the addition of the linker, SC-PEG-12K (Delmar Scientific Laboratories, Maywood, Ill.), one volume of 100 mM Na-tetraborate at pH 9.1 is added into 9 volumes of the diluted IL-10 to raise the pH of the IL-10 solution to 8.6. The SC-PEG-12K linker is dissolved in the dialysis buffer and the appropriate volume of the linker solution (1.8 to 3.6 mole linker per mole of IL-10) is added into the diluted IL-10 solution to initiate the pegylation reaction. The reaction is carried out at 5° C. in order to control the rate of the reaction, and the reaction solution is mildly agitated. When the mono-PEG-IL-10 yield, as determined by size exclusion HPLC (SE-HPLC), is close to 40%, the reaction is stopped by adding 1M glycine solution to a final concentration of 30 mM. The pH of the reaction solution is slowly adjusted to 7.0 using an HCl solution, and the reaction is 0.2 micron filtered and stored at −80° C.

Exemplary PEG-IL-10 Synthetic Scheme No. 2. Mono-PEG-IL-10 is prepared using methoxy-PEG-aldehyde (PALD-PEG) as a linker (Inhale Therapeutic Systems Inc., Huntsville, AL; also available from NOF America Corp (Irvine, CA)). PALD-PEG can have molecular weights of 5 KDa, 12 KDa, or 20 KDa. IL-10 is dialyzed and diluted as described above, except the pH of the reaction buffer is between 6.3 and 7.5. Activated PALD-PEG linker is added to reaction buffer at a 1:1 molar ratio. Aqueous cyanoborohydride is added to the reaction mixture to a final concentration of 0.5 to 0.75 mM. The reaction is carried out at room temperature (18-25° C.) for 15-20 hours with mild agitation. The reaction is quenched with 1M glycine. Yields are analyzed by SE-HPLC. Mono-PEG-IL-10 is separated from unreacted IL-10, PEG linker and di-PEG-IL-10 by gel filtration chromatography and characterized by RP-HPLC and bioassay (e.g., stimulation of IL-10-responsive cells or cell lines).

Exemplary PEG-IL-10 Synthetic Scheme No. 3. IL-10 (e.g., rodent or primate) is dialyzed against 50 mM sodium phosphate, 100 mM sodium chloride pH ranges 5-7.4. A 1:1-1:7 molar ratio of 5K PEG-propyladehyde is reacted with IL-10 at a concentration of 1-12 mg/mL in the presence of 0.75-30 mM sodium cyanoborohydride. Alternatively the reaction can be activated with picoline borane in a similar manner. The reaction is incubated at 5-30° C. for 3-24 hours. The pH of the pegylation reaction is adjusted to 6.3, 7.5 mg/mL of hIL-10 is reacted with PEG to make the ratio of IL-10 to PEG linker 1:3.5. The final concentration of cyanoborohydride is ~25 mM, and the reaction is carried out at 15° C. for 12-15 hours. The mono- and di-PEG IL-10 are the largest products of the reaction, with the concentration of each at ~45-50% at termination. The reaction can be quenched using an amino acid such as glycine or lysine or, alternatively, Tris buffers. Multiple purification methods can be employed such as gel filtration, anion and cation exchange chromatographies, and size exclusion HPLC (SE-HPLC) to isolate the desired pegylated IL-10 molecules.

In one embodiment of the invention, the modified IL-10 agent is a glycosylated IL-10. For purposes of the present disclosure, "glycosylation" is meant to broadly refer to the enzymatic process that attaches glycans to proteins, lipids or other organic molecules. The use of the term "glycosylation" in conjunction with the present disclosure is generally intended to mean adding or deleting one or more carbohydrate moieties (either by removing the underlying glycosylation site or by deleting the glycosylation by chemical and/or enzymatic means), and/or adding one or more glycosylation sites that may or may not be present in the native sequence. In addition, the phrase includes qualitative changes in the glycosylation of the native proteins involving a change in the nature and proportions of the various carbohydrate moieties present. Glycosylation can dramatically affect the physical properties (e.g., solubility) of polypeptides such as IL-10 and can also be important in protein stability, secretion, and subcellular localization. Glycosylated polypeptides can also exhibit enhanced stability or can improve one or more pharmacokinetic properties, such as half-life. In addition, solubility improvements can, for example, enable the generation of formulations more suitable for pharmaceutical administration than formulations comprising the non-glycosylated polypeptide.

Addition of glycosylation sites can be accomplished by altering the amino acid sequence of the IL-10 polypeptide. The alteration to the IL-10 polypeptide can be made, for example, by the addition of, or substitution by, one or more serine or threonine residues (for O-linked glycosylation sites) or asparagine residues (for N-linked glycosylation sites). The structures of N-linked and O-linked oligosaccharides and the sugar residues found in each type can be different. One type of sugar that is commonly found on both is N-acetylneuraminic acid (hereafter referred to as sialic acid). Sialic acid is usually the terminal residue of both N-linked and O-linked oligosaccharides and, by virtue of its negative charge, can confer acidic properties to the glycoprotein. A particular embodiment of the present disclosure comprises the generation and use of N-glycosylation variants. Examples of IL-10 polypeptides comprising modified amino acid sequences to incorporate glycosylation site are provided in, for example, Van Vlasselaer, et al., United States Patent Application Publication No. US20160068583 A1 published Mar. 10, 2016. The IL-10 polypeptide sequences of the present disclosure can optionally be altered through changes at the nucleic acid level, particularly by mutating the nucleic acid encoding the polypeptide at preselected bases such that codons are generated that will translate into the desired amino acids to facilitate the introduction of glycosylation sites.

In one embodiment of the invention, the modified IL-10 agent is polysialated IL-10. The term "polysialylation" refers to the conjugation of polypeptides to the naturally occurring, biodegradable $\alpha$-(2→8) linked polysialic acid ("PSA") in order to improve the polypeptides' stability and in vivo pharmacokinetics. PSA is a biodegradable, non-toxic natural polymer that is highly hydrophilic, giving it a high apparent molecular weight in the blood which increases its serum half-life. In addition, polysialylation of a range of peptide and protein therapeutics has led to markedly reduced proteolysis, retention of activity in vivo activity, and reduction in immunogenicity and antigenicity (see, e.g., G. Gregoriadis et al., Int. J. Pharmaceutics 300(1-2):125-30). Various techniques for site-specific polysialylation are available (see, e.g., T. Lindhout et al., PNAS 108(18)7397-7402 (2011)).

In one embodiment of the invention, the modified IL-10 agent is conjugated to albumin referred to herein as an "IL-10 albumin fusion." The term "albumin" as used in the context IL-10 albumin fusions include albumins such as human serum albumin (HSA), cyno serum albumin, and bovine serum albumin (BSA). According to the present disclosure, albumin can be conjugated to a IL-10 polypeptide (e.g., a polypeptide described herein) at the carboxyl terminus, the amino terminus, both the carboxyl and amino termini, and internally (see, e.g., U.S. Pat. Nos. 5,876,969 and 7,056,701). In the HSA-IL-10 polypeptide conjugates contemplated by the present disclosure, various forms of albumin can be used, such as albumin secretion pre-sequences and variants thereof, fragments and variants thereof, and HSA variants. Such forms generally possess one or more desired albumin activities. In additional embodiments, the present disclosure involves fusion proteins comprising a IL-10 polypeptide fused directly or indirectly to albumin, an albumin fragment, and albumin variant, etc., wherein the fusion protein has a higher plasma stability than the unfused drug molecule and/or the fusion protein retains the therapeutic activity of the unfused drug molecule. In some embodiments, the indirect fusion is effected by a linker, such as a peptide linker or modified version thereof.

Alternatively, the IL-10 albumin fusion comprises IL-10 polypeptides that are fusion proteins which comprise an albumin binding domain (ABD) polypeptide sequence and an IL-10 polypeptide. As alluded to above, fusion proteins which comprise an albumin binding domain (ABD) polypeptide sequence and an IL-10 polypeptide can, for example, be achieved by genetic manipulation, such that the nucleic acid coding for HSA, or a fragment thereof, is joined to the nucleic acid coding for the one or more IL-10 polypeptide sequences.

Additional suitable components and molecules for conjugation to an IL-10 agent include, for example, thyroglobulin; tetanus toxoid; Diphtheria toxoid; polyamino acids such as poly(D-lysine:D-glutamic acid); VP6 polypeptides of rotaviruses; influenza virus hemaglutinin, influenza virus nucleoprotein; Keyhole Limpet Hemocyanin (KLH); and hepatitis B virus core protein and surface antigen; or any combination of the foregoing.

The present disclosure contemplates conjugation of one or more additional components or molecules at the N- and/or C-terminus of a polypeptide sequence, such as another polypeptide (e.g., a polypeptide having an amino acid sequence heterologous to the subject polypeptide), or a carrier molecule. Thus, an exemplary polypeptide sequence can be provided as a conjugate with another component or molecule.

An IL-10 polypeptide can also be conjugated to large, slowly metabolized macromolecules such as proteins; polysaccharides, such as sepharose, agarose, cellulose, or cellulose beads; polymeric amino acids such as polyglutamic acid, or polylysine; amino acid copolymers; inactivated virus particles; inactivated bacterial toxins such as toxoid from diphtheria, tetanus, cholera, or leukotoxin molecules; inactivated bacteria; and dendritic cells. Such conjugated forms, if desired, can be used to produce antibodies against a polypeptide of the present disclosure.

Additional candidate components and molecules for conjugation include those suitable for isolation or purification. Particular non-limiting examples include binding molecules, such as biotin (biotin-avidin specific binding pair), an antibody, a receptor, a ligand, a lectin, or molecules that comprise a solid support, including, for example, plastic or polystyrene beads, plates or beads, magnetic beads, test strips, and membranes.

In certain embodiments, the amino- or carboxyl-terminus of an IL-10 polypeptide sequence of the present disclosure can be fused with an immunoglobulin Fc region (e.g., human Fc) to form a fusion conjugate (or fusion molecule). Fc fusion conjugates have been shown to increase the systemic half-life of biopharmaceuticals, and thus the biopharmaceutical product can require less frequent administration. Fc binds to the neonatal Fc receptor (FcRn) in endothelial cells that line the blood vessels, and, upon binding, the Fc fusion molecule is protected from degradation and re-released into the circulation, keeping the molecule in circulation longer. This Fc binding is believed to be the mechanism by which endogenous IgG retains its long plasma half-life. More recent Fc-fusion technology links a single copy of a biopharmaceutical to the Fc region of an antibody to optimize the pharmacokinetic and pharmacodynamic properties of the biopharmaceutical as compared to traditional Fc-fusion conjugates.

The present disclosure contemplates the use of other modifications, currently known or developed in the future, of IL-10 agents to improve one or more properties. Examples include hesylation, various aspects of which are described in, for example, U.S. Patent Appln. Nos. 2007/0134197 and 2006/0258607, and IL-10 polypaptide fusion molecules comprising SUMO as a fusion tag (LifeSensors, Inc.; Malvern, PA).

The present disclosure also contemplates IL-10 agents wherein the IL-10 polypeptide is a fusion protein of an IL-10 polypeptide and PEG mimetics. Polypeptide PEG mimetics have been developed that retain the attributes of PEG (e.g., enhanced serum half-life) while conferring several additional advantageous properties. By way of example, simple polypeptide chains (comprising, for example, Ala, Glu, Gly, Pro, Ser and Thr) capable of forming an extended conformation similar to PEG can be produced recombinantly already fused to the peptide or protein drug of interest (e.g., Amunix' XTEN technology; Mountain View, CA). IL-10 agents comprising fusion proteins of such polypeptide sequences may be generated by recombinant means by expression of a nucleic acid sequence encoding this fusion protein obviating the need for additional conjugation step during the manufacturing process. Moreover, established molecular biology techniques enable control of the side chain composition of the polypeptide chains, allowing optimization of immunogenicity and manufacturing properties.

Linkers and their use have been described above. Any of the foregoing components and molecules used to modify the polypeptide sequences of the present disclosure can optionally be conjugated to an IL-10 agent or IL-10 polypeptide via a linker. Suitable linkers include "flexible linkers" which are generally of sufficient length to permit some movement between the modified polypeptide sequences and the linked components and molecules. The linker molecules are generally about 6-50 atoms long. The linker molecules can also be, for example, aryl acetylene, ethylene glycol oligomers containing 2-10 monomer units, diamines, diacids, amino acids, or combinations thereof. Suitable linkers can be readily selected and can be of any suitable length, such as 1 amino acid (e.g., Gly), 2, 3, 4, 5, 6, 7, 8, 9, 10, 10-20, 20-30, 30-50 or more than 50 amino acids.

Examples of flexible linkers include glycine polymers $(G)_n$, glycine-serine polymers (for example, $(GS)_n$, $GSGGS_n$ (SEQ ID NO:9) and $GGGS_n$ (SEQ ID NO:10), where n is an integer of at least one), glycine-alanine polymers, alanine-serine polymers, and other flexible linkers. Glycine and glycine-serine polymers are relatively unstructured, and therefore can serve as a neutral tether between components.

Further examples of flexible linkers include glycine polymers $(G)_n$, glycine-alanine polymers, alanine-serine polymers, glycine-serine polymers (for example, $(G_mS_o)_n$, $(GSGGS)_n$(SEQ ID NO:28), $(G_mS_oG_m)_n$, $(G_mS_oG_mS_oG_m)_n$ (SEQ ID NO:29), $(GSGGS_m)_n$ (SEQ ID NO:30), $(GSGS_mG)_n$(SEQ ID NO:31) and $(GGGS_m)_n$(SEQ ID NO:32), and combinations thereof, where m, n, and o are each independently selected from an integer of at least 1 to 20, e.g., 1-18, 2-16, 3-14, 4-12, 5-10, 1, 2, 3, 4, 5, 6, 7, 8, 9, or 10), and other flexible linkers. Glycine and glycine-serine polymers are relatively unstructured, and therefore may serve as a neutral tether between components. Examples of flexible linkers include, but are not limited to GGSG (SEQ ID NO:33), GGSGG (SEQ ID NO:34), GSGSG (SEQ ID NO:35), GSGGG (SEQ ID NO:36), GGGSG (SEQ ID NO:37), and GSSSG (SEQ ID NO:38).

Additional flexible linkers include glycine polymers $(G)_n$ or glycine-serine polymers (e.g., $(GS)_n$, $(GSGGS)_n$(SEQ ID NO:9), $(GGGS)_n$(SEQ ID NO:10) and $(GGGGS)_n$(SEQ ID NO:39), where n=1 to 50, for example, 1, 2, 3, 4, 5, 6, 7, 8, 9, 10, 10-20, 20-30, 30-50. Exemplary flexible linkers include, but are not limited to GGGS (SEQ ID NO:40), GGGGS (SEQ ID NO:41), GGSG (SEQ ID NO:33), GGSGG (SEQ ID NO:34), GSGSG (SEQ ID NO:35), GSGGG (SEQ ID NO:36), GGGSG (SEQ ID NO:37), and GSSSG (SEQ ID NO:38). A multimer (e.g., 1, 2, 3, 4, 5, 6, 7, 8, 9, 10, 10-20, 20-30, or 30-50) of these linker sequences may be linked together to provide flexible linkers that may be used to conjugate a heterologous amino acid sequence to the polypeptides disclosed herein. As described herein, the heterologous amino acid sequence may be a signal sequence and/or a fusion partner, such as, albumin, Fc sequence, and the like.

Treatment of Neoplastic Disease:

The present disclosure contemplates the administration of the combinations of IL-10 agents (e.g., PEG-IL-10) in combination with one or more immune checkpoint pathway modulators(s) for the treatment and/or prevention neoplastic disease in a subject as well as diseases, disorders or conditions associated with neoplastic disease.

The compositions and method of the present disclosure are particularly suited for treatment of neoplastic conditions for which PD1 pathway inhibitors have demonstrated clinical effect in human beings either through FDA approval for treatment of the disease or the demonstration of clinical efficacy in clinical trials including but not limited to melanoma, non-small cell lung cancer, small cell lung cancer, head and neck cancer, renal cell cancer, bladder cancer, ovarian cancer, uterine endometrial cancer, uterine cervical cancer, uterine sarcoma, gastric cancer, esophageal cancer, DNA mismatch repair deficient colon cancer, DNA mismatch repair deficient endometrial cancer, hepatocellular carcinoma, breast cancer, Merkel cell carcinoma, thyroid cancer, Hodgkins lymphoma, follicular lymphoma, diffuse large B-cell lymphoma, mycosisfungoides, peripheral T-cell lymphoma.

Therapeutic responses to immune checkpoint pathway inhibitors generally manifest themselves much later than responses to traditional chemotherapies such as tyrosine kinase inhibitors. In some instance, it can take six months or more after treatment initiation with immune checkpoint pathway inhibitors before objective indicia of a therapeutic response are observed. In addition, in some cases involving anti-CTLA4 antibody therapy, metastatic lesions actually increase in size on computed tomography (CT) or magnetic resonance imaging (MRI) scans before subsequently regressing [See, e.g., Pardoll, (2012) Nature Rev. Cancer 12:252-64]. Therefore, a determination as to whether treatment with an immune checkpoint pathway inhibitors(s) in combination with an IL-10 agent of the present disclosure (e.g., PEG-IL-10) must be made over a time-to-progression that is frequently longer than with conventional chemotherapies. The desired response can be any result deemed favorable under the circumstances. In some embodiments, the desired response is prevention of the progression of the disease, disorder or condition, while in other embodiments the desired response is a regression or stabilization of one or more characteristics of the disease, disorder or conditions (e.g., reduction in tumor size). In still other embodiments, the desired response is reduction or elimination of one or more adverse effects associated with one or more agents of the combination.

The determination of clinical efficacy in the treatment of cancer is generally associated with the achievement of one or more art recognized parameters such as reduction in lesions particularly reduction of metastatic lesion, reduction in metastatsis, reduction in tumor volume, improvement in ECOG score, and the like. Determining response to treatment can be assessed through the measurement of biomarker that can provide reproducible information useful in any aspect of IL-10 or immune checkpoint pathway modulator, including the existence and extent of a subject's response to such therapy and the existence and extent of untoward effects caused by such therapy. By way of example, but not limitation, biomarkers associated with PD1/PDL1 include enhancement of IFNγ, and upregulation of granzyme A, granzyme B, and perforin; biomarkers associated with BTLA include an increase in CD8+ T cell number and function; biomarkers associated with CTLA4 include enhancement of IFNγ, upregulation of granzyme A, granzyme B, and perforin, and an increase in ICOS expression on CD8+ T cells; biomarkers associated with TIM3 include upregulation of granzyme A, granzyme B, and perforin; and biomarkers associated with LAG3 include enhancement of IL-10 expressing $T_{Reg}$ cells. Expression of the effector molecules IP-10 (Inducible Protein 10) and MIG (Monokine Induced by IFNγ) are known to be increased in certain IL-10-expressing tumors by either LPS or IFNγ; these effector molecules can also be leveraged as potential serum biomarkers that may be enhanced by the combinatorial therapies described herein. The response to treatment may be characterized by conventional measures of clinical efficacy may be employed such as Complete Response (CR), Partial Response (PR), Stable Disease (SD) and with respect to target lesions, Complete Response (CR)," Incomplete Response/Stable Disease (SD) as defined by RECIST as well as immune-related Complete Response (irCR), immune-related Partial Response (irPR), and immune-related Stable Disease (irSD) as defined Immune-Related Response Criteria (irRC) may be considered to evidence efficacy in the treatment of neoplastic disease.

Further embodiments comprise a method or model for determining the optimum amount of an agent(s) in a combination. An optimum amount can be, for example, an amount that achieves an optimal effect in a subject or subject population, or an amount that achieves a therapeutic effect while minimizing or eliminating the adverse effects associated with one or more of the agents. In some embodiments, the combination of IL-10 and immune checkpoint pathway inhibitors(s) itself is known to be, or has been determined to be, effective in treating or preventing a disease, disorder or condition described herein (e.g., a cancerous condition) in a subject (e.g., a human) or a subject population, and an amount of one agent is titrated while the amount of the other agent(s) is held constant. By manipulating the amounts of the agent(s) in this manner, a clinician is able to determine the ratio of agents most effective for, for example, treating a particular disease, disorder or condition, or eliminating the adverse effects or reducing the adverse effects such that are acceptable under the circumstances.

Perhaps the most well studied immunotherapy with the greatest clinical experience has been obtained with the anti-PD1 monoclonal antibodies pembrolizumab (Keytruda®) and nivolumab. These products have demonstrated significant effectiveness and now currently enjoy multiple approvals for a wide variety of cancers. The clinical experience with these agents has demonstrated a series of parameters which point to a greatest chance of success. Anti-PD1 therapy has demonstrated highest levels of effectiveness in those tumors where there are high levels of expression of PDL1 Garon et al. (2015) New England Journal of Medicine 372:2018-2028), where the tumor has a tumor mutational burden (Rizvi et al., Science (2015) Science 348:124-128; Carbone et al. (2017) New England Journal of Medicine 376:2415-2426), where there are high levels of CD8+ T cell in the tumor (Tumeh et al., (2014) Nature 515:568-571), an immune activation signature associated with IFNγ (Prat et al. (2017) Cancer Research 77(13): OF1-OF11), Cancer Res. 2017; Ayers et al (2107) J. Clinical Investigation 127:2930-2940), and the lack of metastatic disease particularly liver metastasis (Tumeh et al. (2017) Cancer Imm. Research 5:417-424); Pillai et al. (2017)) J. Clin. Oncology 34:15 suppl. e20665-e20665. These factors limit the effectiveness of PD1 therapy to a comparatively small range of tumors. A wide variety of tumors have low neo-antigen burden with rare neoantigen specific CD8+t cells, and tumors with high neo-antigen burden have been eventually escape ICIs. In other situations, there is an Immune Desert in the tumor microenvironment where T-cells have exhausted and apoptosed, the lack of T cell expression leads low levels of granzyme and IFNγ expression in the tumor. IL-10 monotherapy addresses many of these parameters. IL-10 has been observed to increase activity of increase activity of intratumoral CD8+ T cells, increase levels of granzymes, FasL and IFNγ. Mumm et al., (2011) Cancer Cell 20(6):781-796; Emmerich, et al., (2012) Cancer Research 72(14):3570-81; Oft, (2014) Cancer Immunology Research. 72(14):3570-81). Because of the established utility of IL-10 in addressing these hurdles we evaluated an IL-10 agent in combination with anti-PD1 Mab therapy.

AM0010, a PEGylated form of hIL-10 comprising a mixture of mono- and di-PEGylated IL-10 has been evaluated in multiple clinical trials and has been shown to well tolerated as a single agent (144 patients with excellent compliance up to 2.5 years after initiation of treatment. The term AM0010 refers to a recombinant human interleukin 10 (rHuIL-10) comprising a mixture of mono- and di-PEGylated IL-10 polypeptdes and employing 5 kDa polyethylene glycol (PEG) attached via a linker to the N-terminus of the IL-10 polypeptide. AM0010 is a non-glycosylated homodimeric protein composed of two non-covalently associated rHuIL-10 polypeptide monomers, where each monomer is composed of 161 amino acids, including an N-terminal methionine not present in native human IL-10 polypeptide arising from direct recombinant production, each monomer comprising two intramolecular disulfide linkages, the first between cysteines at positions 13 and 109 and the second between cysteines at positions 63 and 115 of the 161 amino acid rHuIL-10 polypeptide (corresponding to cysteines at positions 12 and 108 and positions 62 and 114 of the naturally occurring hIL-10 polypeptide). Observed TrAEs from AM0010 monotherapy include were manageable and reversible and there have been no durable autoimmune related TrAEs, such as colitis, pneumonitis, hepatitis or endocrine disorders. In these studies, AM0010 monotherapy at a daily subcutaneous dose of 20 micrograms/kg induces objective responses in renal cell carcinoma (RCC, 25% ORR), uveal melanoma and a CR in Cutaneous T cell lymphoma with durable responses up to 2.5 years and prolonged stable disease in CRC and PDAC.

Without AM0010, CD8+ T cells recognize the tumor cell, become exhausted and undergo apoptosis. With AM0010, tumor recognizing CD8+ T cells are activated and proliferate. AM0010 inhibits CD8+ T cell apoptosis and induces Granzymes and FasL which induces tumor cell death and AM0010 primes a sustained immune memory. The primary dose of AM10 monotherapy is 2 mg or (20 micrograms/kg) administered subcutaneously daily.

In order to evaluate the combination of and IL-10 agent with a immune checkpoint modulator, a clinical trial to was performed involving 57 human subjects suffering from renal cell carcinoma (RCC) to compare AM0010 monotherapy to combinations of two different doses of AM0010 each in combination with the anti-PD1 immune checkpoint pathway antagonis antibodies pembrolizumab and nivolumab. The patient population and study design are summarized in the Table 3 below.

TABLE 3

RCC CLINICAL TRIAL DESIGN

| | Monotherapy 2 mg (20 μg/kg) N = 19 | AM0010 - 1 mg/2 mg (10/20 μg/kg) + Pembrolizumab N = 8 (+1*) | AM0010 - 1 mg/2 mg (10/20 μg/kg) + Nivolumab N = 29 |
|---|---|---|---|
| Median Age, years (range) | 61 (22, 68) | 54 (32, 75) | 66 (36, 77) |
| Sex, n (%) | | | |
| Male | 12 (63%) | 6 (67%) | 21 (72%) |
| Female | 7 (37%) | 3 (33%) | 8 (28%) |
| ECOG Performance Status, n (%) | | | |
| 0 | 11 (58%) | 3 (33%) | 9 (31%) |
| 1 | 8 (42%) | 6 (67%) | 20 (69%) |
| Prior Therapy, median (range) | 3 (0-7) | 2 (0-5) | 1 (1-3) |
| IMDC (intermediate - poor) | 18 (95%) | 8 (89%) | 27 (93%) |

*1 patient with prior AM0010 monotherapy, included in safety but not in efficacy analysis Pembrolizumab (Keytruda®, Merck and Co, Rahway NJ) was administered in at a dose of 160 mg (2 mg/kg) administered intravenously every three weeks. Nivolumab (Opdivo®, BristolMyers Squibb, Princeton NJ) was administered in accordance with the revised label approved dose of 240 mg (3 mg/kg) administered intravenously every two weeks. AM0010 was administered subcutaneously daily at a dose of 20 micrograms/kg in the monotherapy arm, and daily subcutaneously at each of 10 micrograms/kg and 20 micrograms/kg in each of the anti-PD1 combination therapy arms. The results of this study are summarized in the Table 4 and Table 5 below and in FIG. 4 of the attached drawings.

TABLE 4

| RCC CLINICAL TRIAL RESULTS | Monotherapy 2 mg (20 μg/kg) N = 16 | AM0010 - 1 mg (10 μg/kg) + Pembrolizumab N = 5 | AM0010 - 2 mg (20 μg/kg) + Pembrolizumab N = 3 | AM0010 - 1 mg (10 μg/kg) + Nivolumab N = 2 | AM0010 - 2 mg (20 μg/kg) + Nivolumab N = 27 |
|---|---|---|---|---|---|
| Partial Response (ORR) | 4 (25%) | 2 (40% | 2 (67%) | 2 (100%) | 66 (36, 77) |
| CR | | 1 (20%) | 1 (33%) | NR | NR |
| DCR | 12 (63%) | 5 (100%) | 3 (100%) | 2 (100%) | 19 (70%) |

1 patient with prior AM0010 monotherapy, included in safety but not in efficacy analysis

TABLE 5

RCC CLINICAL TRIAL RESULTS
Results of Clinical Evaluation of AM0010 in Combination with Anti-PD1 Antibodies

| Disease | Treatment Combo (n = Evaluable Patients/ Enrolled Patients) | Prior Therapies Median (Range) | DCR n (%) | ORR (%) | CR (%) | mPFS (Months) | mOS (Months) |
|---|---|---|---|---|---|---|---|
| RCC | AM0010 (n = 16/19) | 3 (0-7) | 9 (56%) | 4 (25%) | — | 1.9 | 9.8[1] |
| | AM0010 + pembrolizumab (n = 8/8) | 2 (0-5) | 8 (100%) | 4 (50%) | 2[4] (25%) | 16.7 | NR[2] |
| | AM0010 + nivolumab (n = 26/29) | 1 (1-3) | 21 (81%) | 11 (42%)[2] | NR | NR[3] | NR[3] |
| | Nivolumab, historical data[5] | 1 | 57-65% | 20-22% | 1 | 2.7-4.2 | 25 |

[1]ORR numbers as of Oct. 29, 2017
[2]Study in progress. Numbers as of Aug. 11, 2017. Median follow-up 26.75 months (range 12.3-29.8);
[3]Study in progress. Numbers as of Aug. 11, 2017. Median follow-up 11.1 months (range 0.5-17.3);
[4]2 partial responses with 100% reduction in measurable disease; NR not reached
[5]Motzer, et al., Nivolumab for Metastatic Renal Cell Carcinoma: Results of a Randomized Phase II Trial, (2015) *Journal of Clinical Oncology* 33(13): 1430-1437

As can be seen from the data presented above, 56% of the evaluable patients in the AM0010 monotherapy arm exhibited a durable clinical response (DCR) with an objective response rate (ORR) of approximately 25%. However, the foregoing data show that combination of AM0010 with PD1 checkpoint inhibitors results in significantly improved results as compared to AM0010 monotherapy or anti-PD1 monotherapy (based on literature reported results. The combination of AM0010 with pembrolizumab (Keytruda®) showed a DCR in 100% of patients who received AM0010 in combination with pembrolizumab at both the 10 and 20 microgram/kg doses and an overall ORR of 50%. Similarly, in patients who received nivolumab in combination with AM0010 at the 10 microgram/kg dose showed a 100% DCR and 70% of patients at the 20 microgram/kg dose of AM0010 are showed a DCR of 81% with a combined ORR of 42%. Literature reports of the response rates in RCC in following administration of nivolumab in RCC demonstrate a DCR of approximately 57-65% with an ORR of approximately 20-22% (Motzer, et al., *Nivolumab for Metastatic Renal Cell Carcinoma: Results of a Randomized Phase II Trial*, (2015) Journal of Clinical Oncology 33(13):1430-1437) and an ORR of 25% (Mazza, et al. (2017) *Nivolumab in renal cell carcinoma: latest evidence and clinical potential*, Therapeutic Advances in Medical Oncology Vol. 9(3) 171-18). These data demonstrate that the combination of and IL-10 agent (AM0010) in combination with an immune checkpoint pathway inhibitor (e.g. nivolumab and pembrolizumab) results in a significant improvement in therapeutic outcome in the treatment of renal cell carcinoma in human subjects.

A second focus of this study was to evaluate adverse events associated with the combination therapy. The results of the adverse events arising from this study are shown in Table 6 below.

TABLE 6

RCC TRIAL ADVERSE EVENTS

| | Grade 1/2 | | Grade 3/4 | |
|---|---|---|---|---|
| AM0010 Dose | 10 μg/kg | 20 μg/kg | 10 μg/kg | 20 μg/kg |
| Number of Patients | N = 6 | N = 32 | N = 6 | N = 32 |
| Blood and lymphatic system disorders | | | | |
| Anaemia | 3 (50.0) | 6 (18.8) | | 10 (31.3) |
| Histiocytosis haematophagic | | 1 (3.1) | | 1 (3.1) |
| Neutropenia | 0 (0.0) | 0 (0.0) | 1 (16.7) | 2 (6.3) |
| Splenomegaly | | 1 (3.1) | | 1 (3.1) |
| Thrombocytopenia | 2 (33.3) | 4 (12.5) | | 7 (21.9) |

TABLE 6-continued

RCC TRIAL ADVERSE EVENTS

| | Grade 1/2 | | Grade 3/4 | |
|---|---|---|---|---|
| AM0010 Dose | 10 μg/kg | 20 μg/kg | 10 μg/kg | 20 μg/kg |
| General disorders and administration site conditions | | | | |
| Chills | | 5 (15.6) | | |
| Fatigue | 4 (66.7) | 11 (34.4) | | 1 (3.1) |
| Malaise | | 1 (3.1) | | 1 (3.1) |
| Night sweats | 1 (16.7) | 3 (9.4) | | |
| Oedema | | 1 (3.1) | | 1 (3.1) |
| Pyrexia | 1 (16.7) | 11 (34.4) | | |
| Investigations | | | | |
| Alanine aminotransferase increased | | 4 (12.5) | 1 (16.7) | 1 (3.1) |
| Amylase increased | | 1 (3.1) | | 1 (3.1) |
| Aspartate aminotransferase increased | | 5 (15.6) | 1 (16.7) | 1 (3.1) |
| Metabolism and nutrition disorders | | | | |
| Decreased appetite | 1 (16.7) | 2 (6.3) | | |
| Hyperglycaemia | | 3 (9.4) | | |
| Hypertriglyceridaemia | 2 (33.3) | 5 (15.6) | 1 (16.7) | 5 (15.6) |
| Hypoalbuminaemia | | 2 (6.3) | | |
| Musculoskeletal and connective tissue disorders | | | | |
| Arthralgia | | 5 (15.6) | | |
| Myalgia | | 8 (25.0) | | |
| Nervous system disorders | | | | |
| Headache | | 5 (15.6) | | |
| Skin and subcutaneous tissue disorders | | | | |
| Pruritus | | 8 (25.0) | 1 (16.7) | 1 (3.1) |
| Rash | 1 (16.7) | 7 (21.9) | | |
| Rash maculo-papular | 1 (16.7) | 6 (18.8) | 1 (16.7) | |

The foregoing data demonstrates that the combination of AM10 and anti-PD-1 is well tolerated in renal cell carcinoma patients in at each dose of AM0010 in combination with pembrolizumab (2 mg/kg, q3w) or nivolumab (3 mg/kg, q2w), Although all Grade 3 and Grade 4 adverse events were transient and resolved, in light of the foregoing efficacy data, a dose of 10 meg/kg of AM10 in combination with a PD1 pathway inhibitor appears preferable based on this limited clinical data.

In parallel with the foregoing RCC study, another clinical study was conducted in subjects suffering from non-small cell lung cancer (NSCLC) to evaluate the combination of an IL-10 agent (AM0010) in combination with the PD1 immune checkpoint pathway inhibitors (e.g. nivolumab and pembrolizumab) in human subjects. In this study the PDL1 expression levels of tumors samples was assessed. The study design was similar to the foregoing RCC study with the patient population being anti-PD1 therapy naïve prior to initiation of the study. The study design and patient population data is summarized in Table 7 below. "Low PD-L1 expression" refers to a level of cell-surface PD-L1 expression of less than 1%; "intermediate PD-L1 expression" refers to a level of cell surface PD-L1 expression of 1% to 49%; and "high PD-L1 expression" refers to a level of cell surface PD-L1 expression of equal to or greater than 050%, where PD-L1 expression is assessed in accordance with the methodologies available in the art, such as in Rizzi et al. (2015) Science 348:124-128.

TABLE 7

NSCLC CLINICAL TRIAL DESIGN

| | AM0010 Monotherapy 2 mg (20 μg/kg) N = 9 | AM0010 1 mg (10 μg/kg) + Pembrolizumab N = 5 | AM0010 2 mg (20 μg/kg) + Nivolumab N = 29 |
|---|---|---|---|
| Median Age, years (range) | 58 (44, 68) | 74 (56, 80) | 62 (40, 84) |
| Sex, n (%) | | | |
| Male | 2 (22%) | 4 (80%) | 14 (48%) |
| Female | 7 (78%) | 1 (20%) | 15 (52%) |
| ECOG Performance Status, n (%) | | | |
| 0 | 3 (33%) | 0 (0%) | 8 (25%) |
| 1 | 6 (66%) | 5 (100%) | 21 (75%) |

TABLE 7-continued

| NSCLC CLINICAL TRIAL DESIGN | | | |
|---|---|---|---|
| | AM0010 Monotherapy 2 mg (20 μg/kg) N = 9 | AM0010 1 mg (10 μg/kg) + Pembrolizumab N = 5 | AM0010 2 mg (20 μg/kg) + Nivolumab N = 29 |
| Histology type, n (%) | | | |
| Squamous | 0 | 2 (40%) | 4 (14%) |
| Non-squamous | 9 (100%) | 3 (60%) | 24 (83%) |
| Unknown | 0 | 0 | 1 (3%) |
| Prior Therapy, median (range) | 3 (1-7) | 2 (0-5) | 2 (1-3) |
| PD-L1+ Status, n (%) | 5 tested for PD-L1<br><1% PD-L1+: n = 5 (100%) | 4 tested for PD-L1<br><1% PD-L1+: n = 4 (100%) | 20 tested for PD-L1<br><1% PD-L1+: n = 12 (60%)<br>1-49% PD-L1+: n = 3 (15%)<br>≥50% Pd-L1+: n = 5 (25%) |

Pembrolizumab (Keytruda®) was administered in at a dose of 160 mg (2 mg/kg) administered intravenously every three weeks. Nivolumab (Opdivo®) was administered in accordance with the revised label approved dose of 240 mg (3 mg/kg) administered intravenously every two weeks. AM0010 was prepared in substantial as above and administered subcutaneously daily at a dose of 20 micrograms/kg in the monotherapy arm, and daily subcutaneously at each of 10 micrograms/kg and 20 micrograms/kg in each of the anti-PD1 combination therapy arms. The results of this study are summarized in the Table 8 below and FIG. 3 of the attached drawings.

TABLE 8

| NSCLC CLINICAL TRIAL RESULTS | | | | | | |
|---|---|---|---|---|---|---|
| Disease | Treatment Combo (n = Evaluable Patients/ Enrolled Patients) | Prior Therapies Median (Range) | DCR (%) | ORR (%) | mPFS (Months) | mOS (Months) |
| NSCLC | AM0010 (n = 7/9)[1] | 3 (1-7) | 57% | — | 1.7 | 15.4[3] |
| | AM0010 + pembrolizumab (n = 5/5)[2] | 2 (0-5) | 100% | 2 (40%) | 10.9 | NR[4] |
| | AM0010 + nivolumab (n = 22/29) | 2 (1-3) | 82% | 9 (41%)[3] | NR[5] | NR[5] |
| | pembrolizumab, historical data | 1 | 41% | 19.4% | 3.0[6] | 9.3[6] |

[1]5 of 5 patients tested are PD-L1 negative;
[2]4 of 4 patients tested are <1% PD-L1+;
[3]ORR numbers of Oct. 29, 2017;
[4]Study in progress. Numbers as of Aug. 11, 2017. 60% alive, median follow-up 28.4 months (range 26.5-30.3)
[5]Study in progress. Numbers as of Aug. 11, 2017. Median follow-up 16.1 months (range 5.6-30.3);
[6]Garon et al (2015) N Engl J Med 372: 2018-2028, previously treated patients;
NR: Not reached As can be seen from the data presented above, 57% of the evaluable patients (7/9) in the AM0010 monotherapy arm exhibited a durable clinical response (DCR). However, the data show that combination of AM0010 with PD1 checkpoint inhibitors provides significantly enhanced therapeutic results as compared to AM0010 monotherapy or anti-PD1 monotherapy (based on literature reported results). The combination of AM0010 with pembrolizumab (Keytruda®) showed a DCR in 100% of patients who received AM0010 in combination with pembrolizumab at both the 10 and 20 microgram/kg doses (data for both AM0010 doses combined) and an overall ORR of 40% (data for both AM0010 doses combined). Similarly, in patients who received nivolumab in combination with AM0010 at the 10 and 20 microgram/kg doses showed a DCR of 82% (data for both AM0010 doses combined) with an ORR of 42% (data for both AM0010 doses combined). Literature reports of the response rates in NSCLC in following administration of pembrolizumab suggest a DCR of 41% for the anti-PD1 monotherapy and ORR of approximately 20-22% (Garon, et al. (2015) NEJM 372:2018-28). These data demonstrate that the combination of and IL-10 agent (AM0010) in combination with an immune checkpoint pathway inhibitor (e.g. nivolumab and pembrolizumab) results in a significant improvement in therapeutic outcome in the treatment of non-small cell lung cancer in human subjects.

Of significant note was the response in this study observed based on PDL1 status. As previously noted, low PDL1 status is typically associated with poor prognosis in response to anti-PD1 pathway inhibitors such as pembrolizumab and nivolumab. The data relating to the ORR as a factor of PDL1 expression is summarized in the table below.

TABLE 9

NSCLC TRIAL RESULTS RELATIVE TO PDL1 EXPRSSION
Effect of PDL1 Status on ORR in Response to Combo AM0010 anti-Pd1 Mabs

| | | ORR by PD-L1 status (%) | | |
|---|---|---|---|---|
| Disease | Treatment Combo | <1% Pd-L1+ | 1-49% Pd-L1+ | ≥50% Pd-L1+ |
| NSCLC | AM0010 + anti-PD-1 mAbS (n = 20 tested for PD-L1 status) | 33% (n = 12) | 67% (n = 3) | 80% (n = 5) |
| | Pembrolizumab historical data (Garon, NEJM: 2015) | 9.1% | 15.6% | 43.9% |

As shown by the foregoing data, by combining AM0010 with the anti-PD1 antibodies pembrolizumab and nivolumab (data aggregated above) demonstrates a significant increase in ORR at all expression levels of PDL1. However, perhaps most notably is that response rate in NSCLC at low (<1%) PDL1 expression levels where the combination showed an ORR of 33% (a 362% increase in ORR versus pembrolizumab monotherapy historical data) and at intermediate (1%-49%) PDL1 expression levels showing an ORR of 67% (a 429% improvement in ORR versus pembrolizumab monotherapy historical data). These data demonstrate that the combination of and IL-10 agent (AM0010) in combination with an immune checkpoint pathway inhibitor (e.g. nivolumab and pembrolizumab) results in a significant improvement in therapeutic outcome in the treatment of non-small cell lung cancer in human subjects, even in tumor low or intermediate expression levels of PDL1.

Effect in Tumors with Low Tumor Mutation Burden:

Another parameter that was evaluated in the course of the NSCLC study described above was tumor mutation burden. As reported by Carbone, et al., 23 of 111 (21%) of NSCLC patients with low or intermediate tumor mutational burden had a reduced response rate to nivolumab alone (n=23 of 111, 21%). In contrast, five of eight patients (60%) with low or intermediate TMB exhibited a PR to the combination of AM0010 with anti-PD1 as summarized in Table 10 below and FIG. 1 of the attached drawings.

TABLE 10

NSCLC TRIAL RESULTS RELATIVE TO TUMOR MUTATION BURDEN

| | | Responses by TMB status | | |
|---|---|---|---|---|
| Disease | PD-L1+ | Low TBM (<100 mut/Mb) | Medium TMB (100-243 mut/Mb) | High TMB (>243 mut/Mb) |
| NSCLC | PD-L1 0-49% | 1 SD (n = 1) | 2 PR (n = 3) | 1 PR (n = 2) |
| | PD-L1+ ≥50% | 3 PR (n = 4) | | |

These data demonstrate that the combination of and IL-10 agent (AM0010) in combination with an immune checkpoint pathway inhibitor (e.g. nivolumab and pembrolizumab) results in a significant improvement in therapeutic outcome in the treatment of non-small cell lung cancer in human subjects having a low TMB, even in the presence of low or intermediate expression levels of PDL1, two factors recognized as mitigating against PD1 therapy.

Effect of AM0010 in Combination with Pembrolizumab On Metastatic Disease

Metastasis is the primary cause of cancer morbidity and mortality accounting for approximately 90% of cancer deaths. Chaffer & Weinberg (2011). A perspective on cancer cell metastasis, Science. 331:1559-64. Patients with liver metastasis have a lower overall response rate to immune checkpoint inhibition. Tumeh et al. (2017); Pillai et al (2017) supra. In the foregoing NSCLC study, an evaluation was made of liver metastasis and the results are presented in FIGS. 5 and 6 of the attached drawings. As illustrated, the combination of AM0010 with pembrolizumab resulted in a significant reduction in measurable liver metastatic lesions over the course of treatment.

Effect of AM0010 in Combination with Anti-PD1 Mab Therapy as a Function of IFNγ-Associated Gene Expression Profile As reported in the literature, patients with a low IFNγ-associated gene expression profile (e.g. expression of STAT1, HLA-DRA, CXCL9, IDO, IFNγ and CXCL10) have a reduced response rate to pembrolizumab (Prat et al. (2017) supra; Ayers et al. (2017) supra. As part of the NSCLC study above, the therapeutic response to the combination of AM0010 in combination with anti-PD1 mAb therapy in as a function of IFNg-associated gene expression profile was evaluated. The results are presented in FIG. 2 of the attached drawings. As illustrated, two patients (of five) with a low IFNγ-associated gene expression profile had a partial response on in response to the combination of AM0010 with anti-PD-1 mAb therapy with an additional 2 subject exhibiting stable disease for more than 6 months.

The foregoing clinical data generated in human subjects suffering from neoplastic disease demonstrate that the administration of an IL-10 agent in combination with the administration of at least one modulator of at least one immune checkpoint pathway, wherein the modulator is an agonists of positive immune checkpoint pathway or an antagonist of a negative immune checkpoint pathway, is effective in the treatment of neoplastic disease in mammalian subjects.

The foregoing clinical data generated in human subjects suffering from neoplastic disease demonstrate that the administration of an IL-10 agent in combination with the administration of at least one modulator of at least one immune checkpoint pathway, wherein the modulator is an agonists of positive immune checkpoint pathway or an antagonist of a negative immune checkpoint pathway, is effective in the treatment of neoplastic disease in mammalian subjects wherein the neoplasm has a low or intermediate tumor mutation burden.

The foregoing clinical data generated in human subjects suffering from neoplastic disease demonstrate that the administration of an IL-10 agent in combination with the administration of at least one modulator of at least one immune checkpoint pathway, wherein the modulator is an agonists of positive immune checkpoint pathway or an antagonist of a negative immune checkpoint pathway, is effective in the treatment of neoplastic disease in mammalian subjects wherein the neoplasm has a low or intermediate level of expression of the immune checkpoint molecule.

The foregoing clinical data generated in human subjects suffering from neoplastic disease demonstrate that the administration of an IL-10 agent in combination with the administration of at least one modulator of at least one immune checkpoint pathway, wherein the modulator is an agonists of positive immune checkpoint pathway or an antagonist of a negative immune checkpoint pathway, is effective in the treatment of metastatic neoplastic disease in mammalian subjects.

The foregoing clinical data generated in human subjects suffering from neoplastic disease demonstrate that the administration of an IL-10 agent in combination with the administration of at least one modulator of at least one immune checkpoint pathway, wherein the modulator is an agonists of positive immune checkpoint pathway or an antagonist of a negative immune checkpoint pathway, is effective in the treatment of neoplastic disease in a subject with a low or intermediate IFNγ-associated gene expression profile, the IFNγ-associated gene expression profile comprising one or more of the genes selected from the group consisting of STAT1, HLA-DRA, CXCL9, IDO, IFNγ and CXCL10.

The present disclosure further provides methods for treating neoplastic disease with an IL-10 agent (e.g., PEG-IL-10), one or more immune checkpoint pathway modulators, and at least one additional therapeutic or diagnostic agent. Such further combinations are referred to as "supplementary combinations", "supplementary combination therapy", and agents that are added to combinations of IL-10 and one or more immune checkpoint pathway modulator(s) can be referred to as "supplementary agents."

Examples of such "supplementary agents" include chemotherapeutic agents. The term "chemotherapeutic agents" includes but is not limited to alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamime; nitrogen mustards such as chiorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside (Ara-C); cyclophosphamide; thiotepa; taxoids, e.g., paclitaxel and docetaxel; chlorambucil; gemcitabine; 6-thioguanine; mercaptopurine; methotrexate; platinum and platinum coordination complexes such as cisplatin and carboplatin; vinblastine; etoposide (VP-16); ifosfamide; mitomycin C; mitoxantrone; vincristine; vinorelbine; navelbine; novantrone; teniposide; daunomycin; aminopterin; xeloda; ibandronate; CPT 11; topoisomerase inhibitors; difluoromethylornithine (DMFO); retinoic acid; esperamicins; capecitabine; and pharmaceutically acceptable salts, acids or derivatives of any of the above. The term "chemotherapeutic agents" also includes anti-hormonal agents that act to regulate or inhibit hormone action on tumors such as anti-estrogens, including for example tamoxifen, raloxifene, aromatase inhibiting 4(5)-imidazoles, 4-hydroxytamoxifen, trioxifene, keoxifene, onapristone, and toremifene; and anti-androgens such as flutamide, nilutamide, bicalutamide, leuprolide, and goserelin; and pharmaceutically acceptable salts, acids or derivatives of any of the above. In some embodiments, the supplementary agent may be one or more chemical or biological agents identified in the art as useful in the treatment of neoplastic disease, including, but not limited to, a cytokines or cytokine antagonists such as IL-12, INFα, or anti-epidermal growth factor receptor, radiotherapy, antibodies against tumor antigens, a complex of a monoclonal antibody and toxin, a T-cell adjuvant, bone marrow transplant, or antigen presenting cells (e.g., dendritic cell therapy), anti-tumor vaccines, replication competent viruses, and CAR-t cells.

In such supplementary combination therapy, the various supplementary active agent(s) frequently have different mechanisms of action than IL-10 and/or the immune checkpoint pathway modulator(s). Such supplementary combination therapy can be especially advantageous by facilitating a dose reduction of one or more of the agents, thereby reducing or eliminating the adverse effects associated with one or more of the agents. Furthermore, such supplementary combination therapy can have an additive or synergistic therapeutic or prophylactic effect on the underlying disease, disorder, or condition. In some embodiments of the present disclosure the supplementary agent(s) is a diagnostic agent (s).

In some embodiments of the present disclosure, each of the IL-10 agent (e.g., PEG-IL-10), the immune checkpoint pathway modulator(s) and the supplementary agent(s) can be in a separate dosage form. By way of example, the PEG-IL-10 can be in a formulation suitable for SC administration, the immune checkpoint pathway inhibitors can be in a formulation suitable for IV administration, and the supplementary agent can be in a formulation suitable for oral administration; in this context, each of the agents can be housed separately or two or more of the agents can be housed together (e.g., as distinct components of a kit). In other embodiments of the present disclosure, two or more of the IL-10 agent (e.g., PEG-IL-10), the immune checkpoint pathway modulator(s) and the supplementary agent(s) are in the same dosage form. For example, the PEG-IL-10, the immune checkpoint pathway modulator(s), and the supplementary agent(s) can be formulated for IV administration; in this context, one or more of the agents can be co-formulated (e.g., as the active therapeutic agents in a syringe). The present disclosure encompasses pharmaceutically acceptable salts, acids or derivatives of any of the above.

In certain embodiments, the IL-10 agent, the immune checkpoint pathway modulator(s) and the supplemental agent(s) (e.g., a chemotherapeutic agent) are administered or applied in combination with the other agents, including sequentially, e.g., where the IL-10 agent is administered first, an immune checkpoint pathway inhibitors is administered second, and a supplemental agent is administered last. In other embodiments, the IL-10 agent, the immune checkpoint pathway modulator(s) and the supplemental agent(s) are administered simultaneously, e.g., where two of the agents are administered simultaneously and the third is administered either before or after. Regardless of whether the IL-10 agent, the immune checkpoint pathway modulator (s) and the supplemental agent(s) are administered sequentially, simultaneously, or some variation thereof, they are considered to be administered as supplementary combination therapy for purposes of the present disclosure.

The present disclosure contemplates the use of a dosing regimen for the supplementary combination therapy that may be acceptable, appropriate or optimal under the circumstances and does not result in the inducement of non-reversible Grade 4 or Grade 4 adverse event. The regimens described hereafter are exemplary, not exclusionary. In one embodiment, treatment with the IL-10 agent (e.g., PEG-IL-10), the immune checkpoint pathway modulator(s), and the supplemental agent(s) are maintained over a period of time. In another embodiment, treatment with the IL-10 agent, the immune checkpoint pathway modulator(s), and the supplemental agent(s) are reduced or continued over a period to time (e.g., when the subject is stable). In another embodiment, treatment with the supplemental agent(s) is reduced or discontinued (e.g., when the subject is stable), while treatment with the IL-10 agent and the immune checkpoint pathway modulator(s) is maintained at a constant dosing regimen. In a further embodiment, treatment with the supplemental agent(s) is reduced or discontinued (e.g., when the subject is stable), treatment with the IL-10 agent is reduced (e.g., lower dose, less frequent dosing or shorter treatment regimen), and treatment with the immune checkpoint pathway inhibitors is maintained at a constant dosing regimen. In a further embodiment, treatment with the supplemental agent(s) is reduced or discontinued (e.g., when the subject is stable), treatment with the IL-10 agent is reduced (e.g., lower dose, less frequent dosing or shorter treatment regimen), and treatment with the immune checkpoint pathway modulator(s) is maintained at a constant dosing regimen.

Administration:

The present disclosure contemplates the use of the IL-10 agents described herein (e.g., PEG-IL-10), and compositions thereof, in combination with one or more immune checkpoint pathway inhibitors to treat and/or prevent various diseases, disorders and conditions (e.g., cancers), and/or the symptoms thereof. In some embodiments, the IL10 agent is administered by parenteral injection, including subcutaneous injection in certain embodiments. The one or more immune checkpoint pathway modulator may also be administered by any route effective in view of the nature of the modulator and the immune checkpoint pathway to be modulated. In some embodiments, the IL-10 agent and the immune checkpoint pathway modulator(s) can be administered by the same route (e.g., IV), while in other embodiments they can be administered by different routes (e.g., the IL-10 agent can be administered subcutaneously and the immune checkpoint pathway modulator(s) can be administered intravenously.

In certain aspects of the present disclosure, such treatment or prevention is effected by utilizing particular dosing parameters that serve to minimize any adverse effects associated with administration of the individual therapies by themselves. By way of example, the addition of a PEG-IL-10 regimen to a regimen comprising ipilimumab (an anti-CTLA4 mAb) might allow a reduction of the amount of ipilimumab needed to achieve the therapeutic goal, thus mitigating ipilimumab's immune-mediated adverse reactions. The specific IL-10 and immune checkpoint pathway inhibitors(s) (along with, e.g., the therapeutic goal) influence the administration, dosing regimens, dosing parameters, etc. when used in combination.

The IL-10 agents (e.g., PEG-IL-10) and immune checkpoint pathway modulators of the present disclosure can be administered to a subject in an amount that is dependent upon, for example, the goal of the administration (e.g., the degree of resolution desired); the age, weight, sex, and health and physical condition of the subject the formulation being administered; the route of administration; and the nature of the disease, disorder, condition or symptom thereof. The dosing regimen can also take into consideration the existence, nature, and extent of any adverse effects associated with the agent(s) being administered. Effective dosage amounts and dosage regimens can readily be determined from, for example, safety and dose-escalation trials, in vivo studies (e.g., animal models), and other methods known to the skilled artisan.

The blood plasma levels of IL-10 agents in the methods described herein can be characterized in several manners, including: (1) a mean IL-10 agentt serum trough concentration above some specified level or in a range of levels; (2) a mean IL-10 agent serum trough concentration above some specified level for some amount of time; (3) a steady state IL-10 agent serum concentration level above or below some specified level or in a range of levels; or (4) a $C_{max}$ of the concentration profile above or below some specified level or in some range of levels. As set forth herein, mean IL-10 agent serum trough concentrations have been found to be of particular import for efficacy in certain indications.

In one embodiment, the present disclosure contemplates administration of IL-10 agent to achieve certain serum trough concentrations and/or maintain certain mean serum trough concentrations. In some embodiments of the present disclosure, the mean IL-10 agent serum trough concentration is in the range of from 1.0 pg/mL to 100 pg/mL; from 0.1 ng/mL to 1.0 ng/mL; from 1.0 ng/mL to 10 ng/mL; from 0.5 ng/mL to 5.0 ng/mL; from 0.75 ng/mL to 1.25 ng/mL or from 0.9 ng/mL to 1.1 ng/mL. In particular embodiments of the present disclosure, the mean IL-10 agent serum trough concentration is at least 1.25 ng/mL, at least 1.5 ng/mL, at least 1.6 ng/mL, at least 1.7 ng/mL, at least 1.8 ng/mL, at least 1.85 ng/mL, at least 1.9 ng/mL, at least 1.95 ng/mL, at least 1.97 ng/mL, and least 1.98 ng/mL, at least 1.99 ng/mL, at least 2.0 ng/mL or greater than 2 ng/mL. In further embodiments, the aforementioned period of time is at least 12 hours, at least 24 hours, at least 48 hours, at least 72 hours, at least 1 week, at least 2 weeks, at least 3 weeks, at least 1 month, at least 6 weeks, at least 2 months, at least 3 months, at least 6 months, at least 9 months, or greater than 12 months. In particular embodiments of the present disclosure, the mean IL-10 agent serum trough concentration is maintained for at least 85% of the period of time, at least 90%, at least 96%, at least 98%, at least 99% or 100% of the period of time.

In some embodiments of the present disclosure, blood plasma and/or serum level concentration profiles that can be produced include: a mean IL-10 agent plasma and/or serum trough concentration of greater than about 1.0 pg/mL, greater than about 10.0 pg/mL, greater than about 20.0 pg/mL, greater than about 30 pg/mL, greater than about 40 pg/mL, greater than about 50.0 pg/mL, greater than about 60.0 pg/mL, greater than about 70.0 pg/mL, greater than about 80.0 pg/mL, greater than about 90 pg/mL, greater than about 0.1 ng/mL, greater than about 0.2 ng/mL, greater than about 0.3 ng/mL, greater than about 0.4 ng/mL, greater than about 0.5 ng/mL, greater than about 0.6 ng/mL, greater than about 0.7 ng/mL, greater than about 0.8 ng/mL, greater than about 0.9 ng/mL, greater than about 1.0 ng/mL, greater than about 1.5 ng/mL, greater than about 2.0 ng/mL, greater than about 2.5 ng/mL, greater than about 3.0 ng/mL, greater than about 3.5 ng/mL, greater than about 4.0 ng/mL, greater than about 4.5 ng/mL, greater than about 5.0 ng/mL, greater than about 5.5 ng/mL, greater than about 6.0 ng/mL, greater than about 6.5 ng/mL, greater than about 7.0 ng/mL, greater than about 7.5 ng/mL, greater than about 8.0 ng/mL, greater than about 8.5 ng/mL, greater than about 9.0 ng/mL, greater than about 9.5 ng/mL, or greater than about 10.0 ng/mL.

In particular embodiments of the present disclosure, a mean IL-10 agent serum trough concentration is in the range of from 1.0 pg/mL to 10 ng/mL. In some embodiments, the mean IL-10 agent serum trough concentration is in the range of from 1.0 pg/mL to 100 pg/mL. In other embodiments, the mean IL-10 agent serum trough concentration is in the range of from 0.1 ng/mL to 1.0 ng/mL. In still other embodiments, the mean IL-10 agent serum trough concentration is in the range of from 1.0 ng/mL to 10 ng/mL. It is to be understood that the present disclosure contemplates ranges incorporating any concentrations encompassed by those set forth herein even if such ranges are not explicitly recited. By way of example, the mean IL-10 agent serum concentration in an embodiment can be in the range of from 0.5 ng/mL to 5 ng/mL. By way of further examples, particular embodiments of the present disclosure comprise a mean IL-10 agent serum trough concentration in a range of from about 0.5 ng/mL to about 10.5 ng/mL, from about 1.0 ng/mL to about 10.0 ng/mL, from about 1.0 ng/mL to about 9.0 ng/mL, from about 1.0 ng/mL to about 8.0 ng/mL, from about 1.0 ng/mL to about 7.0 ng/mL, from about 1.5 ng/mL to about 10.0 ng/mL, from about 1.5 ng/mL to about 9.0 ng/mL, from about 1.5 ng/mL to about 8.0 ng/mL, from about 1.5 ng/mL to about 7.0 ng/mL, from about 2.0 ng/mL to about 10.0 ng/mL, from about 2.0 ng/mL to about 9.0 ng/mL, from about 2.0 ng/mL to about 8.0 ng/mL, and from about 2.0 ng/mL to about 7.0 ng/mL.

The present disclosure contemplates administration of any dose and dosing regimen that results in maintenance of any of the IL-10 agent serum trough concentrations set forth above. By way of example, but not limitation, when the subject is a human, non-pegylated hIL-10 can be administered at a dose greater than 0.5 μg/kg/day, greater than 1.0 μg/kg/day, greater than 2.5 μg/kg/day, greater than 5 μg/kg/day, greater than 7.5 μg/kg, greater than 10.0 μg/kg, greater than 12.5 μg/kg, greater than 15 μg/kg/day, greater than 17.5 μg/kg/day, greater than 20 μg/kg/day, greater than 22.5 μg/kg/day, greater than 25 μg/kg/day, greater than 30 μg/kg/day, or greater than 35 μg/kg/day. In addition, by way of example, but not limitation, when the subject is a human, pegylated hIL-10 agent comprising a relatively small PEG (e.g., 5 kDa mono-di-PEG-hIL-10) can be administered at a dose of about 0.5 μg/kg/day/SC, alternatively of about 0.75 μg/kg/day/SC, alternatively of about 1 μg/kg/day/SC, alternatively of about 1.5 μg/kg/day/SC, alternatively of about 1.75 μg/kg/day, alternatively of about 2.0 μg/kg/day/SC, alternatively of about 3 μg/kg/day/SC, alternatively of about 4 μg/kg/day/SC, alternatively of about 5 μg/kg/day/SC, alternatively of about 8 μg/kg/day/SC, alternatively of about 10 μg/kg/day/SC, alternatively of about 12 μg/kg/day/SC, alternatively of about 15 μg/kg/day/SC, alternatively of about 20 μg/kg/day/SC.

It is envisaged that a dosing regimen sufficient to maintain a desired steady state serum trough concentration (e.g., 1 ng/mL) can result in an initial serum trough concentration that is higher than the desired steady state serum trough concentration. Because of the pharmacodynamic and pharmacokinetic characteristics of IL-10 in a mammalian subject, an initial trough concentration (achieved, for example, through the administration of one or more loading doses followed by a series of maintenance doses) gradually but continually decreases over a period of time even when the dosing parameters (amount and frequency) are kept constant. After that period to time, the gradual but continual decrease ends and a steady state serum trough concentration is maintained. By way of example, parenteral administration (e.g., SC and IV) of ~0.1 mg/kg/day of an IL-10 agent (e.g., mIL-10) to a mouse (e.g., a C57BL/6 mouse) is required to maintain a steady state serum trough concentration of 2.0 ng/mL. However, that steady state serum trough concentration may not be achieved until approximately 30 days after initiation of dosing at 0.1 mg/kg/day (and also after any loading dose(s)). Rather, after an initial serum trough concentration has been achieved (e.g., 2.5 ng/mL), that concentration gradually but continually decreases over the course of treatment after which time the desired steady state serum trough concentration (2.0 ng/mL) is maintained. One of skill in the art will be able to determine the dose needed to maintain the desired steady state trough concentration using, for example, ADME and patient-specific parameters.

In general, dosing parameters dictate that the dosage amount be less than an amount that could be irreversibly toxic to the subject (i.e., the maximum tolerated dose, "MTD") and not less than an amount required to produce a measurable effect on the subject. Such amounts are determined by, for example, the pharmacokinetic and pharmacodynamic parameters associated with ADME, taking into consideration the route of administration and other factors.

An effective dose (ED) is the dose or amount of an agent that produces a therapeutic response or desired effect in some fraction of the subjects taking it. The "median effective dose" or ED50 of an agent is the dose or amount of an agent that produces a therapeutic response or desired effect in 50% of the population to which it is administered. Although the ED50 is commonly used as a measure of reasonable expectance of an agent's effect, it is not necessarily the dose that a clinician might deem appropriate taking into consideration all relevant factors. Thus, in some situations the effective amount can be more than the calculated ED50, in other situations the effective amount can be less than the calculated ED50, and in still other situations the effective amount can be the same as the calculated ED50. In addition, an effective dose of the IL-10 agent (e.g. PEG-IL-10) of the present disclosure can be an amount that, when administered in one or more doses to a subject, produces a desired result relative to a healthy subject. For example, for a subject experiencing a particular disorder, an effective dose can be one that improves a diagnostic parameter, measure, marker and the like of that disorder by at least about 5%, at least about 10%, at least about 20%, at least about 25%, at least about 30%, at least about 40%, at least about 50%, at least about 60%, at least about 70%, at least about 80%, at least about 90%, or more than 90%, where 100% is defined as the diagnostic parameter, measure, marker and the like exhibited by a normal subject. The effective dose of the IL10 agent can be determined by IL-10 activity assays known in the art and described elsewhere herein. By way of example, in the tumor context, suitable IL-10 activity includes, for example, CD8+ T-cell infiltrate into tumor sites, expression of inflammatory cytokines, such as IFN-γ, IL-4, IL-6, IL-10, and RANK-L, from these infiltrating cells, and increased levels of TNF-α or IFN-γ in biological samples.

In some embodiments, for example when the IL10 agent is a PEG-IL-10 agent that is administered by continuous intravenous infusion to deliver about 50 to 800 μg protein/kg of body weight/day (e.g., about 1 to 16 μg protein/kg of body weight/day of a PEG-IL-10 agent). The infusion rate can be varied based on evaluation of, for example, adverse effects and blood cell counts. Other specific dosing parameters for the IL-10 agents are described elsewhere herein.

In certain embodiments, the dosage of the IL-10 agent and immune checkpoint pathway modulator is provided in a "unit dosage form". The phrase "unit dosage form" refers to physically discrete units, each unit containing a predetermined amount of a IL-10 agent and immune checkpoint pathway modulator of the present disclosure, either alone or in combination with one or more additional agents, sufficient to produce the desired effect. It will be appreciated that the parameters of a unit dosage form will depend on the particular agent and the effect to be achieved.

In some embodiments, the present disclosure contemplates methods wherein the IL-10 agent and immune checkpoint pathway modulator are administered to a subject at least once daily, at least once every 48 hours, at least once every 72 hours, at least once weekly, at least once every 2 weeks, at least once monthly, at least once every 2 months, or at least once every 3 months or longer. In certain embodiments, the IL-10 agent is administered in combination pembrolizumab (Keytruda®, Merck and Co, Rahway NJ) administered in at a dose of 160 mg (2 mg/kg) administered intravenously every three weeks. In certain embodiments, the IL-10 agent is administered in combination nivolumab (Opdivo®, BristolMyers Squibb, Princeton NJ) administered in accordance with the revised label approved dose of 240 mg (3 mg/kg) administered intravenously every two weeks. The recommended dose of ipilimumab is 3 mg/kg administered intravenously every 3 weeks for a total of 4 doses. In certain embodiments, the IL-10 agent is administered in combination with the immune checkpoint pathway inhibitors ipilimumab (YERVOY, Bristol-Myers Squibb), a recombinant, human monoclonal antibody that binds to the cytotoxic T-lymphocyte-associated antigen 4 (CTLA4). In an exemplary embodiment, combination therapy comprising PEG-1L-10 and ipilimumab can be initiated at or about the same time. In another exemplary embodiment comprising combination therapy with PEG-IL-10 and ipilmumab, ipilimumab therapy (administration every 3 weeks) can be initiated first, and weekly PEG-IL-10 therapy can be initiated one week thereafter, two weeks after which the second dose of ipilimumab is administered. In some embodiments, the therapeutic regimen comprises a wash-out period ("drug holiday") wherein the serum level of PEG-IL-10, ipilimumab, or both decreases to a desired level to allow the subject to recover from any adverse effects associated with the ipilimumab (e.g., immune-related adverse reactions). The skilled artisan (e.g., an oncologist) will be able to tailor a treatment regimen that takes into consideration the characteristics of the IL-10 and immune checkpoint pathway inhibitors agents (e.g., their pharmacokinetic parameters), patient-specific characteristics (e.g., renal function), and goals of therapy.

Although the preceding discussion regarding IL-10 agent serum concentrations, doses and treatment protocols that are necessary to achieve particular IL-10 serum concentrations, etc., pertains to monotherapy with an IL-10 agent (e.g., PEG-IL-10), in certain embodiments such doses, treatment protocols, etc. are also relevant to therapeutic regimens comprising an IL-10 agent in combination with one or more immune checkpoint pathway inhibitors. For example, a PEG-IL-10 dosing regimen may be the same when it is administered alone or when it is administered in combination with a PD1 antagonist because the PEG-IL-10 and PD1 antagonist have distinct mechanisms of action that allow the agents to be combined without modifications to their dosing parameters. However, such combinations can allow for modifications to the normal dosing regimen of the PEG-IL-10 and/or the immune checkpoint pathway inhibitors(s). For example, the therapeutic dose of one or both of the agents can be reduced, the frequency of dosing of one or both agents can be decreased, and/or the duration of therapy of one or both of the agents can be shortened, while retaining the desired therapeutic effect.

The skilled artisan (e.g., a pharmacologist) is able to determine the optimum dosing regimen(s) when an IL-10 agent (e.g., PEG-IL-10) is administered in combination with an immune checkpoint pathway inhibitors(s). By way of example, in some embodiments the optimum PEG-IL-10 dosing regimen may require a reduction in the amount of PEG-IL-10 administered per dose (e.g., less than 1.0 μg/kg/day, less than 0.75 μg/kg/day, less than 0.5 μg/kg/day, less than 0.25 μg/kg/day, or less than 0.125 μg/kg/day). In certain exemplary embodiments of the present disclosure, a mean IL-10 agent serum trough concentration may be in a range of from about 0.1 ng/mL to about 9.5 ng/mL, from about 0.25 ng/mL to about 8.0 ng/mL, from about 0.5 ng/mL to about 7.0 ng/mL, from about 0.75 ng/mL to about 6.0 ng/mL, or from about 1.0 ng/mL to about 5.0 ng/mL.

When an IL-10 agent is administered in combination with an immune checkpoint pathway inhibitors, one or more of the dosing parameters of the IL-10 agent applicable to monotherapy can be modified while the dosing parameters of the immune checkpoint pathway inhibitors(s) applicable to monotherapy can remain the same; one or more of the dosing parameters of the IL-10 agent applicable to monotherapy can remain the same while one or more the dosing parameters of the immune checkpoint pathway inhibitors(s) applicable to monotherapy can be modified; one or more of the dosing parameters of the IL-10 agent and the immune checkpoint pathway inhibitors(s) applicable to monotherapy can be modified; or the dosing parameters of each of the IL-10 agent and the immune checkpoint pathway inhibitors (s) applicable to monotherapy can remain the same.

The IL-10 agents and immune checkpoint pathway inhibitors of the present disclosure can be in the form of compositions suitable for administration to a subject. In general, such compositions are "pharmaceutical compositions" comprising IL-10 and/or an immune checkpoint pathway inhibitors(s), and one or more pharmaceutically acceptable or physiologically acceptable diluents, carriers or excipients. In certain embodiments, the IL-10 agents and immune checkpoint pathway inhibitors are each present in a therapeutically acceptable amount. The pharmaceutical compositions can be used in the methods of the present disclosure; thus, for example, the pharmaceutical compositions can be administered ex vivo or in vivo to a subject in order to practice the therapeutic and prophylactic methods and uses described herein.

Particular embodiments of the present disclosure are directed to pharmaceutical compositions comprising a therapeutically acceptable amount of an IL-10 agent in combination with a therapeutically acceptable amount of an immune checkpoint pathway inhibitors(s), along with one or more pharmaceutically acceptable diluents, carriers and/or excipients (e.g., an isotonic injection solution). The pharmaceutical composition is generally one that is suitable for human administration. Furthermore, in some embodiments the pharmaceutical composition comprises at least one additional supplementary agent.

One embodiment of the invention provides a pharmaceutical formulation comprising an IL-10 agent and at least one immune checkpoint pathway modulator or in pharmaceutical formulation of multiple immune checkpoint pathway modulator optionally containing a supplementary therapeutic agent The pharmaceutical compositions typically comprise a therapeutically effective amount of an IL-10 agent and/or a therapeutically effective amount of an immune checkpoint pathway modulator, optionally a supplementary agent, in the presence of a pharmaceutically and physiologically acceptable formulation agents. Suitable pharmaceutically acceptable or physiologically acceptable diluents, carriers or excipients include, but are not limited to, antioxidants (e.g., ascorbic acid and sodium bisulfate), preservatives (e.g., benzyl alcohol, methyl parabens, ethyl or n-propyl, p-hydroxybenzoate), emulsifying agents, suspending agents, dispersing agents, solvents, fillers, bulking agents, detergents, buffers, vehicles, diluents, and/or adjuvants. For example, a suitable vehicle can be physiological saline solution or citrate buffered saline, possibly supplemented with other materials common in pharmaceutical compositions for parenteral administration. Neutral buffered saline or saline mixed with serum albumin are further exemplary vehicles. Those skilled in the art will readily recognize a variety of buffers that can be used in the pharmaceutical compositions and dosage forms contemplated herein. Typical buffers include, but are not limited to, pharmaceutically acceptable weak acids, weak bases, or mixtures thereof. As an example, the buffer components can be water soluble materials such as phosphoric acid, tartaric acids, lactic acid, succinic acid, citric acid, acetic acid, ascorbic acid, aspartic acid, glutamic acid, and salts thereof. Acceptable buffering agents include, for example, a Tris buffer, N-(2-Hydroxyethyl)piperazine-N'-(2-ethanesulfonic acid) (HEPES), 2-(N-Morpholino)ethanesulfonic acid (MES), 2-(N-Morpholino)ethanesulfonic acid sodium salt (MES), 3-(N-Morpholino)propanesulfonic acid (MOPS), and N-tris[Hydroxymethyl]methyl-3-aminopropanesulfonic acid (TAPS).

The pharmaceutical compositions can be in the form of a sterile injectable aqueous or oleagenous suspension. This suspension can be formulated according to the known art using those suitable dispersing or wetting agents and suspending agents mentioned herein. The sterile injectable preparation can also be a sterile injectable solution or suspension in a non-toxic parenterally-acceptable diluent or solvent, for example, as a solution in 1,3-butane diol. Acceptable diluents, solvents and dispersion media that can be employed include water, Ringer's solution, isotonic sodium chloride solution, Cremophor EL™ (BASF, Parsippany, NJ) or phosphate buffered saline (PBS), ethanol, polyol (e.g., glycerol, propylene glycol, and liquid polyethylene glycol), and suitable mixtures thereof. In addition, sterile, fixed oils are conventionally employed as a solvent or suspending medium. For this purpose any bland fixed oil can be employed, including synthetic mono- or diglycerides. Moreover, fatty acids such as oleic acid, find use in the preparation of injectables. Prolonged absorption of particular injectable formulations can be achieved by including an agent that delays absorption (e.g., aluminum monostearate or gelatin).

The pharmaceutical compositions containing the active agents(s) can be in a form suitable for oral use, for example, as tablets, capsules, troches, lozenges, aqueous or oily suspensions, dispersible powders or granules, emulsions, hard or soft capsules, or syrups, solutions, microbeads or elixirs. In particular embodiments, an active agent or an agent co-administered with an IL-10 agent described herein is in a form suitable for oral use. Pharmaceutical compositions intended for oral use can be prepared according to any method known to the art for the manufacture of pharmaceutical compositions, and such compositions can contain one or more agents such as, for example, sweetening agents, flavoring agents, coloring agents and preserving agents in order to provide pharmaceutically elegant and palatable preparations. Tablets, capsules and the like contain the active ingredient in admixture with non-toxic pharmaceutically acceptable excipients which are suitable for the manufacture of tablets. These excipients can be, for example, diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc.

The formulations of the agents may also be designed to provide to extended release of the active agents. Extended release formulations are known in the art and include biodegradable or biocompatible particles or a polymeric substance such as polyesters, polyamine acids, hydrogel, polyvinyl pyrrolidone, polyanhydrides, polyglycolic acid, ethylene-vinylacetate, methylcellulose, carboxymethylcellulose, protamine sulfate, or lactide/glycolide copolymers, polylactide/glycolide copolymers, or ethylenevinylacetate copolymers in order to control delivery of an administered composition. For example, the oral agent can be entrapped in microcapsules prepared by coacervation techniques or by interfacial polymerization, by the use of hydroxymethylcellulose or gelatin-microcapsules or poly (methylmethacrolate) microcapsules, respectively, or in a colloid drug delivery system. Colloidal dispersion systems include macromolecule complexes, nano-capsules, microspheres, microbeads, and lipid-based systems, including oil-in-water emulsions, micelles, mixed micelles, and liposomes. Methods for the preparation of the above-mentioned formulations will be apparent to those skilled in the art. The formulations of the agents may also be depot injections, which are generally administered subcutaneously or intramuscularly, can also be utilized to release the active agents disclosed herein over a defined period of time.

Aqueous suspensions contain the active materials in admixture with excipients suitable for the manufacture thereof. Such excipients can be suspending agents, for example sodium carboxymethylcellulose, methylcellulose, hydroxy-propylmethylcellulose, sodium alginate, polyvinylpyrrolidone, gum tragacanth and gum acacia; dispersing or wetting agents, for example a naturally-occurring phosphatide (e.g., lecithin), or condensation products of an alkylene oxide with fatty acids (e.g., polyoxy-ethylene stearate), or condensation products of ethylene oxide with long chain aliphatic alcohols (e.g., for heptadecaethyleneoxycetanol), or condensation products of ethylene oxide with partial esters derived from fatty acids and a hexitol (e.g., polyoxyethylene sorbitol monooleate), or condensation products of ethylene oxide with partial esters derived from fatty acids and hexitol anhydrides (e.g., polyethylene sorbitan monooleate). The aqueous suspensions can also contain one or more preservatives.

The pharmaceutical compositions of the present disclosure may also be oily suspensions can be formulated by suspending the active ingredient in a vegetable oil, for example arachis oil, olive oil, sesame oil or coconut oil, or in a mineral oil such as liquid paraffin. The oily suspensions can contain a thickening agent, for example beeswax, hard paraffin or cetyl alcohol. Sweetening agents such as those set forth above, and flavoring agents can be added to provide a palatable oral preparation.

The pharmaceutical compositions of the present disclosure may also be dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified herein.

The pharmaceutical compositions of the present disclosure can also be in the form of oil-in-water emulsions. The oily phase can be a vegetable oil, for example olive oil or arachis oil, or a mineral oil, for example, liquid paraffin, or mixtures of these. Suitable emulsifying agents can be naturally occurring gums, for example, gum acacia or gum tragacanth; naturally occurring phosphatides, for example, soy bean, lecithin, and esters or partial esters derived from fatty acids; hexitol anhydrides, for example, sorbitan monooleate; and condensation products of partial esters with ethylene oxide, for example, polyoxyethylene sorbitan monooleate.

The pharmaceutical compositions of the present disclosure may also include carriers to protect the composition against rapid degradation or elimination from the body, such as a controlled release formulation, including implants, liposomes, hydrogels, prodrugs and microencapsulated delivery systems. For example, a time delay material such as glyceryl monostearate or glyceryl stearate alone, or in combination with a wax, can be employed.

The pharmaceutical compositions of the present disclosure may also be in the form of suppositories for rectal administration. The suppositories can be prepared by mixing the drug with a suitable non-irritating excipient which is solid at ordinary temperatures but liquid at the rectal temperature and will therefore melt in the rectum to release the drug. Such materials include, but are not limited to, cocoa butter and polyethylene glycols.

The pharmaceutical compositions of the present disclosure may also be in the form of any other suitable pharmaceutical composition (e.g., sprays for nasal or inhalation use) currently known or developed in the future.

Presentations:

After a pharmaceutical composition has been formulated, it can be stored in sterile vials as a solution, suspension, gel, emulsion, solid, or dehydrated or lyophilized powder. Such formulations can be stored either in a ready-to-use form, a lyophilized form requiring reconstitution prior to use, a liquid form requiring dilution prior to use, or other acceptable form. In some embodiments, the pharmaceutical composition is provided in a single-use container (e.g., a single-use vial, ampoule, syringe, or autoinjector (similar to, e.g., an EpiPen®)), whereas a multi-use container (e.g., a multi-use vial) is provided in other embodiments. Any drug delivery apparatus can be used to deliver IL-10, including implants (e.g., implantable pumps) and catheter systems, slow injection pumps and devices, all of which are well known to the skilled artisan. Depot injections, which are generally administered subcutaneously or intramuscularly, can also be utilized to release the polypeptides disclosed herein over a defined period of time. Depot injections are usually either solid- or oil-based and generally comprise at least one of the formulation components set forth herein. One of ordinary skill in the art is familiar with possible formulations and uses of depot injections.

Certain embodiments of the present disclosure contemplate a sterile container that contains one of the above-mentioned pharmaceutical compositions and optionally one or more additional components. By way of example, but not limitation, the sterile container can be a syringe, in particular a prefilled syringe ready for administration. In still further embodiments, the sterile container is one component of a kit; the kit can also contain, for example, a second sterile container that comprises at least one prophylactic or therapeutic agent, examples of which are set forth herein.

The present disclosure also contemplates kits comprising pharmaceutical formulations of IL-10 agents and immune checkpoint pathway modulator(s). The kits are generally in the form of a physical structure housing various components, as described below, and can be utilized, for example, in practicing the methods described above. A kit can include one or more pharmaceutical formulations of IL-10 agents (e.g., PEG-IL-10) disclosed herein provided in a sterile container and one or more pharmaceutical formulations of immune checkpoint pathway modulator(s), pharmaceutical formulations provided a sterile container(s). The pharmaceutical formulations IL-10 agents and pharmaceutical formulations immune checkpoint pathway modulator(s) can be provided in a form that is ready for use or in a form requiring, for example, reconstitution or dilution prior to administration. When the IL-10 agents and/or immune checkpoint pathway modulator(s) are provide a form that needs to be reconstituted by a user, the kit can also include buffers, pharmaceutically acceptable excipients, and the like, packaged with or separately from the IL-10 agents or immune checkpoint pathway modulator(s). Similarly, when supplementary therapy (e.g., an IL-10 agent, an immune checkpoint pathway inhibitors(s), and a supplementary agent) is contemplated, the kit can contain the several agents separately or two or more of them can already be combined in the kit. A kit of the present disclosure can be designed for conditions necessary to properly maintain the components housed therein (e.g., refrigeration or freezing).

A kit can contain a label or packaging insert including identifying information for the components therein and instructions for their use (e.g., dosing parameters, clinical pharmacology of the active ingredient(s), including mechanism(s) of action, pharmacokinetics and pharmacodynamics, adverse effects, contraindications, etc.). Each component of the kit can be enclosed within an individual container, and all of the various containers can be within a single package. Labels or inserts can include manufacturer information such as lot numbers and expiration dates. The label or packaging insert can be, e.g., integrated into the physical structure housing the components, contained separately within the physical structure, or affixed to a component of the kit (e.g., an ampule, syringe or vial).

Labels or inserts can additionally include, or be incorporated into, a computer readable medium, such as a disk (e.g., hard disk, card, memory disk), optical disk such as CD- or DVD-ROM/RAM, DVD, MP3, magnetic tape, or an electrical storage media such as RAM and ROM or hybrids of these such as magnetic/optical storage media, FLASH media or memory-type cards. In some embodiments, the actual instructions are not present in the kit, but means for obtaining the instructions from a remote source, e.g., via an internet site, are provided.

Particular embodiments of this invention are described herein, including the best mode known to the inventors for carrying out the invention. Upon reading the foregoing, description, variations of the disclosed embodiments may become apparent to individuals working in the art, and it is expected that those skilled artisans may employ such variations as appropriate. Accordingly, it is intended that the invention be practiced otherwise than as specifically described herein, and that the invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All publications, patent applications, accession numbers, and other references cited in this specification are herein incorporated by reference as if each individual publication or patent application were specifically and individually indicated to be incorporated by reference.

SEQUENCE LISTING

```
Sequence total quantity: 41
SEQ ID NO: 1            moltype = AA  length = 11
FEATURE                 Location/Qualifiers
REGION                  1..11
                        note = Synthetic construct
source                  1..11
                        mol_type = protein
                        organism = synthetic construct
SEQUENCE: 1
GGNSIGSYSV H                                                      11

SEQ ID NO: 2            moltype = AA  length = 7
FEATURE                 Location/Qualifiers
REGION                  1..7
                        note = Synthetic construct
source                  1..7
                        mol_type = protein
                        organism = synthetic construct
SEQUENCE: 2
DDSDRPS                                                           7

SEQ ID NO: 3            moltype = AA  length = 10
FEATURE                 Location/Qualifiers
REGION                  1..10
                        note = Synthetic construct
source                  1..10
                        mol_type = protein
                        organism = synthetic construct
SEQUENCE: 3
QVWDTSSYWV                                                        10

SEQ ID NO: 4            moltype = AA  length = 10
FEATURE                 Location/Qualifiers
REGION                  1..10
                        note = Synthetic construct
source                  1..10
                        mol_type = protein
                        organism = synthetic construct
SEQUENCE: 4
GFTFSSYAMS                                                        10

SEQ ID NO: 5            moltype = AA  length = 17
FEATURE                 Location/Qualifiers
REGION                  1..17
                        note = Synthetic construct
source                  1..17
                        mol_type = protein
                        organism = synthetic construct
SEQUENCE: 5
DISGGGGTTY YADSVKG                                                17

SEQ ID NO: 6            moltype = AA  length = 10
FEATURE                 Location/Qualifiers
REGION                  1..10
                        note = Synthetic construct
source                  1..10
                        mol_type = protein
                        organism = synthetic construct
```

-continued

```
SEQUENCE: 6
SGTVVTDFDY                                                          10

SEQ ID NO: 7            moltype = AA  length = 107
FEATURE                 Location/Qualifiers
REGION                  1..107
                        note = Synthetic construct
source                  1..107
                        mol_type = protein
                        organism = synthetic construct
SEQUENCE: 7
SYVLTQPPSV SVAPGQTARV TCGGNSIGSY SVHWYQQKPG QAPVLVVYDD SDRPSGIPER  60
FSGSNSGNTA ALTISRVEAG DEADYYCQVW DTSSYWVFGG GTKLTVL                107

SEQ ID NO: 8            moltype = AA  length = 119
FEATURE                 Location/Qualifiers
REGION                  1..119
                        note = Synthetic construct
source                  1..119
                        mol_type = protein
                        organism = synthetic construct
SEQUENCE: 8
EVQLLESGGG LVQPGGSLRL SCPASGFTFS SYAMSWVRQA PGKGLGWVSD ISGGGGTTYY  60
ADSVKGRFTI SRDNSKNTLY LQMNSLRGED TAVYYCAKSG TVVTDFDYWG QGTLVTVSS   119

SEQ ID NO: 9            moltype = AA  length = 5
FEATURE                 Location/Qualifiers
REGION                  1..5
                        note = Synthetic construct
VARIANT                 1..5
                        note = REPEAT - This stretch of residues may be repeated up
                         to 50 times.
source                  1..5
                        mol_type = protein
                        organism = synthetic construct
SEQUENCE: 9
GSGGS                                                               5

SEQ ID NO: 10           moltype = AA  length = 4
FEATURE                 Location/Qualifiers
REGION                  1..4
                        note = Synthetic construct
VARIANT                 1..4
                        note = REPEAT - This stretch of residues may be repeated up
                         to 50 times.
source                  1..4
                        mol_type = protein
                        organism = synthetic construct
SEQUENCE: 10
GGGS                                                                4

SEQ ID NO: 11           moltype = AA  length = 446
FEATURE                 Location/Qualifiers
REGION                  1..446
                        note = Synthetic construct
source                  1..446
                        mol_type = protein
                        organism = synthetic construct
SEQUENCE: 11
EVQLLESGGG LVQPGGSLRL SCPASGFTFS SYAMSWVRQA PGKGLGWVSD ISGGGGTTYY  60
ADSVKGRFTI SRDNSKNTLY LQMNSLRGED TAVYYCAKSG TVVTDFDYWG QGTLVTVSSA  120
STKGPSVFPL APCSRSTSES TAALGCLVKD YFPEPVTVSW NSGALTSGVH TFPAVLQSSG  180
LYSLSSVVTV PSSSLGTKTY TCNVDHKPSN TKVDKRVESK YGPPCPPCPA PEFLGGPSVF  240
LFPPKPKDTL MISRTPEVTC VVVDVSQEDP EVQFNWYVDG VEVHNAKTKP REEQFNSTYR  300
VVSVLTVLHQ DWLNGKEYKC KVSNKGLPSS IEKTISKAKG QPREPQVYTL PPSQEEMTKN  360
QVSLTCLVKG FYPSDIAVEW ESNGQPENNY KTTPPVLDSD GSFFLYSRLT VDKSRWQEGN  420
VFSCSVMHEA LHNHYTQKSL SLSLGK                                       446

SEQ ID NO: 12           moltype = AA  length = 213
FEATURE                 Location/Qualifiers
REGION                  1..213
                        note = Synthetic construct
source                  1..213
                        mol_type = protein
                        organism = synthetic construct
SEQUENCE: 12
SYVLTQPPSV SVAPGQTARV TCGGNSIGSY SVHWYQQKPG QAPVLVVYDD SDRPSGIPER  60
FSGSNSGNTA ALTISRVEAG DEADYYCQVW DTSSYWVFGG GTKLTVLGQP KAAPSVTLFP  120
PSSEELQANK ATLVCLISDF YPGAVTVAWK ADSSPVKAGV ETTTPSKQSN NKYAASSYLS  180
```

-continued

```
LTPEQWKSHR SYSCQVTHEG STVEKTVAPT ECS                       213

SEQ ID NO: 13          moltype = DNA  length = 1338
FEATURE                Location/Qualifiers
misc_feature           1..1338
                       note = Synthetic construct
source                 1..1338
                       mol_type = other DNA
                       organism = synthetic construct
SEQUENCE: 13
gaggtccagc tcctggaatc cgggggcggt ctggtccagc cgggcggctc gctccgcctg  60
tcctgcccgg cgagcggctt caccttctcc tcctacgcca tgtcctgggt gaggcaggcc  120
cccggcaagg gcctcggctg ggtcagcgac atctccggcg gcggcggcac cacgtactac  180
gcggactcgg tgaagggccg gttcacgatc tcccgggaca actccaagaa caccctgtac  240
ctgcagatga actcactgcg gggcgaggac acggcggtgt attactgcgc caagtccgga  300
acggttgtga ctgatttcga ctactggggc cagggcaccc tggtgaccgt gtccagcgcc  360
tccaccaagg gccccagcgt gttccccctg gcgccgtgct cgcggagcac cagcgagtcc  420
accgccgcgc tcggttgcct cgtcaaggac tacttccccg agccggtcac agtgtcatgg  480
aactccggcg cgctgacgag cggcgtgcac accttcccgg ccgtgctcca gtccagcggc  540
ctgtacagcc tcagtagcgt cgtgacggtg ccctcgtcgt cgctgggcac gaagacctac  600
acctgcaacg tggaccacaa gccgtccaac accaaggtcg ataagcgagt ggagagcaag  660
tacggccccc cgtgcccccc ctgcccggcc ccggagttcc tgggtggccc ctccgtgttc  720
ctcttccccc cgaagcccaa agacaccctc atgatcagcc ggacgccgga ggtcacgtgc  780
gtcgtcgtgg acgtgagcca ggaagacccg gaggtccagt tcaactggta cgtggacggc  840
gtcgaggtgc ataacgccaa gaccaagcct cgcgaggaac agttcaactc cacttaccgc  900
gtcgtgtccg tcctcaccgt cctgcaccag gactggctca acgggaagga atacaagtgc  960
aaggtctcga acaagggcct gccgtcgtcc atcgagaaga ccatcagcaa ggccaagggc  1020
cagccgcggg agccccaggt ctacaccctc ccccccctccc aggaagagat gacgaagaac  1080
caggtgagcc tgacgtgcct cgtgaagggg ttctacccct ccgacatcgc agtcgagtgg  1140
gagagcaacg gccagccgga gaacaactac aagacgaccc ccccggtgct ggacagcgac  1200
gggtccttct tcctctactc gcgtctcaca gtcgacaagt cgcgctggca ggagggcaac  1260
gtcttctcgt gctccgtgat gcacgaggcc ctgcacaacc actacaccca gaagtcgctg  1320
tccctgtccc tgggcaag                                        1338

SEQ ID NO: 14          moltype = DNA  length = 639
FEATURE                Location/Qualifiers
misc_feature           1..639
                       note = Synthetic construct
source                 1..639
                       mol_type = other DNA
                       organism = synthetic construct
SEQUENCE: 14
agctacgtgc tgacccagcc gccctcggtg tcggtcgccc cgggccagac ggcacgtgtg  60
acctgcggcg gtaacagcat cggctcctac tcggtccact ggtatcagca gaagccgggg  120
caggccccgg tcctggtggt ctacgacgac agcgaccgcc cgtccggcat ccccgaacgc  180
ttcagcggct caaacagcgg gaacaccgcg gccctgacga tctcgcgcgt cgaggcgggg  240
gacgaagccg attactactg ccaggtctgg gacacctcga gttactgggt gttcggcggg  300
ggcacgaagc tgaccgtcct cggccagccg aaggccgccc cctcagtaac cctgttcccc  360
ccgtcctcgg aggagttgca ggcgaacaag gcgacgctgg tgtgcttgat ctcggacttc  420
taccccggag cggtgacggt cgcctggaag gccgactcct ccccggtcaa ggcgggcgtg  480
gagacgacca ccccctccaa gcagagcaac aacaagtacg ccgcctcgag ctacctctcg  540
ctgacacccg agcagtggaa gtcccaccgg tcctactcgt gccaggtaac ccacgagggc  600
tccaccgtcg agaagaccgt ggcccccacc gagtgcagc                  639

SEQ ID NO: 15          moltype = AA  length = 11
FEATURE                Location/Qualifiers
REGION                 1..11
                       note = Synthetic construct
source                 1..11
                       mol_type = protein
                       organism = synthetic construct
SEQUENCE: 15
YGRKKRRQRR R                                               11

SEQ ID NO: 16          moltype = AA  length = 12
FEATURE                Location/Qualifiers
REGION                 1..12
                       note = Synthetic construct
source                 1..12
                       mol_type = protein
                       organism = synthetic construct
SEQUENCE: 16
RRQRRTSKLM KR                                              12

SEQ ID NO: 17          moltype = AA  length = 27
FEATURE                Location/Qualifiers
REGION                 1..27
                       note = Synthetic construct
source                 1..27
```

-continued

```
                        mol_type = protein
                        organism = synthetic construct
SEQUENCE: 17
GWTLNSAGYL LGKINLKALA ALAKKIL                                          27

SEQ ID NO: 18           moltype = AA  length = 33
FEATURE                 Location/Qualifiers
REGION                  1..33
                        note = Synthetic construct
source                  1..33
                        mol_type = protein
                        organism = synthetic construct
SEQUENCE: 18
KALAWEAKLA KALAKALAKH LAKALAKALK CEA                                   33

SEQ ID NO: 19           moltype = AA  length = 16
FEATURE                 Location/Qualifiers
REGION                  1..16
                        note = Synthetic construct
source                  1..16
                        mol_type = protein
                        organism = synthetic construct
SEQUENCE: 19
RQIKIWFQNR RMKWKK                                                      16

SEQ ID NO: 20           moltype = AA  length = 9
FEATURE                 Location/Qualifiers
REGION                  1..9
                        note = Synthetic construct
source                  1..9
                        mol_type = protein
                        organism = synthetic construct
SEQUENCE: 20
RKKRRQRRR                                                              9

SEQ ID NO: 21           moltype = AA  length = 8
FEATURE                 Location/Qualifiers
REGION                  1..8
                        note = Synthetic construct
source                  1..8
                        mol_type = protein
                        organism = synthetic construct
SEQUENCE: 21
RKKRRQRR                                                               8

SEQ ID NO: 22           moltype = AA  length = 11
FEATURE                 Location/Qualifiers
REGION                  1..11
                        note = Synthetic construct
source                  1..11
                        mol_type = protein
                        organism = synthetic construct
SEQUENCE: 22
YARAAARQAR A                                                           11

SEQ ID NO: 23           moltype = AA  length = 11
FEATURE                 Location/Qualifiers
REGION                  1..11
                        note = Synthetic construct
source                  1..11
                        mol_type = protein
                        organism = synthetic construct
SEQUENCE: 23
THRLPRRRRR R                                                           11

SEQ ID NO: 24           moltype = AA  length = 11
FEATURE                 Location/Qualifiers
REGION                  1..11
                        note = Synthetic construct
source                  1..11
                        mol_type = protein
                        organism = synthetic construct
SEQUENCE: 24
GGRRARRRRR R                                                           11

SEQ ID NO: 25           moltype = AA  length = 160
FEATURE                 Location/Qualifiers
source                  1..160
                        mol_type = protein
```

```
                         organism = Homo sapiens
SEQUENCE: 25
SPGQGTQSEN SCTHFPGNLP NMLRDLRDAF SRVKTFFQMK DQLDNLLLKE SLLEDFKGYL  60
GCQALSEMIQ FYLEEVMPQA ENQDPDIKAH VNSLGENLKT LRLRLRRCHR FLPCENKSKA  120
VEQVKNAFNK LQEKGIYKAM SEFDIFINYI EAYMTMKIRN                       160

SEQ ID NO: 26            moltype = AA  length = 161
FEATURE                  Location/Qualifiers
REGION                   1..161
                         note = Synthetic construct
source                   1..161
                         mol_type = protein
                         organism = synthetic construct
SEQUENCE: 26
MSPGQGTQSE NSCTHFPGNL PNMLRDLRDA FSRVKTFFQM KDQLDNLLLK ESLLEDFKGY  60
LGCQALSEMI QFYLEEVMPQ AENQDPDIKA HVNSLGENLK TLRLRLRRCH RFLPCENKSK  120
AVEQVKNAFN KLQEKGIYKA MSEFDIFINY IEAYMTMKIR N                     161

SEQ ID NO: 27            moltype = AA  length = 161
FEATURE                  Location/Qualifiers
REGION                   1..161
                         note = Synthetic construct
SITE                     1
                         note = MISC_FEATURE - N-formyl group on methionine
source                   1..161
                         mol_type = protein
                         organism = synthetic construct
SEQUENCE: 27
MSPGQGTQSE NSCTHFPGNL PNMLRDLRDA FSRVKTFFQM KDQLDNLLLK ESLLEDFKGY  60
LGCQALSEMI QFYLEEVMPQ AENQDPDIKA HVNSLGENLK TLRLRLRRCH RFLPCENKSK  120
AVEQVKNAFN KLQEKGIYKA MSEFDIFINY IEAYMTMKIR N                     161

SEQ ID NO: 28            moltype = AA  length = 5
FEATURE                  Location/Qualifiers
REGION                   1..5
                         note = Synthetic construct
VARIANT                  1..5
                         note = REPEAT - This stretch of residues may be repeated up
                          to 20 times.
source                   1..5
                         mol_type = protein
                         organism = synthetic construct
SEQUENCE: 28
GSGGS                                                             5

SEQ ID NO: 29            moltype = AA  length = 5
FEATURE                  Location/Qualifiers
REGION                   1..5
                         note = Synthetic construct
VARIANT                  1
                         note = REPEAT - This residue may be repeated up to 20 times.
VARIANT                  1..5
                         note = REPEAT - This stretch of residues may be repeated up
                          to 20 times.
VARIANT                  2
                         note = REPEAT - This residue may be repeated up to 20 times.
VARIANT                  3
                         note = REPEAT - This residue may be repeated up to 20 times.
VARIANT                  4
                         note = REPEAT - This residue may be repeated up to 20 times.
VARIANT                  5
                         note = REPEAT - This residue may be repeated up to 20 times.
source                   1..5
                         mol_type = protein
                         organism = synthetic construct
SEQUENCE: 29
GSGSG                                                             5

SEQ ID NO: 30            moltype = AA  length = 5
FEATURE                  Location/Qualifiers
REGION                   1..5
                         note = Synthetic construct
VARIANT                  1..5
                         note = REPEAT - This stretch of residues may be repeated up
                          to 20 times.
VARIANT                  5
                         note = REPEAT - This residue may be repeated up to 20 times.
source                   1..5
                         mol_type = protein
```

```
                        organism = synthetic construct
SEQUENCE: 30
GSGGS                                                                        5

SEQ ID NO: 31           moltype = AA  length = 5
FEATURE                 Location/Qualifiers
REGION                  1..5
                        note = Synthetic construct
VARIANT                 1..5
                        note = REPEAT - This stretch of residues may be repeated up
                         to 20 times.
VARIANT                 4
                        note = REPEAT - This residue may be repeated up to 20 times.
source                  1..5
                        mol_type = protein
                        organism = synthetic construct
SEQUENCE: 31
GSGSG                                                                        5

SEQ ID NO: 32           moltype = AA  length = 4
FEATURE                 Location/Qualifiers
REGION                  1..4
                        note = Synthetic construct
VARIANT                 1..4
                        note = REPEAT - This stretch of residues may be repeated up
                         to 20 times.
VARIANT                 4
                        note = REPEAT - This residue may be repeated up to 20 times.
source                  1..4
                        mol_type = protein
                        organism = synthetic construct
SEQUENCE: 32
GGGS                                                                         4

SEQ ID NO: 33           moltype = AA  length = 4
FEATURE                 Location/Qualifiers
REGION                  1..4
                        note = Synthetic construct
source                  1..4
                        mol_type = protein
                        organism = synthetic construct
SEQUENCE: 33
GGSG                                                                         4

SEQ ID NO: 34           moltype = AA  length = 5
FEATURE                 Location/Qualifiers
REGION                  1..5
                        note = Synthetic construct
source                  1..5
                        mol_type = protein
                        organism = synthetic construct
SEQUENCE: 34
GGSGG                                                                        5

SEQ ID NO: 35           moltype = AA  length = 5
FEATURE                 Location/Qualifiers
REGION                  1..5
                        note = Synthetic construct
source                  1..5
                        mol_type = protein
                        organism = synthetic construct
SEQUENCE: 35
GSGSG                                                                        5

SEQ ID NO: 36           moltype = AA  length = 5
FEATURE                 Location/Qualifiers
REGION                  1..5
                        note = Synthetic construct
source                  1..5
                        mol_type = protein
                        organism = synthetic construct
SEQUENCE: 36
GSGGG                                                                        5

SEQ ID NO: 37           moltype = AA  length = 5
FEATURE                 Location/Qualifiers
REGION                  1..5
                        note = Synthetic construct
source                  1..5
```

-continued

```
                        mol_type = protein
                        organism = synthetic construct
SEQUENCE: 37
GGGSG                                                5

SEQ ID NO: 38           moltype = AA  length = 5
FEATURE                 Location/Qualifiers
REGION                  1..5
                        note = Synthetic construct
source                  1..5
                        mol_type = protein
                        organism = synthetic construct
SEQUENCE: 38
GSSSG                                                5

SEQ ID NO: 39           moltype = AA  length = 5
FEATURE                 Location/Qualifiers
REGION                  1..5
                        note = Synthetic construct
VARIANT                 1..5
                        note = REPEAT - This stretch of residues may be repeated up
                         to 50 times.
source                  1..5
                        mol_type = protein
                        organism = synthetic construct
SEQUENCE: 39
GGGGS                                                5

SEQ ID NO: 40           moltype = AA  length = 4
FEATURE                 Location/Qualifiers
REGION                  1..4
                        note = Synthetic construct
source                  1..4
                        mol_type = protein
                        organism = synthetic construct
SEQUENCE: 40
GGGS                                                 4

SEQ ID NO: 41           moltype = AA  length = 5
FEATURE                 Location/Qualifiers
REGION                  1..5
                        note = Synthetic construct
source                  1..5
                        mol_type = protein
                        organism = synthetic construct
SEQUENCE: 41
GGGGS                                                5
```

What is claimed is:

1. A method of treating a neoplastic disease in a mammalian subject, wherein the neoplastic disease is non-small cell lung cancer that has (i) an intermediate tumor mutation burden of greater than 15 but less than 100 mutations per megabase sequenced, or a low tumor mutation burden of less than or equal to 15 mutations per megabase sequenced, and (ii) a low PD-L1 expression or an intermediate PD-L1 expression, the method comprising administering to the subject:

a) a therapeutically effective amount of an immune checkpoint pathway modulator; and b) a therapeutically effective amount of an IL-10 agent, wherein the immune checkpoint pathway modulator is a PD1 pathway inhibitor selected from monoclonal antibodies that interfere with the binding of PD1 and PDL1; and wherein the IL-10 agent is a dimeric molecule having IL-10 activity and comprising two IL-10 polypeptides that bind to the IL-10 receptor and modulate the same signaling pathway as IL-10 and are capable of eliciting a biological response characteristic of IL-10.

2. The method of claim 1, wherein the neoplastic disease is a primary tumor.

3. The method of claim 1, wherein the mammalian subject is a human.

4. The method of claim 1, wherein the IL-10 agent comprises two IL-10polypeptides each having the amino acid sequence of SEQ ID NO: 25.

5. The method of claim 1, wherein the IL-10 agent comprises two IL-10polypeptides each having the amino acid sequence of SEQ ID NO: 26.

6. The method of claim 1, wherein the IL-10 agent comprises two IL-10polypeptides each having the amino acid sequence of SEQ ID NO: 27.

7. The method of claim 1, wherein the IL-10 agent comprises at least one modification to form a modified IL-10 agent, wherein the modification does not alter the amino acid sequence of the IL-10 agent.

8. The method of claim 7, wherein the modification comprises a linker.

9. The method of claim 7, wherein the modified IL-10 agent is a PEG-IL-10 agent.

10. The method of claim 9, wherein the PEG-IL-10 agent comprises at least one PEG molecule covalently attached to at least one amino acid residue of at least one subunit of IL-10.

11. The method of claim 10, wherein the PEG-IL-10 agent comprises a mixture of mono-pegylated and di-pegylated IL-10.

12. The method of claim 9, wherein the PEG component of the PEG-IL-10 agent has a molecular mass from about 5 kDa to about 50 kDa.

13. The method of claim 9, wherein the PEG component of the PEG-IL-10 agent has a molecular mass from about 20 kDa to about 40 kDa.

14. The method of claim 1, wherein the IL-10 agent is PEGylated.

15. The method of claim 1, wherein the IL-10 agent is an Fc fusion molecule.

16. The method of claim 1, wherein the IL-10 agent comprises a serum albumin or an albumin binding domain (ABD).

17. The method of claim 1, wherein the IL-10 agent is glycosylated or hesylated.

18. The method of claim 1, wherein the PD1 pathway inhibitor is selected from the group consisting of pembrolizumab and nivolumab.

19. The method of claim 1, further comprising the addition of a second immune checkpoint pathway modulator.

20. The method of claim 1, wherein the IL-10 agent is administered sufficient to maintain a mean IL-10 agent serum trough concentration of at least 1.0 ng/mL over the course of treatment.

21. The method of claim 1, wherein the administering of the immune checkpoint pathway modulator and the IL-10 agent is by parenteral injection.

22. The method of claim 1, wherein the administering of the IL-10 agent is by subcutaneous injection.

23. The method of claim 1, wherein the immune checkpoint pathway modulator and the IL-10 agent are administered simultaneously.

24. The method of claim 1, wherein the immune checkpoint pathway modulator and the IL-10 agent are administered sequentially.

25. The method of claim 1, further comprising administering at least one additional prophylactic or therapeutic agent.

26. The method of claim 25, wherein the prophylactic or therapeutic agent is a chemotherapeutic agent.

* * * * *